(12) United States Patent
Allen

(10) Patent No.: US 6,867,352 B2
(45) Date of Patent: Mar. 15, 2005

(54) PLANT CELLULOSE SYNTHASES

(75) Inventor: Stephen M. Allen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/900,237

(22) Filed: Jul. 6, 2001

(65) Prior Publication Data

US 2002/0120124 A1 Aug. 29, 2002

Related U.S. Application Data

(63) Continuation-in-part of application No. 09/720,383, filed as application No. PCT/US99/15871 on Jul. 13, 1999.
(60) Provisional application No. 60/092,844, filed on Jul. 14, 1998.

(51) Int. Cl.$^7$ .......................... A01H 1/00; C07H 21/04; C07K 14/415; C12N 5/14; C12N 9/00

(52) U.S. Cl. ...................... 800/295; 435/69.1; 435/468; 435/183; 435/235; 435/325; 435/410; 435/419; 435/252.3; 435/320.1; 530/370; 536/23.2; 536/23.6; 800/278; 800/295

(58) Field of Search .......................... 435/6, 183, 410, 435/419, 252.3, 320.1; 530/350, 370; 536/23.2, 23.6, 24.1; 800/278, 295, 298

(56) References Cited

U.S. PATENT DOCUMENTS 5,723,764 A 3/1998 Nichols et al.

FOREIGN PATENT DOCUMENTS

| EP | 0875575 A2 | 11/1998 |
|---|---|---|
| WO | WO 91/13988 A1 | 9/1991 |
| WO | WO 98/00549 A1 | 1/1998 |
| WO | WO 98/00551 A2 | 1/1998 |
| WO | WO 98/18949 A2 | 5/1998 |
| WO | WO 00/09706 A2 | 2/2000 |
| WO | WO200009706 | 2/2000 |
| WO | WO 00/70058 | 11/2000 |
| WO | WO200179516 | 10/2001 |
| WO | WO2003000898 | 1/2003 |

OTHER PUBLICATIONS

Delmer, Deborah P., "Cellulose Biosynthesis: Exciting Times for A Difficult Field of Study," Annu. Rev. Plant Physiol. Plant Mol. Biol. 1999. 50:245–76.
Richmond, Todd A. et al., "The Cellulose Synthase Superfamily," Plant Physiology, Oct. 2000, vol. 124, pp. 495–498.
Richmond, Todd A., "Higher plant cellulose synthases," Genome Biology 2000, 1(4):reviews3001.1–3001.6.
Arioli, T. et al., Molecular Analysis of Cellulose Biosynthesis in Arabidopsis, EMBL Accession No. AF027172, Feb. 3, 1998, XP002124282.

Tony Arioli et al., Molecular Analysis of Cellulose Biosynthesis in Arabidopsis, Science, vol. 279:717–720, Jan. 30, 1998, XP002124283.
Arioli, T. et al.,Molecular Analysis of Cellulose Biosynthesis in Arabidopsis, EMBL Accession No. AF027173, Feb. 3, 1998, XP002129994.
Pear, J.R. et al., Higher Plants Contain Homologs of the Bacterial CelA Genes Encoding the Catalytic Subunit of Cellulose Synthase, Dec. 13, 1996, EMBL Accession No. U58284, XP002124438.
Pear, Julie R. et al., PNAS, vol. 93:12637–12642, 10/96, Higher Plants Contain Homologs of the Bacterial celA Genes encoding the Catalytic Subunit of Cellulose Synthase, XP002061424.
Pear, J.R. et al., Higher Plants Contain Homologs of the Bacterial celA Genes Encoding the Catalytic Subunit of Cellulose Synthase, Dec. 13, 1996, EMBL Accession No. U58283, XP002124439.
Wu, et al., AraxCelA, a New Member of the Cellulose Synthase Gene Family from Arabidopsis, EMBL Accession No. AF062485, May 18, 1998, XP00219995.
Luguang Wu et al., Plant Phys., vol. 117:1125, 7/98, Arax-CelA, A New Member of Cellulose Synthase Gene Family from *Arabidopsis thaliana*. Accession No. AF062485, XP002130048.
Takuji Sasaki, Rice cDNA, Partial Sequence, EMBL Accession No. D24381, Nov. 29, 1993, DBEST Database ID: 37681, Dec. 2, 1993, XP002124440.
Baek Hie Nahm, Rice Immature Seed Lambda ZAPII cDNA Library Oryza Sativa cDNA Clone 96AS0237, Database DBEST ID: 1473188, Jan. 20, 1998, EMBL Accession No. AA751514, Jan. 21, 1998, XP002129996.
Sasaki, T. et al., Rice cDNA, Partial Sequence (R2668 1A), EMBL Accession No. D24862, Nov. 29, 1993, XP002124441.
Sasaki, T. et al., Rice cDNA, DBEST Database ID:38158, Dec. 2, 1993, XP002124442.
Sasaki, T. et al., Rice cDNA from Callus, EMBL Accession No. D41766, Nov. 15, 1994, XP002129998.
Sasaki, T. et al., Rice cDNA from Callus, GenBank Accession No. D41261, Nov. 15, 1994, XP002129997.
Sasaki, T. et al., Rice cDNA from Root, EMBL Accession No. AU031954, Oct. 19, 1998, XP002129999.
Taylor, N.G. et al., The Irregular Xylem3 Locus of Arabidopsis Encodes a Cellulose Synthase Required for Secondary Cell Wall Synthesis, EMBL Accession No. AF088917, May 25, 1999, XP002130000.

(List continued on next page.)

Primary Examiner—Phuong T. Bui

(57) ABSTRACT

This invention relates to an isolated nucleic acid fragment encoding a cellulose synthase. The invention also relates to the construction of a chimeric gene encoding all or a portion of the cellulose synthase, in sense or antisense orientation, wherein expression of the chimeric gene results in production of altered levels of the cellulose synthase in a transformed host cell.

11 Claims, 4 Drawing Sheets

OTHER PUBLICATIONS

Blewitt, M. et al., ESTs From Developing Cotton Fiber, EMBL Accession No. Al729626, Jun. 12 1999, XP002130001.

Blewitt, M. et al., ESTs From Developing Cotton Fiber, EMBL Accession No. A1729981, Jun. 12, 1999, XP002130002.

Laosinchai, W. et al., Gossypium Cellulose Synthase Catalytic Subunit(celA3) mRNA, EMBL Accession No. AF150630, Jun. 21, 1999, XP002130003.

Yehudit Amor et al., The Plant Cell, vol. 3:989–995, Sep. 1991, Evidence for a Cyclic Diguanlic Acid–Dependent Cellulose Synthase in Plants, XP002061420.

Likun Li et al., Plant Phys., vol. 101:1149–1156, 1993, beta–Glucan Synthesis In the Cotton Fiber, XP002087180.

National Center for Biotechnology Information General Identifier No. 2827139, Feb. 6, 1998, Arioli, T. et al., Molecular Analysis of Cellulose Biosynthesis in Arabidopsis.

National Center for Biotechnology Information General Identifier No. 2827141, Feb. 6, 1998, Arioli, T. et al., Molecular Analysis of Cellulose Biosynthesis in Arabidopsis.

National Center for Biotechnology Information General Identifier No. 4467125, Feb. 26, 1999, Bevan, M. et al.

National Center for Biotechnology Information General Identifier No. 4886756, Jul. 2, 1999, Taylor, N.G. et al., The Irregular Xylem3 Locus of Arabidopsis Encodes a Cellulose Synthase Required for Secondary Cell Wall Synthesis.

Neil G. Taylor et al., The Plant Cell, vol. 11:769–779, May 1999, The Irregular Xylem3 Locus of Arabidopsis Encodes a Cellulose Synthase Required for Secondary Cell Wall Synthesis.

National Center for Biotechnology Information General Identifier No. 3135611, Aug. 7, 1998, Wu, L. et al., Arax-CelA, A New Member of the Cellulose Synthase Gene Family from Arabidopsis.

National Center for Biotechnology Information General Identifier No. 1706958, Dec. 5, 1996, Pear, J.R. et al., Higher Plants Contain Homologs of the Bacterial celA Genes Encoding the Catalytic Subunit of Cellulose Synthase.

National Center for Biotechnology Information General Identifier No. 5081779, Jun. 10, 1999, Kimura, S. et al., Immunogold Labeling of Rosette Terminal Cellulose Synthesizing Complexes in a Vascular Plant.

National Center for Biotechnology Information General Identifier No. 2827143, Feb. 6, 1998, Arioli, T. et al., Molecular analysis of cellulose biosynthesis in Arabiopsis.

Neta Holland et al., Plant Phys., vol. 123:1313–1323, 2000, A comparative analysis of the plant cellulose synthase (CesA) gene family.

EMBL Database Sequence Library Accession No: AF027174, Feb. 3, 1998, Ariolli, T. T Al, Molecular analysis of cellulose biosynthesis in Arabiopsis, XP–002124284.

Figure 1A

```
                              *       ****  *       ** * **
SEQ ID NO:26       AREANAGLVAGSYKRNELVRIRHDSDGGQPKPLKEANGQICQICGDTVGKSATGDTFVAC
SEQ ID NO:30       --------------MDGDADAL--KSGRHGAGDVCQICADGLGTTLDGDVFTAC
SEQ ID NO:33       ----------MESEGETAGKPMKNIVPQTCQICSDNVGKTVDGDRFVAC
                 1                                                             60

* **********  ***  * *  ****  ***   ***             ***
SEQ ID NO:26       NECGFPVCRPCYEYERKDGNQCCPQCKTRYKRQKGSPRVEGDEEEEDVDDLEN--EFNYSG
SEQ ID NO:30       DVCRFPVCRPCYEHERKEGTQACLQCKTKYKRHRGSPAIRGEEGDTDADDGS-DFNYPA
SEQ ID NO:33       DICSFPVCRPCYEYERKDGNQSCPQCKTRYKRLKGSPAIPGDKDEDGLADEGTVEFNYP-
                61                                                             120

*        *          **              *
SEQ ID NO:26       KGKNQK--KVTTARRPWQ---GDQQDIELS------VSSSRHDESQQP---VPLLTHGHS
SEQ ID NO:30       SGTEDQKQKIADRMRSWRMNTGGSGNVGHPKYDSGEIGLSKYDSGEIPRGYVPSVTNSQ-
SEQ ID NO:33       -----QKEKISERMLGWHLTRGKGEEMGEPQYDK----------EVSHNHLPRLTSRQD
               121                                                             180

*       ***
SEQ ID NO:26       VSGEIPTPDNHSIRTTSGPIGPVEKSIPYIDPRQPVAVRIIVDPSKDLNSYGLGNVDWKE
SEQ ID NO:30       MSGEIPGASPD--HHMMSPTGNISRRAPFPY-VNHSPNPSREFSG------SIGNVAWKE
SEQ ID NO:33       TSGEFSAASPE--RLSVSSTIAGGKRLPYSSDVNQSPNRRIVDPV------GLGNVAWKE
               181                                                             240

** ***  **  *                *
SEQ ID NO:26       RVEGWKLKQEKNMVQMTS-----RYPEGKGDTEGTGSNG--EELQMAADDIRQPMSRIVPI
SEQ ID NO:30       RVDGWKMKQDKGAIPMTNGTSIAPSEGRAATDIDASTEYNMEDALLNDETRQPLSRKVPI
SEQ ID NO:33       RVDGWKMKQEKNTGPV----STQAASERGGVDIDASTDILADEALLNDEARQPLSRKVSI
               241                                                             300
```

Figure 1B

```
                  *    ***  *  ***  *   **  *   *    *  ***   ******  ******  ********  ******
SEQ ID NO:26      SSTHLTPYRVVIILRLIILGFFLQYRCTHPVKDAYPLWLTSVICEVWFALSWLLDQFPKW
SEQ ID NO:30      ASSKINPYRMVIVLRLVVLSIFLHYRLTNPVRNAYPLWLLSVICEIWFALSWILDQFPKW
SEQ ID NO:33      PSSRINPYRMVIMLRLVILCLFLHYRITNPVPNAFALWLVSVICEIWFALSWILDQFPKW
                                                                                     360

*  *********  *  ******** *  *   **   ***  *   **   ********  **********
SEQ ID NO:26      SPVNRETYLDRLSMRFDREGEPSQLAPIDVFSTVDPLKEPPLVTANTVLSILAVDYPVD
SEQ ID NO:30      FPINRETYLDRLALRYDREGEPSQLAAVDIFVSTVDPLKEPPIVTANTVLSILAVDYPVD
SEQ ID NO:33      FPVNRETYLDRLALRYDREGEPSQLAAVDIFVSTVDPLKEPPLVTANTVLSILAVDYPVD
                                                                                     420

******  *   *** ** ** *********** **  ******* *  *  ****  *  **********
SEQ ID NO:26      KVSCYVSDDGSAMLTFEALSETAEFAKKWAPFCKKHSIEPRAPEFYFAQKIDYLKDKVQP
SEQ ID NO:30      KVSCYVSDDGASMLTFDALAETSEFARIKWVPFVKKYDIEPRAPEFYFCQKIDYLKDKVQP
SEQ ID NO:33      KVSCYVFDDGAAMLSFESLAETSEFARKWVPFCKKYSIEPRAPEWYFAAKIDYLKDKVQT
                                                                                     480

*****   ********* *  *  ****** *   *  *  *  *********  **********
SEQ ID NO:26      SFVKERRAMKREYEEFKVRINALVAKAQKVPEEGWTMQDGTPWPGNNSRDHPGMIQVFLG
SEQ ID NO:30      SFVKDRRAMKREYEEFKIRINALVSKALKVPEEGWIMQDGTPWPGNNTRDHPGMIQVFLG
SEQ ID NO:33      SFVKDRRAMKREYEEFKIRINALVSKALKCPEEGWVMQDGTPWPGNNTGDHPGMIQVFLG
                                                                                     540

**  *  *****************  *  ********  **********   ** *****
SEQ ID NO:26      HSGGFDTEGNELPRLVYVSREKRPGFQHHKKAGAMNALIRVSAVLTNGAYLLNVDCDHYF
SEQ ID NO:30      HSGGLDTEGNELPRLVYVSREKRPGFQHHKKAGAMNALVRVSAVLTNGQYMLNLDCDHYI
SEQ ID NO:33      QNGGLDAEGNELPRLVYVSREKRPGFQHHKKAGAMNALVRVSAVLTNGPFILNLDCDHYI
                                                                                     600
```

Figure 1C

```
                 ****  ******  *******   ********  *******   *******  *******
SEQ ID NO:26     NNSKCLKEAMCFMDPNLGKKTCYVQFPQRFDGIDLHDRYANRNIVFFDINLKGLDGIQG
SEQ ID NO:30     NNSKAVREAMCFLMDPNLGPNLGPQVCYVQFPQRFDGIDRNDRYANRNTVFFDINLRGLDGIQG
SEQ ID NO:33     NNSKALREAMCFLMDPNLGKQVCYVQFPQRFDGIDKNDRYANRNTVFFDINLRGLDGIQG
                                                                          660

********  ***  ****    *    *   ***       *          **
SEQ ID NO:26     PVYVGTGCCFNRQALYGYDPVLTEEDLEPNIIIKSCCGSRKKGKGGNKKYIDKNRALKRT
SEQ ID NO:30     PVYVGTGCVFNRTAIYGYEPPIKAK--KPGFLASLCGGKKASKS-KKRSSDKKKSNKHV
SEQ ID NO:33     PVYVGTGCVFNRTALYGYEPPIKVKHKKPSLLSKLCGGSRKKNSK-AKKESDKKKSGRHT
                                                                          720

*  **   *****   ****   ********  **  *   ***  *****
SEQ ID NO:26     ESTAPIFNMEDIEEGIE--GYDDERSFLMAQ-SYEKRFGQSPVLIAATFMEQGGLPPSTN
SEQ ID NO:30     DSSVPVFNLEDIEEGVEGAGFDDEKSVLMSQMSLEKRFGQSAAFVASTLMEYGGVPQSST
SEQ ID NO:33     DSTVPVFNLDDIEEGVEGAGFDDEKALLMSQMSLEKRFGSAVFVASTLMENGGVPPSAT
                                                                          780

****************   **  **********  ***   ******      *****
SEQ ID NO:26     SATLLKEAIHVISCGYEDKTEWGKEIGWIYGSVTEDILTGFKMHTRGWISIYCMPPRPAF
SEQ ID NO:30     PESLLKEAIHVISCGYEDKSEWGTEIGWIYGSVTEDILTGFKMHARGWRSVYCMPKRPAF
SEQ ID NO:33     PENLLKEAIHVISCGYEDKSDWGMEIGWIYGSVTEDILTGFKMHARGWRSIYCMPKLPAF
                                                                          840

***************************  ***  *******  **  *********
SEQ ID NO:26     KGSAPINLSDRLNQVLRWALGSIEILLSRHCPIWYGYSGRLKFLERLAYINTIVYPLTSI
SEQ ID NO:30     KGSAPINLSDRLNQVLRWALGSVEILFSRHCPLWYGYGGRLKFLERFAYINTTIYPLTSL
SEQ ID NO:33     KGSAPINLSDRLNQVLRWALGSVEILFSRHCPIWYGYNGRLKFLERFAYVNTTIYPITSI
                                                                          900
```

Figure 1D

```
            *** * * * *   * *  ****** * *** ****** ****** ******
SEQ ID NO:26  PLLAYCTLPAICLLTGKFIVPEISNYASIWFILLFVSIFSTGILELRWSGVTLEDWWRNE
SEQ ID NO:30  PLLVYCILPAICLLTGKFIMPEISNLASIWFIALFLSIFATGILEMRWSGVGIDEWWRNE
SEQ ID NO:33  PLLMYCTLLAVCLFTNQFIIPQISNIASIWFLSLFLSIFATGILEMRWSGVGIDEWWRNE
                                                                   960

*******  ***** ********  ********* ** ********* *******
SEQ ID NO:26  QFWVIGGTSAHLFAVFQGLLKVLAGIDTNFTVTSKASDEDGDFAELYVFKWTSLLIPPTT
SEQ ID NO:30  QFWVIGGISAHLFAVFQGLLKVLAGIDTNFTVTSKANDEEGDFAELYMFKWTLLLIPPTT
SEQ ID NO:33  QFWVIGGVSAHLFAVFQGILKVLAGIDTNFTVTSKASDEDGDFAELYLFKWTTLLIPPTT
                                                                  1020

*  *  * *** *   ************* ************ ***********
SEQ ID NO:26  ILVVNMVGIVAGVSFAINSGYQSWGPLFGRLFFAIWVIVHLYPFLKGLLGRQNRTPTIVI
SEQ ID NO:30  ILIINMVGVVAGTSYAINSGYQSWGPLFGKLFFAFWVIVHLYPFLKGLLGRQNRTPTIVI
SEQ ID NO:33  LLIVNLVGVVAGVSYAINSGYQSWGPLFGKLFFAFWVIVHLYPFLKGLMGRQNRTPTIVV
                                                                   1080

** ************ ****               *   ***  *
SEQ ID NO:26  VWSVLLASIFSLLWVRIDPFTSDSTKAR-GQCGIDC
SEQ ID NO:30  VWAVLLASIFSLLWVRVDPFTTRLAGPNIQTCGINC
SEQ ID NO:33  VWSVLLASIFSLLWVRIDPFTSRVTGPDILECGINC
                                               1116
```

PLANT CELLULOSE SYNTHASES

This application is a continuation-in part of U.S. patent application Ser. No. 09/720,383, filed Dec. 21, 2000, which is the national filing of PCT/US99/15871, filed Jul. 13, 1999, which claims the benefit of U.S. Provisional Application No. 60/092,844, filed Jul. 14, 1998.

FIELD OF THE INVENTION

This invention is in the field of plant molecular biology. More specifically, this invention pertains to nucleic acid fragments encoding cellulose synthase in plants and seeds.

BACKGROUND OF THE INVENTION

Cellulose is a major component of plant fiber, e.g. cotton fiber. Cellulose is composed of crystalline beta-1,4-glucan microfibrils (see World Patent Publication No. WO 98/00549). These microfibrils are strong and can resist enzymatic and mechanical degradation and are important in determining nutritional quality of animal and human foodstuffs. Hence, modification of the biosynthetic pathway responsible for cellulose synthesis through modification of cellulose synthase activity could potentially alter fiber quantity, either by producing more or less fiber in a particular plant species or in a specific organ or tissue of a particular plant. Modification of cellulose synthase activity could increase the value of the fiber to the end-user and may improve the structural integrity of the plant cell wall. Lastly, because cellulose is a major cell wall component, inhibition of cellulose synthesis would probably be lethal. Thus, cellulose synthase may serve as the target for a novel class of herbicides. Plant cellulose synthase genes, homologs of the bacterial celA genes encoding the catalytic subunit of cellulose synthase, have been reported from cotton, Arabidopsis, corn, rice and alfala (Arioli et al. (1998) *Science* 279:717–720; Holland et al. (2000) *Plant Physiol* 123:1313–1324; World Patent Publication Nos. WO 98/00549, WO 98/18949, and WO 00/09706).

There is a great deal of interest in identifying the genes that encode proteins involved in cellulose synthesis. These genes may be used in plant cells to control the synthesis of cellulose. Accordingly, the availability of nucleic acid sequences encoding all or a portion of a cellulose synthase would facilitate studies to better understand cellulose synthesis in plants and provide genetic tools to alter cellulose production.

SUMMARY OF THE INVENTION

The present invention concerns an isolated polynucleotide comprising: (a) a first nucleotide sequence encoding a first polypeptide comprising at least 750 amino acids, wherein the amino acid sequence of the first polypeptide and the amino acid sequence of SEQ ID NO: 30 have at least 80%, 85%, 90%, or 95% identity based on the Clustal alignment method, (b) a second nucleotide sequence encoding a second polypeptide comprising at least 650 amino acids, wherein the amino acid sequence of the second polypeptide and the amino acid sequence of SEQ ID NO: 26 have at least 85%, 90%, or 95% identity based on the Clustal alignment method, (c) a third nucleotide sequence encoding a third polypeptide comprising at least 100 amino acids, wherein the amino acid sequence of the third polypeptide and the amino acid sequence of SEQ ID NO: 24 have at least 90% or 95% identity based on the Clustal alignment method, (d) a fourth nucleotide sequence encoding a fourth polypeptide comprising at least 100 amino acids, wherein the amino acid sequence of the fourth polypeptide and the amino acid sequence of SEQ ID NO: 28 have at least 95% identity based on the Clustal alignment method, or (e) the complement of the first, second, third, or fourth nucleotide sequence, wherein the complement and the first, second, third, or fourth nucleotide sequence contain the same number of nucleotides and are 100% complementary. The first polypeptide preferably comprises the amino acid sequence of SEQ ID NO: 30, the second polypeptide preferably comprises the amino acid sequence of SEQ ID NO: 26, the third polypeptide preferably comprises the amino acid sequence of SEQ ID NO: 24, and the fourth polypeptide preferably comprises the amino acid sequence of SEQ ID NO: 28. The first nucleotide sequence preferably comprises the nucleotide sequence of SEQ ID NO: 29, the second nucleotide sequence preferably comprises the nucleotide sequence of SEQ ID NO: 25, the third nucleotide sequence preferably comprises the nucleotide sequence of SEQ ID NO: 23, and the fourth nucleotide sequence preferably comprises the nucleotide sequence of SEQ ID NO: 27. The first, second, third, and fourth polypeptides preferably are cellulose synthases.

In a second embodiment, the present invention relates to a chimeric gene comprising any of the isolated polynucleotides of the present invention operably linked to a regulatory sequence, and a cell, a plant, and a seed comprising the chimeric gene.

In a third embodiment, the present invention relates to a vector comprising any of the isolated polynucleotides of the present invention.

In a fourth embodiment, the present invention relates to an isolated polynucleotide fragment comprising a nucleotide sequence comprised by any of the polynucleotides of the present invention, wherein the nucleotide sequence contains at least 30, 40, or 60 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention relates to a method for producing a transgenic plant comprising transforming a plant cell with any of the isolated polynucleotides of the present invention and regenerating a plant from the transformed plant cell, the transgenic plant produced by this method, and the seed obtained from this transgenic plant.

In a seventh embodiment, the present invention concerns an isolated polypeptide comprising: (a) a first amino acid sequence comprising at least 750 amino acids, wherein the first amino acid sequence and the amino acid sequence of SEQ ID NO: 30 have at least 80%, 85%, 90%, or 95% identity based on the Clustal alignment method, (b) a second amino acid sequence comprising at least 650 amino acids, wherein the second amino acid sequence and the amino acid sequence of SEQ ID NO: 26 have at least 85%, 90%, or 95% identity based on the Clustal alignment method, (c) a third amino acid sequence comprising at least 100 amino acids, wherein the third amino acid sequence and the amino acid sequence of SEQ ID NO: 24 have at least 90% or 95% identity based on the Clustal alignment method, or (d) a fourth amino acid sequence comprising at least 100 amino acids, wherein the fourth amino acid sequence and the amino acid sequence of SEQ ID NO: 28 have at least 95% identity based on the Clustal alignment method. The first amino acid sequence preferably comprises the amino acid sequence of SEQ ID NO: 30, the second amino acid sequence preferably comprises the amino acid sequence of SEQ ID NO: 26, the third amino acid sequence preferably comprises the amino acid sequence of SEQ ID NO: 24, and the fourth amino acid sequence preferably comprises the amino acid sequence of SEQ ID NO: 28. The polypeptide preferably is a cellulose synthase.

In an eighth embodiment, the present invention relates to a virus, preferably a baculovirus, comprising any of the isolated polynucleotides of the present invention or any of the chimeric genes of the present invention.

In a ninth embodiment, the invention relates to a method of selecting an isolated polynucleotide that affects the level of expression of a cellulose synthase protein or enzyme activity in a host cell, preferably a plant cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level of the cellulose synthase protein or enzyme activity in the host cell containing the isolated polynucleotide; and (d) comparing the level of the cellulose synthase protein or enzyme activity in the host cell containing the isolated polynucleotide with the level of the cellulose synthase protein or enzyme activity in the host cell that does not contain the isolated polynucleotide.

In a tenth embodiment, the invention concerns a method of obtaining a nucleic acid fragment encoding a substantial portion of a cellulose synthase protein, preferably a plant cellulose synthase protein, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:23, 25, 27, and 29, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a cellulose synthase protein amino acid sequence.

In an eleventh embodiment, this invention relates to a method of obtaining a nucleic acid fragment encoding all or a substantial portion of the amino acid sequence encoding a cellulose synthase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a twelfth embodiment, this invention concerns a method for positive selection of a transformed cell comprising: (a) transforming a host cell with the chimeric gene of the present invention or an expression cassette of the present invention; and (b) growing the transformed host cell, preferably a plant cell, such as a monocot or a dicot, under conditions which allow expression of the cellulose synthase polynucleotide in an amount sufficient to complement a null mutant to provide a positive selection means.

In a thirteenth embodiment, this invention relates to a method of altering the level of expression of a cellulose synthase protein in a host cell comprising: (a) transforming a host cell with a chimeric gene of the present invention; and (b) growing the transformed host cell under conditions that are suitable for expression of the chimeric gene wherein expression of the chimeric gene results in production of altered levels of the cellulose synthase protein in the transformed host cell.

A further embodiment of the instant invention is a method for evaluating at least one compound for its ability to inhibit the activity of a cellulose synthase, the method comprising the steps of: (a) transforming a host cell with a chimeric gene comprising a nucleic acid fragment encoding a cellulose synthase polypeptide, operably linked to a suitable regulatory sequence; (b) growing the transformed host cell under conditions that are suitable for expression of the chimeric gene wherein expression of the chimeric gene results in production of the cellulose synthase polypeptide encoded by the chimeric gene in the transformed host cell; (c) optionally purifying the cellulose synthase polypeptide expressed by the transformed host cell; (d) treating the cellulose synthase polypeptide with a compound to be tested; and (e) comparing the activity of the cellulose synthase polypeptide that has been treated with a test compound to the activity of an untreated cellulose synthase polypeptide, and selecting compounds with potential for inhibitory activity.

BRIEF DESCRIPTION OF THE DRAWING AND SEQUENCE LISTINGS

The invention can be more fully understood from the following detailed description and the accompanying drawing and Sequence Listing which form a part of this application.

FIGS. 1A, 1B, 1C and 1D depict the amino acid sequence alignment between the cellulose synthases encoded by the following: (a) nucleotide sequence derived from garden balsam clone ids.pk0029.h10 (SEQ ID NO:26), (b) nucleotide sequence derived from wheat clone wlmk4.pk0015.a11 (SEQ ID NO:30), and (c) nucleotide sequence from *Arabidopsis thaliana* (NCBI GenBank Identifier (GI) No. 2827143; SEQ ID NO:33). Amino acids which are conserved among all and at least two sequences with an amino acid at that position are indicated with an asterisk (*). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs or PCR fragment sequence ("Contig*"), or sequences encoding the entire protein derived from an EST, an FIS, a contig, or an FIS and PCR fragment sequence ("CGS"). SEQ ID NOs:1–22 correspond to SEQ ID NOs:1–22, respectively, presented in U.S. patent application Ser. No. 09/720383, filed Dec. 21, 2000, and in WO 00/04166 which published Jan. 27, 2000. The sequence descriptions and Sequence Listing attached hereto comply with the rules governing nucleotide and/or amino acid sequence disclosures in patent applications as set forth in 37 C.F.R. § 1.821–1.825.

TABLE 1

Cellulose Synthase

| Plant | Clone Designation | Status | SEQ ID NO: (Nucleotide) | SEQ ID NO: (Amino Acid) |
|---|---|---|---|---|
| Barley | bsh1.pk0002.f6 | FIS | 1 | 2 |
| Corn | Contig of cco1n.pk0005.g3 cdt2c.pk002.g1 cdt2c.pk002.116 csc1c.pk002.i1 p0031.ccmar05rb p0110.cgsma57r | Contig | 3 | 4 |
| Corn | cr1n.pk0135.e10 | FIS | 5 | 6 |
| Corn | p0097.cqrad17rc | CGS | 7 | 8 |
| Corn | p0122.ckamh70rc | CGS | 9 | 10 |
| Rice | r1r24.pk0073.g1 | EST | 11 | 12 |
| Soybean | sdp2c.pk005.o22 | FIS | 13 | 14 |
| Soybean | ses8w.pk0028.f3 | EST | 15 | 16 |
| Soybean | ss1.pk0036.c10 | EST | 17 | 18 |
| Wheat | Contig of w11.pk0009.c9 wr1.pk0160.d11 wre1n.pk0043.f9 wre1n.pk0043.h8 wre1n.pk0131.g10 | Contig | 19 | 20 |
| Wheat | w11n.pk0044.b1 | EST | 21 | 22 |
| Florida Bitterbush | pps.pk0001.d6 | FIS | 23 | 24 |
| Garden Balsam | ids.pk0029.h10 | FIS | 25 | 26 |
| Soybean | sre.pk0042.b3 | FIS | 27 | 28 |
| Wheat | w1mk4.pk0015.a11 (FIS) | CGS | 29 | 30 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 60 contiguous nucleotides, preferably at least 40 contiguous nucleotides, most preferably at least 30 contiguous nucleotides derived from SEQ ID NOs:23, 25, 27, or 29, or the complement of such sequences.

The term "isolated" polynucleotide refers to a polynucleotide that is substantially free from other nucleic acid sequences, such as and not limited to other chromosomal and extrachromosomal DNA and RNA. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:23, 25, 27, and 29, and the complement of such nucleotide sequences may be used in methods of selecting an isolated polynucleotide that affects the expression of a cellulose synthase polypeptide in a host cell. A method of selecting an isolated polynucleotide that affects the level of expression of a polypeptide in a virus or in a host cell (eukaryotic, such as plant or yeast, prokaryotic such as bacterial) may comprise the steps of: constructing an isolated polynucleotide of the present invention or an isolated chimeric gene of the present invention; introducing the isolated polynucleotide or the isolated chimeric gene into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250, 650, or 750 amino acids. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et at. (1993) J. Mol. Biol. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Null mutant" refers here to a host cell which either lacks the expression of a certain polypeptide or expresses a polypeptide which is inactive or does not have any detectable expected enzymatic function.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can farther be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, enviromnentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising: (a) a first nucleotide sequence encoding a first polypeptide comprising at least 750 amino acids, wherein the amino acid sequence of the first polypeptide and the amino acid sequence of SEQ ID NO: 30 have at least 80%, 85%, 90%, or 95% identity based on the Clustal alignment method, (b) a second nucleotide sequence encoding a second polypeptide comprising at least 650 amino acids, wherein the amino acid sequence of the second polypeptide and the amino acid sequence of SEQ ID NO: 26 have at least 85%, 90%, or 95% identity based on the Clustal alignment method, (c) a third nucleotide sequence encoding a third polypeptide comprising at least 100 amino acids, wherein the amino acid sequence of the third polypeptide and the amino acid sequence of SEQ ID NO: 24 have at least 90% or 95% identity based on the Clustal alignment method, (d) a fourth nucleotide sequence encoding a fourth polypeptide comprising at least 100 amino acids, wherein the amino acid sequence of the fourth polypeptide and the amino acid sequence of SEQ ID NO: 28 have at least 95% identity based on the Clustal alignment method, or (e) the complement of the first, second, third, or fourth nucleotide sequence, wherein the complement and the first, second, third, or fourth nucleotide sequence contain the same number of nucleotides and are 100% complementary. The first polypeptide preferably comprises the amino acid sequence of SEQ ID NO: 30, the second polypeptide preferably comprises the amino acid sequence of SEQ ID NO: 26, the third polypeptide preferably comprises the amino acid sequence of SEQ ID NO: 24, and the fourth polypeptide preferably comprises the amino acid sequence of SEQ ID NO: 28. The first nucleotide sequence preferably comprises the nucleotide sequence of SEQ ID NO: 29, the second nucleotide sequence preferably comprises the nucleotide sequence of SEQ ID NO: 25, the third nucleotide sequence preferably comprises the nucleotide sequence of SEQ ID NO: 23, and the fourth nucleotide sequence preferably comprises the nucleotide sequence of SEQ ID NO: 27. The first, second, third, and fourth polypeptides preferably are cellulose synthases.

Nucleic acid fragments encoding at least a portion of several cellulose synthases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other cellulose synthases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci.* USA 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci.* USA 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:23, 25, 27, and 29 and the complement of such nucleotide sequences may be used in such methods to obtain a nucleic acid fragment encoding a substantial portion of an amino acid sequence of a polypeptide.

The present invention relates to a method of obtaining a nucleic acid fragment encoding a substantial portion of a cellulose synthase polypeptide, preferably a substantial portion of a plant cellulose synthase polypeptide, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:23, 25, 27, and 29, and the complement of such nucleotide sequences; and amplifying a nucleic acid fragment (preferably a cDNA inserted in a cloning vector) using the oligonucleotide primer. The amplified nucleic acid fragment preferably will encode a portion of a cellulose synthase polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the chimeric genes of the invention as described herein or an isolated polynucleotide of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of cellulose synthase and cellulose in those cells.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant isolated polynucleotide (or chimeric gene) may be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikbel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns an isolated polypeptide comprising: (a) a first amino acid sequence comprising at least 750 amino acids, wherein the first amino acid sequence and the amino acid sequence of SEQ ID NO: 30 have at least 80%, 85%, 90%, or 95% identity based on the Clustal alignment method, (b) a second amino acid sequence comprising at least 650 amino acids, wherein the second amino acid sequence and the amino acid sequence of SEQ ID NO: 26 have at least 85%, 90%, or 95% identity based on the Clustal alignment method, (c) a third amino acid sequence comprising at least 100 amino acids, wherein the third amino acid sequence and the amino acid sequence of SEQ ID NO: 24 have at least 90% or 95% identity based on the Clustal alignment method, or (d) a fourth amino acid sequence comprising at least 100 amino acids, wherein the fourth amino acid sequence and the amino acid sequence of SEQ ID NO: 28 have at least 95% identity based on the Clustal alignment method. The first amino acid sequence preferably comprises the amino acid sequence of SEQ ID NO: 30, the second amino acid sequence preferably comprises the amino acid sequence of SEQ ID NO: 26, the third amino acid sequence preferably comprises the amino acid sequence of SEQ ID NO: 24, and the fourth amino acid sequence preferably comprises the amino acid sequence of SEQ ID NO: 28. The polypeptide preferably is a cellulose synthase.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded cellulose synthase. An example of a vector for high level expression of the instant polypeptides in a bacterial host is provided (Example 6).

Additionally, the instant polypeptides can be used as a target to facilitate design and/or identification of inhibitors of those enzymes that may be useful as herbicides. This is desirable because the polypeptides described herein catalyze a step in the synthesis of cellulose. Accordingly, inhibition of the activity of one or more of the enzymes described herein could lead to inhibition of plant growth. Thus, the instant polypeptides could be appropriate for new herbicide discovery and design.

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J. Hum. Genet. 32:314–331).

The production and use of plant gene-derived probes for use in genetic mapping is described in Bernatzky and Tanksley (1986) Plant Mol. Biol. Reporter 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) Genome Res. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) J. Lab. Clin. Med. 11:95–96), polymorphism of PCR-amplified fragments (CAPS; Sheffield et al. (1993) Genomics 16:325–332), allele-specific ligation (Landegren et al. (1988) Science 241:1077–1080), nucleotide extension reactions (Sokolov (1990) Nucleic Acid Res. 18:3671), Radiation Hybrid Mapping (Walter et al. (1997) Nat. Genet. 7:22–28) and Happy Mapping (Dear and Cook (1989) Nucleic Acid Res. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) Proc. Natl. Acad. Sci USA 86:9402–9406; Koes et al. (1995) Proc. Natl. Acad. Sci USA 92:8149–8153; Bensen et al. (1995) Plant Cell 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various barley (*Hordeum vulgare*), corn (*Zea mays*), rice (*Oryza sativa*), soybean (*Glycine max*), wheat (*Triticum aestivum*), Florida bitterbush (*Picramnia pentandra*), and garden balsam (*Impatiens balsamia*) tissues were prepared. The characteristics of the libraries are described below.

TABLE 2 cDNA Libraries from Barley, Corn, Rice, Soybean, Wheat, Florida Bitterbush, and Garden Balsam

| Library | Tissue | Clone |
|---|---|---|
| bsh1 | Barley Sheath, Developing Seedling | bsh1.pk0002.f6 |
| cco1n | Corn Cob of 67 Day Old Plants Grown in Green House* | cco1n.pk0005.g3 |
| cdt2c | Corn Developing Tassel | cdt2c.pk002.g1 |
|  |  | cdt2c.pk002.l16 |
| cr1n | Corn Root From 7 Day Old Seedlings* | cr1n.pk0135.e10 |
| csc1c | Corn 20 Day Old Seedling (Germination Cold Stress) | csc1c.pk002.i1 |
| ids | *Impatiens balsamia* Developing Seed | ids.pk0029.h10 |

TABLE 2-continued cDNA Libraries from Barley, Corn, Rice, Soybean, Wheat, Florida Bitterbush, and Garden Balsam

| Library | Tissue | Clone |
|---|---|---|
| p0031 | Corn Shoot Culture | p0031.ccmar05rb |
| p0097 | Corn V9** Whorl Section (7 cm) From Plant Infected Four Times With European Corn Borer | p0097.cqrad17rc |
| p0110 | Corn (Stages V3/V4**) Leaf Tissue Minus Midrib Harvested 4 Hours, 24 Hours and 7 Days After Infiltration With Salicylic Acid, Pooled* | p0110.cgsma57r |
| p0122 | Pith Tissue Collected From Internode Subtending Ear Node at 5 Days After Pollination* | p0122.ckamh70rc |
| pps | *Picramnia pentandra* (Florida Bitterbush) Developing Seed | pps.pk0001.d6 |
| rlr24 | Resistant Rice Leaf 15 Days After Germination, 24 Hours After Infection of Strain *Magnaporthe grisea* 4360-R-62 (AVR2-YAMO) | rlr24.pk0073.g1 |
| sdp2c | Soybean Developing Pod (6–7 mm) | sdp2c.pk005.o22 |
| ses8w | Soybean Mature Embryo 8 Weeks After Subculture | ses8w.pk0028.f3 |
| sre | Soybean Root Elongation Zone, 4 to 5 Days After Germination | sre.pk0042.b3 |
| ssl | Soybean Seedling 5–10 Days After Germination | ssl.pk0036.c10 |
| wl1 | Wheat Leaf From 7 Day Old Seedling Light Grown | wl1.pk0009.c9 |
| wl1n | Wheat Leaf From 7 Day Old Seedling Light Grown* | wl1n.pk0044.b1 |
| wlmk4 | Wheat Seedlings 4 Hours After Inoculation With *Erysiphe graminis* f. sp tritici and Treatment with Herbicide*** | wlmk4.pk0015.a11 |
| wr1 | Wheat Root From 7 Day Old Light Grown Seedling | wr1.pk0160.d11 |
| wre1n | Wheat Root From 7 Day Old Etiolated Seedling* | wre1n.pk0043.f9 |
| | | wre1n.pk0043.h8 |
| | | wre1n.pk0131.g10 |

*These libraries were normalized essentially as described in U.S. Pat. No. 5,482,845, incorporated herein by reference.
**Corn developmental stages (V3, V4, and V9) are explained in the publication "How a corn plant develops" from the Iowa State University Coop. Ext. Service Special Report No. 48 reprinted June 1993.
***Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH 10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding cellulose synthases were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5-or 3-prime can be found by using the BLASTn algorithm (Altschul et al (1997) *Nucleic Acids Res.* 25:3389–3402.) against the DuPont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Cellulose Synthase

The BLASTX search using the EST sequences from clones listed in Table 3 revealed similarity of the polypeptides encoded by the cDNAs to cellulose synthase from *Arabidopsis thaliana* (NCBI GenBank Identifier No. gi 2827139, gi 2827141, gi 4467125, gi 4886756 and gi 3135611) and *Gossypium hirsutum* (NCBI GenBank Identifier No. gi 1706958 and 5081779). Shown in Table 3 are the BLAST results for individual ESTs ("EST"), the sequences of the entire cDNA inserts comprising the indicated cDNA clones ("FIS"), complete gene sequences ("CGS") or contigs assembled from two or more ESTs ("Contig"):

TABLE 3

BLAST Results for Sequences Encoding Polypeptides Homologous to *Arabidopsis thaliana* and *Gossypium hirsutum* Cellulose Synthase

| Clone | Status | BLAST pLog Score |
| --- | --- | --- |
| bsh1.pk0002.f6 | FIS | 154.00 (gi 2827139) |
| Contig composed of: | Contig | >254.00 (gi 2827141) |
| cco1n.pk0005.g3 | | |
| cdt2c.pk002.g1 | | |
| cdt2c.pk002.l16 | | |
| csc1c.pk002.i1 | | |
| p0031.ccmar05rb | | |
| p0110.cgsma57r | | |
| cr1n.pk0135.e10 | FIS | 176.00 (gi 1706958) |
| p0097.cqrad17rc | CGS | >254.00 (gi 2827141) |
| p0122.ckamh70rc | CGS | >254.00 (gi 2827141) |
| rlr24.pk0073.g1 | EST | 77.70 (gi 4467125) |
| sdp2c.pk005.o22 | FIS | >254.00 (gi 4886756) |
| ses8w.pk0028.f3 | EST | >254.00 (gi 2827139) |
| ssl.pk0036.c10 | EST | >254.00 (gi 2827141) |
| Contig composed of: | Contig | >254.00 (gi 5081779) |
| wl1.pk0009.c9 | | |
| wr1.pk0160.d11 | | |
| wre1n.pk0043.f9 | | |
| wre1n.pk0043.h8 | | |
| wre1n.pk0131.g10 | | |
| wl1n.pk0044.b1 | EST | 166.00 (gi 3135611) |

The data in Table 4 represents a calculation of the percent identity of the amino acid sequences set forth in SEQ ID NOs:2, 4, 8, 10, 12, 14, 16, 18, 20 and 22 and the *Arabi* dopsis thaliana (SEQ ID NOs:23, 24, 26, 27 and 29) and Gossypium hirsutum (SEQ ID NOs:31 and 32) sequences.

TABLE 4

Percent Identity of Amino Acid Sequences Deduced From the Nucleotide Sequences of cDNA Clones Encoding Polypeptides Homologous to Arabidopsis thaliana and Gossypium hirsutum Cellulose Synthase

| SEQ ID NO. | Percent Identity to |
|---|---|
| 2 | 82% (gi 2827139) |
| 4 | 69% (gi 2827141) |
| 6 | 89% (gi 1706958) |
| 8 | 70% (gi 2827141) |
| 10 | 70% (gi 2827141) |
| 12 | 36% (gi 4467125) |
| 14 | 86% (gi 4886756) |
| 16 | 88% (gi 2827139) |
| 18 | 86% (gi 2827141) |
| 20 | 87% (gi 5081779) |
| 22 | 70% (gi 3135611) |

Sequence alignments and percent identity calculations were performed using the Megalign program of the LASER-GENE bioinformatics computing suite (DNASTAR Inc., Madision Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilites indicate that the nucleic acid fragments comprising the instant cDNA clones encode a substantial portion of a cellulose synthase. These sequences represent the first barley, corn, rice, soybean and wheat sequences encoding cellulose synthase.

Further sequencing and searching of the DuPont proprietary database allowed the identification of other soybean, wheat, Florida bitterbush, and garden balsam clones encoding cellulose synthase. The BLASTX search using the EST sequences from clones listed in Table 5 revealed similarity of the polypeptides encoded by the cDNAs to cellulose synthase from Arabidopsis thaliana (NCBI GenBank Identifier (GI) Nos. 2827139, 2827141, and 2827143). Shown in Table 5 are the BLAST results for individual ESTs ("EST"), the sequences of the entire cDNA inserts comprising the indicated cDNA clones ("FIS"), the sequences of contigs assembled from two or more ESTs ("Contig"), sequences of contigs assembled from an FIS and one or more ESTs ("Contig*"), or sequences encoding an entire protein derived from an FIS, a contig, or an FIS and PCR ("CGS"):

TABLE 5

BLAST Results for Sequences Encoding Polypeptides Homologous to Cellulose Synthase

| Clone | Status | BLAST Results | |
|---|---|---|---|
| | | NCBI GI No. | pLog Score |
| pps.pk0001.d6 | FIS | 2827141 | >180.00 |
| ids.pk0029.h10 | FIS | 2827139 | >180.00 |
| sre.pk0042.b3 | FIS | 2827143 | >180.00 |
| wlmk4.pk0015.a11 (FIS) | CGS | 2827143 | >180.00 |

FIGS. 1A, 1B, 1C and 1D present an alignment of the amino acid sequences set forth in SEQ ID NOs:26 and 30 and the Arabidopsis thaliana sequence (NCBI GI No. 2827143; SEQ ID NO:33). The data in Table 6 represents a calculation of the percent identity of the amino acid sequences set forth in SEQ ID NOs:26 and 30 and the Arabidopsis thaliana sequence (NCBI GI No. 2827143; SEQ ID NO:33).

TABLE 6

Percent Identity of Amino Acid Sequences Deduced From the Nucleotide Sequences of cDNA Clones Encoding Polypeptides Homologous to Cellulose Synthase

| SEQ ID NO. | Percent Identity to NCBI GI No. 2827143; SEQ ID NO: 33 |
|---|---|
| 26 | 67.4 |
| 30 | 76.5 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a cellulose synthase. These sequences represent the first Florida bitterbush and garden balsam sequences encoding cellulose synthase known to Applicant.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL 1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35 S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.

(1983) Gene 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Examples 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Evaluating Compounds for Their Ability to Inhibit the Activity of Cellulose Synthase The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for cellulose synthase activity are presented in WO 98/18949 and WO 98/00549.

What is claimed is:

1. An isolated polynucleotide comprising:
   (a) a nucleotide sequence encoding a polypeptide having cellulose synthase activity, wherein the polypeptide has an amino acid sequence of at least 90% sequence identity, based on the Clustal V method of alignment, when compared to SEQ ID NO:30, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 95% sequence identity, based on the Clustal V method of alignment, when compared to SEQ ID NO:30.

3. The polynucleotide of claim 1, wherein the amino acid sequence of the polypeptide comprises SEQ ID NO:30.

4. The polynucleotide of claim 1, wherein the nucleotide sequence comprises SEQ ID NO:29.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

<160> NUMBER OF SEQ ID NOS: 33

<210> SEQ ID NO 1
<211> LENGTH: 1221
<212> TYPE: DNA
<213> ORGANISM: Hordeum vulgare

<400> SEQUENCE: 1

```
gcacgaggat attcttactg ggtttaaaat gcacgcaaga ggttggatat caatctactg        60
catgccacca cgaccttgtt tcaagggttc tgcgccaatc aatctctctg accgtctcaa       120
tcaagttctc cggtgggctc ttgggtcagt tgaaattctg tttagcagac attgtcctat       180
ctggtacaat tacggtgggc ggttgaaact tctggagagg atggcttaca tcaacaccat       240
tgtttatcca ataacatccc ttccacttat cgcctattgt gtgcttcctg ctatctgtct       300
cctcaccaac aaatttatca ttcccgagat cagtaactat gctgggatgt tctttattct       360
tatgtttgcc tccatctttg ccacgggtat attggagctg cgatggagtg gtgtcggcat       420
cgaggactgg tggagaaacg agcagttctg ggttattggt ggcacatctg cccatctttt       480
cgcagtgttc cagggtctgc tgaaggtgtt ggccgggatt gacaccaact tcacggttac       540
ctcgaaggca aacgacgagg atggcgattt tgctgagtta tacgtgttca agtggaccag       600
tctcctcatt cctccgacca ccgtccttgt gattaacctg gtgggcatgg tggcaggcat       660
atcatatgcc atcaacagcg gttaccagtc ttggggtcca ctcttcggaa agctcttctt       720
ctcaatctgg gtgatcctcc atctctaccc cttcctcaag ggtctcatgg ggaagcagaa       780
ccgcacgcca accatcgtca ttgtttggtc catcctccta gcctccatct tctccctcct       840
gtgggtgaag atcgaccctt tcatatccga tacccagaaa gccgtcgcca tggggcagtg       900
tggcgtcaac tgctgatcgg cgccgaagag tatctgcccc cctcgtgtaa ataccggagg       960
gggttggatg ggattttgtt gttgtagatg aagacggagt tttatgtaag ttattattgc      1020
cccttcgtgc tgagaagcac aaaccgtgaa gcctacgaaa cctgcagcgt acattgtgat      1080
ttttttctcc ttttcttttc atctgtgata cctgttgttt cttcttagag tatattatgt      1140
cagaacgtat ctatagttct atacacacta tgacaccaac tatttatata aggcagctgt      1200
tgcatcaact cttctgcaaa a                                                1221
```

<210> SEQ ID NO 2
<211> LENGTH: 304
<212> TYPE: PRT
<213> ORGANISM: Hordeum vulgare

<400> SEQUENCE: 2

```
His Glu Asp Ile Leu Thr Gly Phe Lys Met His Ala Arg Gly Trp Ile
 1               5                  10                  15

Ser Ile Tyr Cys Met Pro Pro Arg Pro Cys Phe Lys Gly Ser Ala Pro
            20                  25                  30

Ile Asn Leu Ser Asp Arg Leu Asn Gln Val Leu Arg Trp Ala Leu Gly
        35                  40                  45

Ser Val Glu Ile Leu Phe Ser Arg His Cys Pro Ile Trp Tyr Asn Tyr
    50                  55                  60

Gly Gly Arg Leu Lys Leu Leu Glu Arg Met Ala Tyr Ile Asn Thr Ile
65                  70                  75                  80

Val Tyr Pro Ile Thr Ser Leu Pro Leu Ile Ala Tyr Cys Val Leu Pro
                85                  90                  95

Ala Ile Cys Leu Leu Thr Asn Lys Phe Ile Ile Pro Glu Ile Ser Asn
            100                 105                 110

Tyr Ala Gly Met Phe Phe Ile Leu Met Phe Ala Ser Ile Phe Ala Thr
        115                 120                 125

Gly Ile Leu Glu Leu Arg Trp Ser Gly Val Gly Ile Glu Asp Trp Trp
    130                 135                 140

Arg Asn Glu Gln Phe Trp Val Ile Gly Gly Thr Ser Ala His Leu Phe
145                 150                 155                 160

Ala Val Phe Gln Gly Leu Leu Lys Val Leu Ala Gly Ile Asp Thr Asn
                165                 170                 175

Phe Thr Val Thr Ser Lys Ala Asn Asp Glu Asp Gly Asp Phe Ala Glu
            180                 185                 190

Leu Tyr Val Phe Lys Trp Thr Ser Leu Leu Ile Pro Pro Thr Thr Val
        195                 200                 205

Leu Val Ile Asn Leu Val Gly Met Val Ala Gly Ile Ser Tyr Ala Ile
    210                 215                 220

Asn Ser Gly Tyr Gln Ser Trp Gly Pro Leu Phe Gly Lys Leu Phe Phe
225                 230                 235                 240

Ser Ile Trp Val Ile Leu His Leu Tyr Pro Phe Leu Lys Gly Leu Met
                245                 250                 255

Gly Lys Gln Asn Arg Thr Pro Thr Ile Val Ile Val Trp Ser Ile Leu
            260                 265                 270

Leu Ala Ser Ile Phe Ser Leu Leu Trp Val Lys Ile Asp Pro Phe Ile
        275                 280                 285

Ser Asp Thr Gln Lys Ala Val Ala Met Gly Gln Cys Gly Val Asn Cys
    290                 295                 300
```

<210> SEQ ID NO 3
<211> LENGTH: 3776
<212> TYPE: DNA
<213> ORGANISM: Zea mays

<400> SEQUENCE: 3

```
gcgcgccgcg caggcgcaac gcaacaaagg gaaacccag  ccggaggagc aaaagctagc      60
aagcgtgtcc ctccccctcc ctcactcccg tttcattcca ttcccccca  gacgccgcta     120 ccgccgccgc cgcacgcacg cttgcccggg gatctggaga tctggtagcg ccaggggat      180 ggaggccagc gccgggctgg tcgccggctc gcacaaccgg aacgagctcg tcgtcatccg     240
```

-continued

```
ccgcgatggc gagccagggc cgaagcccat ggaccagcgg aacggccagg tgtgccagat      300
ttgcggcgac gacgtgggc gcaaccccga cggggagccg ttcgtggcct gcaacgagtg       360
cgccttcccc atctgccggg actgctacga gtacgagcgc cgcgaggca cgcagaactg       420
cccccagtgc aagacccgct tcaagcgcct caagggtgc gcgcgcgtgc ccggggacga      480
ggaggaggac ggcgtcgacg acctggagaa cgagttcaac tggagcgaca agcacgactc     540
ccagtacctc gccgagtcca tgctccacgc ccacatgagc tacggccgcg gcgccgacct     600
cgacggcgtg ccgcagccat tccacccccat ccccaatgtt ccctcctca caacggaca     660
gatggtcgat gacatcccgc cggaccagca cgcccttgtg ccctcgttcg tgggtggcgg    720
ggggaagagg attcaccctc tcccgtacgc ggatcccaac cttcctgtgc aaccgaggtc    780
tatggaccct tccaaggatc tcgccgcata tggctacggg agcgtagcat ggaaggagag    840
gatggagagc tggaagcaga agcaggagag gatgcaccag acgaggaacg atggcggcgg    900
cgatgatggt gatgatgcag atctaccact aatggatgaa gctagacagc cattgtccag    960
aaagatcccg cttccttcaa gccaaatcaa cccctatagg atgattataa taattcggct   1020
agtggttttg tgtttcttct tccactaccg agtgatgcat ccggtgcctg atgcatttgc   1080
tttatggctc atatctgtga tctgtgaaat ttggtttgcc atgtcttgga ttcttgacca   1140
gtttccaaag tggtttccta cgagaggga acctatctt gaccggctga gtttaaggtt    1200
tgacaaggaa gggcatcctt ctcaactcgc ccctgttgat ttctttgtca gtacggttga   1260
tcccttgaag gaacctccat tggtcactgc taatactgtt ctatctatcc tttcggtgga   1320
ttatccagtt gataaggttt catgctacgt ttctgatgat ggtgctgcca tgctgacatt   1380
tgaagcattg tctgaaacat ctgaatttgc aaagaaatgg gttcctttct gcaaaagata   1440
tagccttgag cctcgtgctc cagagtggta cttccaacag aagatagact acctgaaaga   1500
caaggtggcg ccaaactttg ttagagaacg gagagcaatg aagagagagt atgaggaatt   1560
caaggtcaga atcaatgcct tggttgctaa agcccaaaag gttcctgagg aaggatggac   1620
aatgcaggat ggaactccat ggcccggaaa taatgtccgt gatcatcctg gaatgattca   1680
ggttttcctt ggtcaaagtg gtggccatga tgtggaagga aatgagctgc ctcgattggt   1740
ttatgtttca agagaaaaac ggccaggcta caaccatcac aagaaggctg gtgctatgaa   1800
tgcattggtc cgagtctctg ctgtactaac taatgctcct tatttgctga acttggattg   1860
tgatcactat atcaataata gtaaggctat aaaggaagca atgtgttta tgatggatcc   1920
tttgcttgga aagaaagttt gctatgtgca gtttcctcaa agatttgatg ggattgatcg   1980
ccatgatcga tatgctaaca gaaatgttgt cttttcgat atcaacatga aggtttgga   2040
tggtatccag ggcccaattt atgtgggtac tggatgtgtc ttcagaaggc aggcattata   2100
tggctacgat gctcccaaaa caaagaagcc accatcaaga acttgcaact gctggccaaa   2160
gtggtgcatt tgctgttgct gttttggtaa caggaagacc aagaagaaga ccaagacctc   2220
taaacctaaa tttgagaaga taagaaaact ttttaagaaa aaggaaaatc aagcccctgc   2280
atatgctctt ggtgaaattg atgaagccgc tccaggagct gaaaatgaaa aggctagtat   2340
tgtaaatcaa cagaagttgg aaaagaaatt tggccagtct tcagtttttg ttgcatccac   2400
acttcttgag aatggtggaa ccctgaagag tgccagtcca gcttctcttc tgaaggaagc   2460
tatacatgtc atcagttgtg gatatgaaga caaaacaggc tggggaaaag atattggttg   2520
gatttatgga tcagtcacag aagatattct tactgggttt aagatgcact gccatggttg   2580
```

-continued

```
gcggtcaatt tactgcatac ctaaacgggc cgccttcaaa ggttccgcac ctctcaatct    2640
ttccgatcgt cttcaccagg ttcttcggtg ggctcttggt tcaattgaaa ttttcttcag    2700
caaccactgc cctctctggt atgggtatgg tggtggacta agttcctgg aaaggttttc     2760 gtacattaac tccatcgtat acccttggac atctatcccg ctcttggcct attgcacatt    2820
gcctgccatc tgcttgctga cagggaaatt tatcacgcca gagcttaaca atgttgccag    2880
cctctggttc atgtcacttt tcatctgcat ttttgctacg agcatcctgg aaatgagatg    2940
gagtggtgta ggcatcgatg actggtggag aaacgagcag ttttgggtca ttggaggcgt    3000
gtcttcacat ctctttgctg tgttccaggg actcctcaag gtcatagctg gtgtagacac    3060
gagcttcact gtgacatcca agggcggaga cgacgaggag ttctcagagc tgtacacatt    3120
caaatggacg acccttctga tacctccgac aaccctgctc ctactgaact tcattggagt    3180
ggtagctggc atctccaatg cgatcaacaa cggatatgaa tcatggggcc ccctgttcgg    3240
gaagctcttc tttgcatttt gggtgatcgt ccatctttac ccgttcctca agggtctggt    3300
tgggaggcag aacaggacgc caacgattgt cattgtctgg tccatcctcc tggcttcgat    3360
cttctcgctg ctttgggtcc ggatcgaccc gttccttgcg aaggatgatg gtcccctgtt    3420
ggaggagtgt ggtctggatt gcaactagga ggtcagcacg tggacttccc cgtcagtgtg    3480
tggtcgaaga agtattttg cagatgtttt gtgcccatat ttcttttttc aattttgtc     3540 cctctgtaga tagaaacaag gggagaaggg gaaaaaagt acttgtattt cttttgttcc     3600
atggtggtgg tggtggtggg cggctcagcc tcgtgagtgc agtattgggc aaaccggagg    3660
ctgcggcaac cttgtgcagt tcggccacga atatactagg gaagatcgcg accaatcaat    3720
caatcgatga ccgagttcaa ttgttcagca aaaaaaaaa aaaaaaaaaa aaaaaa        3776
```

<210> SEQ ID NO 4
<211> LENGTH: 1148
<212> TYPE: PRT
<213> ORGANISM: Zea mays

<400> SEQUENCE: 4

```
Arg Ala Ala Gln Ala Gln Arg Asn Lys Gly Lys Pro Gln Pro Glu Glu
  1               5                  10                  15

Gln Lys Leu Ala Ser Val Ser Leu Pro Leu Pro His Ser Arg Phe Ile
                 20                  25                  30

Pro Phe Pro Pro Arg Arg Arg Tyr Arg Arg Arg Thr His Ala Cys
             35                  40                  45

Pro Gly Ile Trp Arg Ser Gly Ser Ala Arg Gly Met Glu Ala Ser Ala
         50                  55                  60

Gly Leu Val Ala Gly Ser His Asn Arg Asn Glu Leu Val Val Ile Arg
 65                  70                  75                  80

Arg Asp Gly Glu Pro Gly Pro Lys Pro Met Asp Gln Arg Asn Gly Gln
                 85                  90                  95

Val Cys Gln Ile Cys Gly Asp Asp Val Gly Arg Asn Pro Asp Gly Glu
            100                 105                 110

Pro Phe Val Ala Cys Asn Glu Cys Ala Phe Pro Ile Cys Arg Asp Cys
        115                 120                 125

Tyr Glu Tyr Glu Arg Arg Glu Gly Thr Gln Asn Cys Pro Gln Cys Lys
    130                 135                 140

Thr Arg Phe Lys Arg Leu Lys Gly Cys Ala Arg Val Pro Gly Asp Glu
145                 150                 155                 160

Glu Glu Asp Gly Val Asp Asp Leu Glu Asn Glu Phe Asn Trp Ser Asp
```

-continued

```
                165                 170                 175
Lys His Asp Ser Gln Tyr Leu Ala Glu Ser Met Leu His Ala His Met
                180                 185                 190
Ser Tyr Gly Arg Gly Ala Asp Leu Asp Gly Val Pro Gln Pro Phe His
                195                 200                 205
Pro Ile Pro Asn Val Pro Leu Leu Thr Asn Gly Gln Met Val Asp Asp
                210                 215                 220
Ile Pro Pro Asp Gln His Ala Leu Val Pro Ser Phe Val Gly Gly Gly
225                             230                 235                 240
Gly Lys Arg Ile His Pro Leu Pro Tyr Ala Asp Pro Asn Leu Pro Val
                245                 250                 255
Gln Pro Arg Ser Met Asp Pro Ser Lys Asp Leu Ala Ala Tyr Gly Tyr
                260                 265                 270
Gly Ser Val Ala Trp Lys Glu Arg Met Glu Ser Trp Lys Gln Lys Gln
                275                 280                 285
Glu Arg Met His Gln Thr Arg Asn Asp Gly Gly Asp Asp Gly Asp
                290                 295                 300
Asp Ala Asp Leu Pro Leu Met Asp Glu Ala Arg Gln Pro Leu Ser Arg
305                             310                 315                 320
Lys Ile Pro Leu Pro Ser Ser Gln Ile Asn Pro Tyr Arg Met Ile Ile
                325                 330                 335
Ile Ile Arg Leu Val Val Leu Cys Phe Phe Phe His Tyr Arg Val Met
                340                 345                 350
His Pro Val Pro Asp Ala Phe Ala Leu Trp Leu Ile Ser Val Ile Cys
                355                 360                 365
Glu Ile Trp Phe Ala Met Ser Trp Ile Leu Asp Gln Phe Pro Lys Trp
                370                 375                 380
Phe Pro Ile Glu Arg Glu Thr Tyr Leu Asp Arg Leu Ser Leu Arg Phe
385                             390                 395                 400
Asp Lys Glu Gly His Pro Ser Gln Leu Ala Pro Val Asp Phe Phe Val
                405                 410                 415
Ser Thr Val Asp Pro Leu Lys Glu Pro Pro Leu Val Thr Ala Asn Thr
                420                 425                 430
Val Leu Ser Ile Leu Ser Val Asp Tyr Pro Val Asp Lys Val Ser Cys
                435                 440                 445
Tyr Val Ser Asp Asp Gly Ala Ala Met Leu Thr Phe Glu Ala Leu Ser
                450                 455                 460
Glu Thr Ser Glu Phe Ala Lys Lys Trp Val Pro Phe Cys Lys Arg Tyr
465                             470                 475                 480
Ser Leu Glu Pro Arg Ala Pro Glu Trp Tyr Phe Gln Gln Lys Ile Asp
                485                 490                 495
Tyr Leu Lys Asp Lys Val Ala Pro Asn Phe Val Arg Glu Arg Arg Ala
                500                 505                 510
Met Lys Arg Glu Tyr Glu Glu Phe Lys Val Arg Ile Asn Ala Leu Val
                515                 520                 525
Ala Lys Ala Gln Lys Val Pro Glu Glu Gly Trp Thr Met Gln Asp Gly
                530                 535                 540
Thr Pro Trp Pro Gly Asn Asn Val Arg Asp His Pro Gly Met Ile Gln
545                             550                 555                 560
Val Phe Leu Gly Gln Ser Gly Gly His Asp Val Glu Gly Asn Glu Leu
                565                 570                 575
Pro Arg Leu Val Tyr Val Ser Arg Glu Lys Arg Pro Gly Tyr Asn His
                580                 585                 590
```

```
His Lys Lys Ala Gly Ala Met Asn Ala Leu Val Arg Val Ser Ala Val
            595                 600                 605

Leu Thr Asn Ala Pro Tyr Leu Leu Asn Leu Asp Cys Asp His Tyr Ile
            610                 615                 620

Asn Asn Ser Lys Ala Ile Lys Glu Ala Met Cys Phe Met Met Asp Pro
625                 630                 635                 640

Leu Leu Gly Lys Lys Val Cys Tyr Val Gln Phe Pro Gln Arg Phe Asp
            645                 650                 655

Gly Ile Asp Arg His Asp Arg Tyr Ala Asn Arg Asn Val Val Phe Phe
            660                 665                 670

Asp Ile Asn Met Lys Gly Leu Asp Gly Ile Gln Gly Pro Ile Tyr Val
            675                 680                 685

Gly Thr Gly Cys Val Phe Arg Arg Gln Ala Leu Tyr Gly Tyr Asp Ala
            690                 695                 700

Pro Lys Thr Lys Lys Pro Pro Ser Arg Thr Cys Asn Cys Trp Pro Lys
705                 710                 715                 720

Trp Cys Ile Cys Cys Cys Phe Gly Asn Arg Lys Thr Lys Lys Lys
            725                 730                 735

Thr Lys Thr Ser Lys Pro Lys Phe Glu Lys Ile Lys Lys Leu Phe Lys
            740                 745                 750

Lys Lys Glu Asn Gln Ala Pro Ala Tyr Ala Leu Gly Glu Ile Asp Glu
            755                 760                 765

Ala Ala Pro Gly Ala Glu Asn Glu Lys Ala Ser Ile Val Asn Gln Gln
            770                 775                 780

Lys Leu Glu Lys Lys Phe Gly Gln Ser Ser Val Phe Val Ala Ser Thr
785                 790                 795                 800

Leu Leu Glu Asn Gly Gly Thr Leu Lys Ser Ala Ser Pro Ala Ser Leu
            805                 810                 815

Leu Lys Glu Ala Ile His Val Ile Ser Cys Gly Tyr Glu Asp Lys Thr
            820                 825                 830

Gly Trp Gly Lys Asp Ile Gly Trp Ile Tyr Gly Ser Val Thr Glu Asp
            835                 840                 845

Ile Leu Thr Gly Phe Lys Met His Cys His Gly Trp Arg Ser Ile Tyr
850                 855                 860

Cys Ile Pro Lys Arg Ala Ala Phe Lys Gly Ser Ala Pro Leu Asn Leu
865                 870                 875                 880

Ser Asp Arg Leu His Gln Val Leu Arg Trp Ala Leu Gly Ser Ile Glu
            885                 890                 895

Ile Phe Phe Ser Asn His Cys Pro Leu Trp Tyr Gly Tyr Gly Gly Gly
            900                 905                 910

Leu Lys Phe Leu Glu Arg Phe Ser Tyr Ile Asn Ser Ile Val Tyr Pro
            915                 920                 925

Trp Thr Ser Ile Pro Leu Leu Ala Tyr Cys Thr Leu Pro Ala Ile Cys
            930                 935                 940

Leu Leu Thr Gly Lys Phe Ile Thr Pro Glu Leu Asn Asn Val Ala Ser
945                 950                 955                 960

Leu Trp Phe Met Ser Leu Phe Ile Cys Ile Phe Ala Thr Ser Ile Leu
            965                 970                 975

Glu Met Arg Trp Ser Gly Val Gly Ile Asp Asp Trp Trp Arg Asn Glu
            980                 985                 990

Gln Phe Trp Val Ile Gly Gly Val Ser Ser His Leu Phe Ala Val Phe
            995                 1000                1005
```

Gln Gly Leu Leu Lys Val Ile Ala Gly Val Asp Thr Ser Phe Thr Val
    1010                1015                1020

Thr Ser Lys Gly Gly Asp Asp Glu Glu Phe Ser Glu Leu Tyr Thr Phe
1025                1030                1035                1040

Lys Trp Thr Thr Leu Leu Ile Pro Pro Thr Thr Leu Leu Leu Leu Asn
                1045                1050                1055

Phe Ile Gly Val Val Ala Gly Ile Ser Asn Ala Ile Asn Asn Gly Tyr
            1060                1065                1070

Glu Ser Trp Gly Pro Leu Phe Gly Lys Leu Phe Phe Ala Phe Trp Val
        1075                1080                1085

Ile Val His Leu Tyr Pro Phe Leu Lys Gly Leu Val Gly Arg Gln Asn
    1090                1095                1100

Arg Thr Pro Thr Ile Val Ile Val Trp Ser Ile Leu Leu Ala Ser Ile
1105                1110                1115                1120

Phe Ser Leu Leu Trp Val Arg Ile Asp Pro Phe Leu Ala Lys Asp Asp
                1125                1130                1135

Gly Pro Leu Leu Glu Glu Cys Gly Leu Asp Cys Asn
            1140                1145

<210> SEQ ID NO 5
<211> LENGTH: 1189
<212> TYPE: DNA
<213> ORGANISM: Zea mays

<400> SEQUENCE: 5
gcacgagacc gagtgggcca aggagattgg gtggatctat gggtcggtga cagaggatat      60
cctgacgggg ttcaagatgc actgccgggg gtggaagtcc gtgtactgca cgccgacacg     120
gccggcgttc aaggggtcgg cgcccatcaa cttgtctgat cgtctccacc aggtgctgcg     180
ctgggcgctg ggtccgtgg agatcttcat gagccgccac tgcccgctct ggtacgccta      240
cggcggccgg ctcaagtggc tggagcgctt cgcctacacc aacaccatcg tgtaccccct     300
cacctccatc ccgctcctcg cctactgcac catccccgcc gtctgcctgc tcaccggcaa     360
gttcatcatt cccacgctga caacctcgc cagcatctgg ttcatcgcgc tcttcctgtc      420
catcatcgcg acgagcgtcc tggagctgcg gtggagcggg gtgagcatcg aggactggtg     480
gcgcaacgag cagttctggg tcatcggcgg cgtgtccgcg catctcttcg ccgtgttcca     540
gggcttcctc aaggttctgg gcggcgtgga caccagcttc accgtcacct ccaaggcggc     600
cggcgacgag gccgacgcct cggggaccct ctacctcttc aagtggacca ccctgctggt     660
gccccccacc acgctcatca tcatcaacat ggtgggcatc gtggccggcg tgtccgacgc     720
cgtcaacaac ggctacgggct cctggggccc gctcttcggc aagctcttct ctccttctg    780
ggtcatcgtc cacctctacc cgttcctcaa ggggctcatg ggaggcaga accggacgcc     840
caccatcgtc gtgctctggt ccatcctcct gcctccatc ttctcgctcg tctgggtcag    900
gatcgacccg tttatcccga aggccaaggg ccccatcctc aagccatgcg agtcgagtg     960
ctgagctcac ctagctacct tcttgttgca tgtacggacg ccgccgtgcg tttggacata    1020
caggcacttt tgggccaggc tactcatgtt cgactttttt tttaattttg tacaagattt    1080
gtgatcgagt gactgagtga gacagagtgt gggtgtaag aactgtgatg gaattcactc     1140
aaattaatgg acattttttt tcttcaactg caaaaaaaaa aaaaaaaa                  1189

<210> SEQ ID NO 6
<211> LENGTH: 320
<212> TYPE: PRT

<213> ORGANISM: Zea mays

<400> SEQUENCE: 6

```
His Glu Thr Glu Trp Gly Lys Glu Ile Gly Trp Ile Tyr Gly Ser Val
 1               5                  10                  15
Thr Glu Asp Ile Leu Thr Gly Phe Lys Met His Cys Arg Gly Trp Lys
            20                  25                  30
Ser Val Tyr Cys Thr Pro Thr Arg Pro Ala Phe Lys Gly Ser Ala Pro
        35                  40                  45
Ile Asn Leu Ser Asp Arg Leu His Gln Val Leu Arg Trp Ala Leu Gly
    50                  55                  60
Ser Val Glu Ile Phe Met Ser Arg His Cys Pro Leu Trp Tyr Ala Tyr
65                  70                  75                  80
Gly Gly Arg Leu Lys Trp Leu Glu Arg Phe Ala Tyr Thr Asn Thr Ile
                85                  90                  95
Val Tyr Pro Phe Thr Ser Ile Pro Leu Leu Ala Tyr Cys Thr Ile Pro
            100                 105                 110
Ala Val Cys Leu Leu Thr Gly Lys Phe Ile Ile Pro Thr Leu Asn Asn
        115                 120                 125
Leu Ala Ser Ile Trp Phe Ile Ala Leu Phe Leu Ser Ile Ile Ala Thr
    130                 135                 140
Ser Val Leu Glu Leu Arg Trp Ser Gly Val Ser Ile Glu Asp Trp Trp
145                 150                 155                 160
Arg Asn Glu Gln Phe Trp Val Ile Gly Val Ser Ala His Leu Phe
                165                 170                 175
Ala Val Phe Gln Gly Phe Leu Lys Val Leu Gly Gly Val Asp Thr Ser
            180                 185                 190
Phe Thr Val Thr Ser Lys Ala Ala Gly Asp Glu Ala Asp Ala Phe Gly
        195                 200                 205
Asp Leu Tyr Leu Phe Lys Trp Thr Thr Leu Leu Val Pro Pro Thr Thr
    210                 215                 220
Leu Ile Ile Ile Asn Met Val Gly Ile Val Ala Gly Val Ser Asp Ala
225                 230                 235                 240
Val Asn Asn Gly Tyr Gly Ser Trp Gly Pro Leu Phe Gly Lys Leu Phe
                245                 250                 255
Phe Ser Phe Trp Val Ile Val His Leu Tyr Pro Phe Leu Lys Gly Leu
            260                 265                 270
Met Gly Arg Gln Asn Arg Thr Pro Thr Ile Val Val Leu Trp Ser Ile
        275                 280                 285
Leu Leu Ala Ser Ile Phe Ser Leu Val Trp Val Arg Ile Asp Pro Phe
    290                 295                 300
Ile Pro Lys Ala Lys Gly Pro Ile Leu Lys Pro Cys Gly Val Glu Cys
305                 310                 315                 320
```

<210> SEQ ID NO 7
<211> LENGTH: 3786
<212> TYPE: DNA
<213> ORGANISM: Zea mays

<400> SEQUENCE: 7

```
ccacagctca tataccaaga gccggagcag cttagcgcag cccagagcgg cgccgcgcca      60
agcacaaccc ccacccgcca cagccgcgtg cgcatgtgag cggtcgccgc ggccgggaga     120
ccagaggagg ggaggactac gtgcatttcg ctgtgccgcc gccgcggggt tcgtgcgcga     180
gcgagatccg gcggggcggg gcgggggggcc tgagatggag gctagcgcgg ggctggtggc     240
```

```
                                              -continued cggctcgcat aaccggaacg agctggtggt gatccgccgc gaccgcgagt cgggagccgc    300
gggcggcggc gcggcgcgcc gggcggaggc gccgtgccag atatgcggcg acgaggtcgg    360
ggtgggcttc gacggggagc ccttcgtggc gtgcaacgag tgcgccttcc ccgtctgccg    420
cgcctgctac gagtacgagc gccgcgaggg ctcgcaagcg tgcccgcagt gcaggacccg    480
ctacaagcgc tcaagggct gcccgcgggt ggccggcgac gaggaggagg acggcgtcga    540
cgacctggag ggcgagttcg gcctgcagga cggcgccgcc cacgaggacg acccgcagta    600
cgtcgccgag tccatgctca gggcgcagat gagctacggc cgcggcggcg acgcgcaccc    660
cggcttcagc cccgtcccca acgtgccgct cctcaccaac ggccagatgg ttgatgacat    720
cccgccggag cagcacgcgc tcgtgccgtc ctacatgagc ggcggcggcg cgggggcaa    780 gaggatccac ccgctcccctt tcgcagatcc caaccttcca gtgcaaccga gatccatgga    840
cccgtccaag gatctggccg cctacggata tggcagcgtg gcctggaagg agagaatgga    900
gggctggaag cagaagcagg agcgcctgca gcatgtcagg agcgagggtg gcggtgattg    960
ggatggcgac gatgcagatc tgccactaat ggatgaagct aggcagccat tgtccagaaa    1020
agtccctata tcatcaagcc gaattaatcc ctacaggatg attatcgtta tccggttggt    1080
ggttttgggt ttcttcttcc actaccgagt gatgcatccg gcgaaagatg catttgcatt    1140
gtggctcata tctgtaatct gtgaaatctg gtttgcgatg tcctggattc ttgatcagtt    1200
cccaaagtgg cttccaatcg agagagagac ttacctggac cgtttgtcac taaggtttga    1260
caaggaaggt caaccctctc agcttgctcc aatcgacttc tttgtcagta cggttgatcc    1320
cacaaaggaa cctcccttgg tcacagcgaa cactgtcctt tccatccttt ctgtggatta    1380
tccggttgag aaggtctcct gctatgtttc tgatgatggt gctgcaatgc ttacgtttga    1440
agcattgtct gaaacatctg aatttgcaaa gaaatgggtt cctttcagca aaaagtttaa    1500
tatcgagcct cgtgctcctg agtggtactt ccaacagaag atagactacc tgaaagacaa    1560
ggttgctgct tcatttgtta gggagaggag ggcgatgaag agagaatacg aggaattcaa    1620
ggtaaggatc aatgccttgg ttgcaaaagc ccaaaaggtt cctgaggaag atgatgacaat    1680 gcaagatgga agccctggc ctggaaacaa cgtacgcgat catcctggaa tgattcaggt    1740
attccttggc caaagtggcg gtcgtgatgt ggaaggaaat gagttgcctc gcctggttta    1800
tgtctcgaga gaaaagaggc caggttataa ccatcacaag aaggctggtg ccatgaatgc    1860
actggtccgt gtctctgctg tcttatcaaa tgctgcatac ctattgaact tggactgtga    1920
tcactacatc aacaatagca aggccataaa agaggctatg tgtttcatga tggatccttt    1980 ggtgggggaag aaagtgtgct atgtacagtt ccctcagagg tttgatggta ttgacaaaaa    2040
tgatcgatac gctaacagga acgttgtctt ttttgacatc aacatgaaag gtttggacgg    2100
tattcaagga cccatttatg tgggtactgg atgtgttttc agacggcagg cactgtatgg    2160
ttatgatgct cctaaaacga agaagccacc atcaagaact tgcaactgct ggcccaagtg    2220
gtgcctctct tgctgctgca gcaggaacaa gaataaaaag aagactacaa aaccaaagac    2280
ggagaagaag aaaagattat ttttcaagaa agcagaaaac ccatctcctg catatgcttt    2340
gggtgaaatt gatgaaggtg ctccaggtgc tgatatcgag aaggccggaa tcgtaaatca    2400
acagaaacta gagaagaaat ttgggcagtc ttctgttttt gtcgcatcaa cacttcttga    2460
gaacggaggg accctgaaga gcgcaagtcc agcttctctt ctgaaggaag ctatacatgt    2520
tatcagctgc ggctacgaag acaagaccga ctggggaaaa gagattggct ggatttacgg    2580
```

-continued

```
atcgatcaca gaggatatct tgactggatt taagatgcac tgccatggct ggcggtctat    2640
ttactgcatc ccgaagcggc ctgcattcaa aggttctgcg cctctgaacc tttccgaccg    2700
tcttcaccag gtccttcgct gggcccttgg gtccgtcgaa attttcttca gcaagcactg    2760
cccactttgg tacggatacg gcggcgggct aaaattcctg aaaggtttt cttatatcaa     2820 ctccatcgtt tatccctgga cgtccattcc tctcctggct tactgtacct tgcctgccat    2880
ctgcctgctc acggggaagt ttatcacacc agagcttacc aatgtcgcca gtatctggtt    2940
catggcactt ttcatctgca ctccgtgac cggcatcctg gaaatgaggt ggagtggcgt     3000
ggccatcgac gactggtgga ggaacgagca gttctgggtc atcggaggcg tttcggcgca    3060
tctgttcgcg gtgttccagg cctgctgaa ggtgttcgcc ggcatcgaca cgagcttcac     3120
cgtgacgtcg aaggccgggg acgacgagga gttctcggag ctgtacacgt tcaagtggac    3180
caccctgctg atacccccga ccacgctcct cctgctgaac ttcatcgggg tggtggccgg    3240
gatctcgaac gcgatcaaca acgggtacga gtcgtgggc ccctgttcg ggaagctctt      3300 cttcgccttc tgggtgatcg tccacctgta cccgttcctc aagggtctgg tggggaggca    3360
gaacaggacg ccgacgatcg tcatcgtctg gtccatcctg ctggcctcga tcttctcgct    3420
cctgtgggtc cgcgtcgacc cgttcctcgc caagagcaac ggcccgctcc tggaggagtg    3480
tggcctggac tgcaactgaa gtgggggccc cctgtcactc gaagttctgt cacgggcgaa    3540
ttacgcctga tttttgttg ttgttgttgt tggaattctt tgctgtagat agaaaccaca     3600
tgtccacggc atctctgctg tgtccattgg agcaggagag aggtgcctgc tgctgtttgt    3660
tgagtaaatt aaaagtttta aagttataca gtgatgcaca ttccagtgcc cagtgtattc    3720 ccttttaca gtctgtatat tagcgacaaa ggacatattg gttaggagtt tgattctttt     3780
gtaaaa                                                              3786
```

<210> SEQ ID NO 8
<211> LENGTH: 1165
<212> TYPE: PRT
<213> ORGANISM: Zea mays

<400> SEQUENCE: 8

```
His Ser Ser Tyr Thr Lys Ser Arg Ser Leu Ala Gln Pro Arg Ala
 1               5                  10                  15

Ala Pro Arg Gln Ala Gln Pro Pro Ala Thr Ala Ala Cys Ala Cys
                20                  25                  30

Glu Arg Ser Pro Arg Pro Gly Asp Gln Arg Arg Gly Gly Leu Arg Ala
            35                  40                  45

Phe Arg Cys Ala Ala Ala Ala Gly Phe Val Arg Glu Arg Asp Pro Ala
        50                  55                  60

Gly Arg Gly Gly Gly Pro Glu Met Glu Ala Ser Ala Gly Leu Val Ala
    65                  70                  75                  80

Gly Ser His Asn Arg Asn Glu Leu Val Val Ile Arg Arg Asp Arg Glu
                85                  90                  95

Ser Gly Ala Ala Gly Gly Ala Ala Arg Arg Ala Glu Ala Pro Cys
            100                 105                 110

Gln Ile Cys Gly Asp Glu Val Gly Val Gly Phe Asp Gly Glu Pro Phe
        115                 120                 125

Val Ala Cys Asn Glu Cys Ala Phe Pro Val Cys Arg Ala Cys Tyr Glu
    130                 135                 140

Tyr Glu Arg Arg Glu Gly Ser Gln Ala Cys Pro Gln Cys Arg Thr Arg
145                 150                 155                 160
```

```
Tyr Lys Arg Leu Lys Gly Cys Pro Arg Val Ala Gly Asp Glu Glu
            165                 170                 175
Asp Gly Val Asp Asp Leu Glu Gly Glu Phe Gly Leu Gln Asp Gly Ala
            180                 185                 190
Ala His Glu Asp Asp Pro Gln Tyr Val Ala Glu Ser Met Leu Arg Ala
            195                 200                 205
Gln Met Ser Tyr Gly Arg Gly Asp Ala His Pro Gly Phe Ser Pro
    210                 215                 220
Val Pro Asn Val Pro Leu Leu Thr Asn Gly Gln Met Val Asp Asp Ile
225                 230                 235                 240
Pro Pro Glu Gln His Ala Leu Val Pro Ser Tyr Met Ser Gly Gly Gly
                245                 250                 255
Gly Gly Gly Lys Arg Ile His Pro Leu Pro Phe Ala Asp Pro Asn Leu
            260                 265                 270
Pro Val Gln Pro Arg Ser Met Asp Pro Ser Lys Asp Leu Ala Ala Tyr
        275                 280                 285
Gly Tyr Gly Ser Val Ala Trp Lys Glu Arg Met Glu Gly Trp Lys Gln
    290                 295                 300
Lys Gln Glu Arg Leu Gln His Val Arg Ser Glu Gly Gly Asp Trp
305                 310                 315                 320
Asp Gly Asp Asp Ala Asp Leu Pro Leu Met Asp Glu Ala Arg Gln Pro
                325                 330                 335
Leu Ser Arg Lys Val Pro Ile Ser Ser Ser Arg Ile Asn Pro Tyr Arg
            340                 345                 350
Met Ile Ile Val Ile Arg Leu Val Val Leu Gly Phe Phe His Tyr
    355                 360                 365
Arg Val Met His Pro Ala Lys Asp Ala Phe Ala Leu Trp Leu Ile Ser
        370                 375                 380
Val Ile Cys Glu Ile Trp Phe Ala Met Ser Trp Ile Leu Asp Gln Phe
385                 390                 395                 400
Pro Lys Trp Leu Pro Ile Glu Arg Glu Thr Tyr Leu Asp Arg Leu Ser
                405                 410                 415
Leu Arg Phe Asp Lys Glu Gly Gln Pro Ser Gln Leu Ala Pro Ile Asp
            420                 425                 430
Phe Phe Val Ser Thr Val Asp Pro Thr Lys Glu Pro Pro Leu Val Thr
        435                 440                 445
Ala Asn Thr Val Leu Ser Ile Leu Ser Val Asp Tyr Pro Val Glu Lys
    450                 455                 460
Val Ser Cys Tyr Val Ser Asp Asp Gly Ala Ala Met Leu Thr Phe Glu
465                 470                 475                 480
Ala Leu Ser Glu Thr Ser Glu Phe Ala Lys Lys Trp Val Pro Phe Ser
                485                 490                 495
Lys Lys Phe Asn Ile Glu Pro Arg Ala Pro Glu Trp Tyr Phe Gln Gln
            500                 505                 510
Lys Ile Asp Tyr Leu Lys Asp Lys Val Ala Ala Ser Phe Val Arg Glu
        515                 520                 525
Arg Arg Ala Met Lys Arg Glu Tyr Glu Glu Phe Lys Val Arg Ile Asn
    530                 535                 540
Ala Leu Val Ala Lys Ala Gln Lys Val Pro Glu Gly Trp Thr Met
545                 550                 555                 560
Gln Asp Gly Ser Pro Trp Pro Gly Asn Asn Val Arg Asp His Pro Gly
                565                 570                 575
```

-continued

```
Met Ile Gln Val Phe Leu Gly Gln Ser Gly Gly Arg Asp Val Glu Gly
            580                 585                 590

Asn Glu Leu Pro Arg Leu Val Tyr Val Ser Arg Glu Lys Arg Pro Gly
            595                 600                 605

Tyr Asn His His Lys Lys Ala Gly Ala Met Asn Ala Leu Val Arg Val
            610                 615                 620

Ser Ala Val Leu Ser Asn Ala Ala Tyr Leu Leu Asn Leu Asp Cys Asp
625                 630                 635                 640

His Tyr Ile Asn Asn Ser Lys Ala Ile Lys Glu Ala Met Cys Phe Met
                    645                 650                 655

Met Asp Pro Leu Val Gly Lys Lys Val Cys Tyr Val Gln Phe Pro Gln
            660                 665                 670

Arg Phe Asp Gly Ile Asp Lys Asn Asp Arg Tyr Ala Asn Arg Asn Val
            675                 680                 685

Val Phe Phe Asp Ile Asn Met Lys Gly Leu Asp Gly Ile Gln Gly Pro
            690                 695                 700

Ile Tyr Val Gly Thr Gly Cys Val Phe Arg Arg Gln Ala Leu Tyr Gly
705                 710                 715                 720

Tyr Asp Ala Pro Lys Thr Lys Lys Pro Ser Arg Thr Cys Asn Cys
                    725                 730                 735

Trp Pro Lys Trp Cys Leu Ser Cys Cys Cys Ser Arg Asn Lys Asn Lys
            740                 745                 750

Lys Lys Thr Thr Lys Pro Lys Thr Glu Lys Lys Arg Leu Phe Phe
            755                 760                 765

Lys Lys Ala Glu Asn Pro Ser Pro Ala Tyr Ala Leu Gly Glu Ile Asp
770                 775                 780

Glu Gly Ala Pro Gly Ala Asp Ile Glu Lys Ala Gly Ile Val Asn Gln
785                 790                 795                 800

Gln Lys Leu Glu Lys Lys Phe Gly Gln Ser Ser Val Phe Val Ala Ser
                    805                 810                 815

Thr Leu Leu Glu Asn Gly Gly Thr Leu Lys Ser Ala Ser Pro Ala Ser
            820                 825                 830

Leu Leu Lys Glu Ala Ile His Val Ile Ser Cys Gly Tyr Glu Asp Lys
            835                 840                 845

Thr Asp Trp Gly Lys Glu Ile Gly Trp Ile Tyr Gly Ser Ile Thr Glu
850                 855                 860

Asp Ile Leu Thr Gly Phe Lys Met His Cys His Gly Trp Arg Ser Ile
865                 870                 875                 880

Tyr Cys Ile Pro Lys Arg Pro Ala Phe Lys Gly Ser Ala Pro Leu Asn
                    885                 890                 895

Leu Ser Asp Arg Leu His Gln Val Leu Arg Trp Ala Leu Gly Ser Val
            900                 905                 910

Glu Ile Phe Phe Ser Lys His Cys Pro Leu Trp Tyr Gly Tyr Gly Gly
            915                 920                 925

Gly Leu Lys Phe Leu Glu Arg Phe Ser Tyr Ile Asn Ser Ile Val Tyr
            930                 935                 940

Pro Trp Thr Ser Ile Pro Leu Leu Ala Tyr Cys Thr Leu Pro Ala Ile
945                 950                 955                 960

Cys Leu Leu Thr Gly Lys Phe Ile Thr Pro Glu Leu Thr Asn Val Ala
                    965                 970                 975

Ser Ile Trp Phe Met Ala Leu Phe Ile Cys Ile Ser Val Thr Gly Ile
            980                 985                 990

Leu Glu Met Arg Trp Ser Gly Val Ala Ile Asp Asp Trp Trp Arg Asn
```

-continued

Glu Gln Phe Trp Val Ile Gly Gly Val Ser Ala His Leu Phe Ala Val
995              1000                 1005
                1010                1015              1020

Phe Gln Gly Leu Leu Lys Val Phe Ala Gly Ile Asp Thr Ser Phe Thr
1025             1030                1035              1040

Val Thr Ser Lys Ala Gly Asp Asp Glu Glu Phe Ser Glu Leu Tyr Thr
                1045                1050              1055

Phe Lys Trp Thr Thr Leu Leu Ile Pro Pro Thr Leu Leu Leu Leu
             1060                1065              1070

Asn Phe Ile Gly Val Val Ala Gly Ile Ser Asn Ala Ile Asn Asn Gly
                1075                1080              1085

Tyr Glu Ser Trp Gly Pro Leu Phe Gly Lys Leu Phe Ala Phe Trp
         1090                1095              1100

Val Ile Val His Leu Tyr Pro Phe Leu Lys Gly Leu Val Gly Arg Gln
1105             1110                1115              1120

Asn Arg Thr Pro Thr Ile Val Ile Val Trp Ser Ile Leu Leu Ala Ser
                1125                1130              1135

Ile Phe Ser Leu Leu Trp Val Arg Val Asp Pro Phe Leu Ala Lys Ser
         1140                1145              1150

Asn Gly Pro Leu Leu Glu Glu Cys Gly Leu Asp Cys Asn
         1155                1160              1165

<210> SEQ ID NO 9
<211> LENGTH: 3936
<212> TYPE: DNA
<213> ORGANISM: Zea mays

<400> SEQUENCE: 9
cttctccctc gtcggtgcgg cgtggcgcgg ctcggcgttc ggtgagaaac cactcggggg      60
atgaggatct gctgctagag tgagaggagc tacggtcagt atcctctgcc ttcgtcggcg     120
gcggaagtgg aggggaggaa gcgatggagg cgagcgccgg gctggtggcc ggctcccaca     180
accgcaacga gctcgtcgtc atccgccgcg acggcgatcc cgggccgaag ccgccgcggg     240
agcagaacgg gcaggtgtgc cagatttgcg gcgacgacgt cggccttgcc cccggcgggg     300
accccttcgt ggcgtgcaac gagtgcgcct tccccgtctg ccgggactgc tacgaatacg     360
agcgccggga gggcacgcag aactgccccc agtgcaagac tcgatacaag cgcctcaagg     420
gctgccaacg tgtgaccggt gacgaggagg aggacggcgt cgatgacctg acaacgagt     480
tcaactggga cggccatgac tcgcagtctg tggccgagtc catgctctac ggccacatga     540
gctacgccg tggaggtgac cctaatggcg cgccacaagc tttccagctc aaccccaatg     600
ttccactcct caccaacggg caaatggtgg atgacatccc accggagcag cacgcgctgg     660
tgccttcttt catgggtggt gggggaaaga ggatacatcc ccttccttat gcggatccca     720
gcttacctgt gcaacccagg tctatggacc catccaagga tcttgctgca tatgggtatg     780
gtagtgttgc ttggaaggaa cggatggaga attggaagca gagacaagag aggatgcacc     840
agacggggaa tgatggtggt ggtgatgatg gtgacgatgc tgatctacca ctaatggatg     900
aagcaagaca caactgtcc aggaaaattc cacttccatc aagccagatt aatccatata     960
ggatgattat cattattcgg cttgtggttt tgggggttctt cttccactac cgagtgatgc    1020
atccggtgaa tgatgcattt gctttgtggc tcatatctgt tatctgtgaa atctggtttg    1080
ccatgtcttg gattcttgat caattcccaa agtggttccc tattgagaga gagacttacc    1140
tagaccggct gtcactgagg ttcgacaagg aaggccagcc atctcaactt gctccaattg    1200

-continued

```
atttctttgt cagtacggtt gatcccttaa aggaacctcc tttggtcaca acaaatactg    1260
ttctatctat cctttcggtg gattatcctg ttgataaggt ttcttgctat gtttctgatg    1320
atggtgctgc aatgctaacg tttgaagcat tatctgaaac atctgaattt gcaaagaaat    1380
gggttccttt ctgcaaacgg tacaatattg aacctcgcgc tccagagtgg tacttccaac    1440
agaagataga ctacttgaaa gacaaggtgg cagcaaactt tgttagggag aggagagcaa    1500
tgaagagaga gtatgaggaa ttcaaggtga gaatcaatgc cttagttgcc aaagcccaga    1560
aagttcctga agaaggatgg acaatgcaag atggaacccc ctggcctgga aacaatgttc    1620
gtgatcatcc tggaatgatt caggtcttcc ttggccaaag cggaggcctt gactgtgagg    1680
gaaatgaact gccacgattg gtttatgttt ctagagagaa acgaccaggc tataaccatc    1740
ataagaaagc tggtgctatg aatgcattgg tccgagtctc tgctgtacta acaaatgctc    1800
catatttgtt aaacttggat tgtgatcact acatcaacaa cagcaaggct ataaaggaag    1860
caatgtgttt tatgatggac cctttactag gaaagaaggt ttgctatgta cagttccctc    1920
aaagatttga tgggattgat cgccatgacc gatatgctaa ccggaatgtt gtcttttttg    1980
atatcaacat gaaaggtttg gatggtattc agggtccaat ttatgttggt actggatgtg    2040
tatttagaag gcaggcatta tatggttatg atgcccccaa acaaagaag ccaccatcaa     2100 ggacttgcaa ctgctggccc aagtggtgct tttgctgttg ctgctttggc aataggaagc    2160
aaaagaagac taccaaaccc aaaacagaga agaaaaagtt attatttttc aagaaagaag    2220
agaaccaatc ccctgcatat gctcttggtg aaattgacga agctgctcca ggagctgaga    2280
atgaaaaggc cggtattgta aatcaacaaa aattagaaaa gaaatttggc caatcttctg    2340
tttttgttac atccacactt ctcgagaatg gtggaacctt gaagagtgca agtcctgctt    2400
ctcttttgaa agaagctata catgtcatta gttgtggtta tgaagacaag acagactggg    2460
gaaaagagat tggctggatc tatggatcag ttacagaaga tattctaact ggtttcaaga    2520
tgcattgtca tggttggcgg tcaatttact gcatacctaa acgggttgca ttcaaaggtt    2580
ctgcacctct gaatctttca gatcgtcttc accaggtgct tcgtgggct cttgggtcta     2640 ttgagatctt cttcagcaat cattgccctc tttggtatgg gtatggtggc ggtctgaaat    2700 tttttggaaag atttcctac atcaactcca tcgtgtatcc ttggacatct attcccctct    2760
tggcttactg tacattgcct gccatctgtt tattgacagg gaaatttatc actccagagc    2820
tgaataatgt tgccagcctg tggttcatgt cactttttat ctgcattttt gctacgagca    2880
tcctagaaat gagatggagt ggtgttggaa ttgatgactg gtggaggaat gagcagttct    2940
gggtcattgg aggtgtgtcc tcacacctct tgctgtgtt ccagggactt ctcaaggtca     3000
tagctggtgt tgatacaagc ttcaccgtga catcaaaggg tggagatgat gaggagttct    3060
cagagctata tacattcaaa tggactacct tattgatacc tcctaccacc ttgcttctat    3120
tgaacttcat tggtgtggtc gctggcgttt caaatgcgat caataacgga tatgagtcat    3180 ggggcccct ctttgggaag ctattctttg cattttgggt gattgtccat ctttatccct     3240
ttctcaaagg tttggttgga aggcaaaaca ggacaccaac gattgtcatc gtctggtcca    3300
ttctgctggc ttcaatcttc tcgctccttt gggttcggat tgatcctttc cttgcgaagg    3360
atgatggtcc gcttcttgag gagtgtggtt tggattgcaa ctaggatgtc agtgcatcag    3420 ctccccccaat ctgcatatgc ttgaagtata ttttctggtg tttgtcccca tattcagtgt    3480
ctgtagataa gagacatgaa atgtcccaag tttcttttga tccatggtga acctacttaa    3540
```

-continued

```
tatctgagag atatactggg ggaaaatgga ggctgcggca atccttgtgc agttgggccg    3600
tggaatacag catatgcaag tgtttgattg tgcagcattc tttattactt ggtcgcaata    3660
tagatgggct gagccgaaca gcaaggtatt ttgattctgc actgctcccg tgtacaaact    3720
tggttctcaa taaggcaggc aggaatgcat ctgccagtgg aacagagcaa cctgcacatt    3780
atttatgtat gcctgttcat tggagggctt gttcattaca tgttcgtcta tactagaaaa    3840
aacagaatat tagcattaat ctatagttaa ttaaagtatg taaatgcgcc tgttttttgt    3900
tgtgtactgt aatcatctga gttggttttg tgaaaa                              3936
```

<210> SEQ ID NO 10
<211> LENGTH: 1086
<212> TYPE: PRT
<213> ORGANISM: Zea mays

<400> SEQUENCE: 10

```
Met Glu Ala Ser Ala Gly Leu Val Ala Gly Ser His Asn Arg Asn Glu
 1               5                  10                  15

Leu Val Val Ile Arg Arg Asp Gly Asp Pro Gly Lys Pro Pro Arg
             20                  25                  30

Glu Gln Asn Gly Gln Val Cys Gln Ile Cys Gly Asp Val Gly Leu
         35                  40                  45

Ala Pro Gly Gly Asp Pro Phe Val Ala Cys Asn Glu Cys Ala Phe Pro
     50                  55                  60

Val Cys Arg Asp Cys Tyr Glu Tyr Glu Arg Arg Glu Gly Thr Gln Asn
 65                  70                  75                  80

Cys Pro Gln Cys Lys Thr Arg Tyr Lys Arg Leu Lys Gly Cys Gln Arg
                 85                  90                  95

Val Thr Gly Asp Glu Glu Glu Asp Gly Val Asp Asp Leu Asp Asn Glu
            100                 105                 110

Phe Asn Trp Asp Gly His Asp Ser Gln Ser Val Ala Glu Ser Met Leu
        115                 120                 125

Tyr Gly His Met Ser Tyr Gly Arg Gly Gly Asp Pro Asn Gly Ala Pro
    130                 135                 140

Gln Ala Phe Gln Leu Asn Pro Asn Val Pro Leu Leu Thr Asn Gly Gln
145                 150                 155                 160

Met Val Asp Asp Ile Pro Pro Glu Gln His Ala Leu Val Pro Ser Phe
                165                 170                 175

Met Gly Gly Gly Gly Lys Arg Ile His Pro Leu Pro Tyr Ala Asp Pro
            180                 185                 190

Ser Leu Pro Val Gln Pro Arg Ser Met Asp Pro Ser Lys Asp Leu Ala
        195                 200                 205

Ala Tyr Gly Tyr Gly Ser Val Ala Trp Lys Glu Arg Met Glu Asn Trp
    210                 215                 220

Lys Gln Arg Gln Glu Arg Met His Gln Thr Gly Asn Asp Gly Gly Gly
225                 230                 235                 240

Asp Asp Gly Asp Asp Ala Asp Leu Pro Leu Met Asp Glu Ala Arg Gln
                245                 250                 255

Gln Leu Ser Arg Lys Ile Pro Leu Pro Ser Ser Gln Ile Asn Pro Tyr
            260                 265                 270

Arg Met Ile Ile Ile Arg Leu Val Val Leu Gly Phe Phe His
        275                 280                 285

Tyr Arg Val Met His Pro Val Asn Asp Ala Phe Ala Leu Trp Leu Ile
    290                 295                 300
```

```
Ser Val Ile Cys Glu Ile Trp Phe Ala Met Ser Trp Ile Leu Asp Gln
305                 310                 315                 320

Phe Pro Lys Trp Phe Pro Ile Glu Arg Glu Thr Tyr Leu Asp Arg Leu
            325                 330                 335

Ser Leu Arg Phe Asp Lys Glu Gly Gln Pro Ser Gln Leu Ala Pro Ile
                340                 345                 350

Asp Phe Phe Val Ser Thr Val Asp Pro Leu Lys Glu Pro Pro Leu Val
            355                 360                 365

Thr Thr Asn Thr Val Leu Ser Ile Leu Ser Val Asp Tyr Pro Val Asp
        370                 375                 380

Lys Val Ser Cys Tyr Val Ser Asp Asp Gly Ala Ala Met Leu Thr Phe
385                 390                 395                 400

Glu Ala Leu Ser Glu Thr Ser Glu Phe Ala Lys Lys Trp Val Pro Phe
                405                 410                 415

Cys Lys Arg Tyr Asn Ile Glu Pro Arg Ala Pro Glu Trp Tyr Phe Gln
                420                 425                 430

Gln Lys Ile Asp Tyr Leu Lys Asp Lys Val Ala Ala Asn Phe Val Arg
            435                 440                 445

Glu Arg Arg Ala Met Lys Arg Glu Tyr Glu Glu Phe Lys Val Arg Ile
    450                 455                 460

Asn Ala Leu Val Ala Lys Ala Gln Lys Val Pro Glu Glu Gly Trp Thr
465                 470                 475                 480

Met Gln Asp Gly Thr Pro Trp Pro Gly Asn Asn Val Arg Asp His Pro
                485                 490                 495

Gly Met Ile Gln Val Phe Leu Gly Gln Ser Gly Gly Leu Asp Cys Glu
                500                 505                 510

Gly Asn Glu Leu Pro Arg Leu Val Tyr Val Ser Arg Glu Lys Arg Pro
            515                 520                 525

Gly Tyr Asn His His Lys Lys Ala Gly Ala Met Asn Ala Leu Val Arg
    530                 535                 540

Val Ser Ala Val Leu Thr Asn Ala Pro Tyr Leu Leu Asn Leu Asp Cys
545                 550                 555                 560

Asp His Tyr Ile Asn Asn Ser Lys Ala Ile Lys Glu Ala Met Cys Phe
                565                 570                 575

Met Met Asp Pro Leu Leu Gly Lys Lys Val Cys Tyr Val Gln Phe Pro
                580                 585                 590

Gln Arg Phe Asp Gly Ile Asp Arg His Asp Arg Tyr Ala Asn Arg Asn
            595                 600                 605

Val Val Phe Phe Asp Ile Asn Met Lys Gly Leu Asp Gly Ile Gln Gly
    610                 615                 620

Pro Ile Tyr Val Gly Thr Gly Cys Val Phe Arg Arg Gln Ala Leu Tyr
625                 630                 635                 640

Gly Tyr Asp Ala Pro Lys Thr Lys Lys Pro Pro Ser Arg Thr Cys Asn
                645                 650                 655

Cys Trp Pro Lys Trp Cys Phe Cys Cys Cys Phe Gly Asn Arg Lys
                660                 665                 670

Gln Lys Lys Thr Thr Lys Pro Lys Thr Glu Lys Lys Lys Leu Leu Phe
            675                 680                 685

Phe Lys Lys Glu Glu Asn Gln Ser Pro Ala Tyr Ala Leu Gly Glu Ile
    690                 695                 700

Asp Glu Ala Ala Pro Gly Ala Glu Asn Glu Lys Ala Gly Ile Val Asn
705                 710                 715                 720

Gln Gln Lys Leu Glu Lys Lys Phe Gly Gln Ser Ser Val Phe Val Thr
```

-continued

```
                725                 730                 735
Ser Thr Leu Leu Glu Asn Gly Gly Thr Lys Ser Ala Ser Pro Ala
                740                 745                 750

Ser Leu Leu Lys Glu Ala Ile His Val Ile Ser Cys Gly Tyr Glu Asp
                755                 760                 765

Lys Thr Asp Trp Gly Lys Glu Ile Gly Trp Ile Tyr Gly Ser Val Thr
                770                 775                 780

Glu Asp Ile Leu Thr Gly Phe Lys Met His Cys His Gly Trp Arg Ser
785                 790                 795                 800

Ile Tyr Cys Ile Pro Lys Arg Val Ala Phe Lys Gly Ser Ala Pro Leu
                805                 810                 815

Asn Leu Ser Asp Arg Leu His Gln Val Leu Arg Trp Ala Leu Gly Ser
                820                 825                 830

Ile Glu Ile Phe Phe Ser Asn His Cys Pro Leu Trp Tyr Gly Tyr Gly
                835                 840                 845

Gly Gly Leu Lys Phe Leu Glu Arg Phe Ser Tyr Ile Asn Ser Ile Val
                850                 855                 860

Tyr Pro Trp Thr Ser Ile Pro Leu Leu Ala Tyr Cys Thr Leu Pro Ala
865                 870                 875                 880

Ile Cys Leu Leu Thr Gly Lys Phe Ile Thr Pro Glu Leu Asn Asn Val
                885                 890                 895

Ala Ser Leu Trp Phe Met Ser Leu Phe Ile Cys Ile Phe Ala Thr Ser
                900                 905                 910

Ile Leu Glu Met Arg Trp Ser Gly Val Gly Ile Asp Asp Trp Trp Arg
                915                 920                 925

Asn Glu Gln Phe Trp Val Ile Gly Gly Val Ser Ser His Leu Phe Ala
                930                 935                 940

Val Phe Gln Gly Leu Leu Lys Val Ile Ala Gly Val Asp Thr Ser Phe
945                 950                 955                 960

Thr Val Thr Ser Lys Gly Gly Asp Asp Glu Glu Phe Ser Glu Leu Tyr
                965                 970                 975

Thr Phe Lys Trp Thr Thr Leu Leu Ile Pro Pro Thr Thr Leu Leu Leu
                980                 985                 990

Leu Asn Phe Ile Gly Val Val Ala Gly Val Ser Asn Ala Ile Asn Asn
                995                 1000                1005

Gly Tyr Glu Ser Trp Gly Pro Leu Phe Gly Lys Leu Phe Phe Ala Phe
                1010                1015                1020

Trp Val Ile Val His Leu Tyr Pro Phe Leu Lys Gly Leu Val Gly Arg
1025                1030                1035                1040

Gln Asn Arg Thr Pro Thr Ile Val Ile Val Trp Ser Ile Leu Leu Ala
                1045                1050                1055

Ser Ile Phe Ser Leu Leu Trp Val Arg Ile Asp Pro Phe Leu Ala Lys
                1060                1065                1070

Asp Asp Gly Pro Leu Leu Glu Glu Cys Gly Leu Asp Cys Asn
                1075                1080                1085
```

<210> SEQ ID NO 11
<211> LENGTH: 1138
<212> TYPE: DNA
<213> ORGANISM: Oryza sativa

<400> SEQUENCE: 11

```
cgctgctccc ggcgatggac gtgttcgtca ccaccgccga ccccgacaag gagccgccgc      60
tcgccacggc gaacaccgtg ctgtccatat atcctcgccg cgggctaccc cgccggcaag    120
```

-continued

```
gtgacgtgct atatttccga cgacgcaggc gcggaggtga cacgtaacgc ggtcgtggag    180
gcggcccggt tcgcggcgct ttgggtgtcg ttctgccgga agcacggcgt cgagccgagg    240
aacctggagg cgtacttcaa cgccggcgag ggtggtggtg gcaaggcgaa ggtggtggcg    300
agggggagct acaggggggat ggcgtggccg gagctggtgc gcgacaggag acgggtgcgc    360
cgcgagtacg aggagatgcg gctgcggatc gacgcgctgc aggccgccga tgcgcgccgc    420
cggcgccgcg gcgcggccga tgaccacgcc ggagttgtgc aggtactgat cgattttgct    480
gggagcgtgc cacagctcgg cgttgcgaac gggagcaagc tcatcgacgt cgcctctgtc    540
gacgtgtgcc tcccggcgct tgtgtacgtg tgccgcgaga gcgccgcgg ccacgcgcac    600 caccggaagg cgggcgccat gaacgcgccc ttcatcctcg acctcgactg cgactactac    660
gtcaacaact cgcaggccct ccgcgccggc atctgcttca tgatcgaacg cggcggcggc    720
ggagccgccg aagacgccgg cgcggtcgcg ttcgtccagt tcccgcagcg ggtcgacggc    780
gtcgatcccg gcgaccgcta cgccaaccac aaccgcgtcc tcttcgactg caccgagctc    840
ggcctcgacg gcctccaggg ccccatctac gtcggcaccg gctgcttgtt ccgccgtgtc    900
gcgctctaca gcgtcgacct gccgcgctgg agaccgcggc gttcattggg ctgtcgccta    960
ctcggagaag acgagcggct atggtccagg atgaaacaaa tggtaatatt aagtggtcca   1020
aggtgaaaaa ctcagctaaa acctgaccca agctgtaaca tgggtaaaaa tatatggccc   1080
aaaatgaaat ttactttttt tttttacca aaaaaaaaaa aaaaaaaaaa aaaaaaa      1138
```

<210> SEQ ID NO 12
<211> LENGTH: 341
<212> TYPE: PRT
<213> ORGANISM: Oryza sativa

<400> SEQUENCE: 12

```
Arg Cys Ser Arg Arg Trp Thr Cys Ser Ser Pro Pro Thr Pro Thr
  1               5                  10                  15

Arg Ser Arg Arg Ser Pro Arg Arg Thr Pro Cys Cys Pro Tyr Ile Leu
                 20                  25                  30

Ala Ala Gly Tyr Pro Ala Gly Lys Val Thr Cys Tyr Ile Ser Asp Asp
             35                  40                  45

Ala Gly Ala Glu Val Thr Arg Asn Ala Val Glu Ala Ala Arg Phe
         50                  55                  60

Ala Ala Leu Trp Val Ser Phe Cys Arg Lys His Gly Val Glu Pro Arg
 65                  70                  75                  80

Asn Leu Glu Ala Tyr Phe Asn Ala Gly Glu Gly Gly Gly Lys Ala
                 85                  90                  95

Lys Val Val Ala Arg Gly Ser Tyr Arg Gly Met Ala Trp Pro Glu Leu
            100                 105                 110

Val Arg Asp Arg Arg Val Arg Glu Tyr Glu Glu Met Arg Leu
            115                 120                 125

Arg Ile Asp Ala Leu Gln Ala Ala Asp Ala Arg Arg Arg Arg Gly
        130                 135                 140

Ala Ala Asp Asp His Ala Gly Val Val Gln Val Leu Ile Asp Phe Ala
145                 150                 155                 160

Gly Ser Val Pro Gln Leu Gly Val Ala Asn Gly Ser Lys Leu Ile Asp
                165                 170                 175

Val Ala Ser Val Asp Val Cys Leu Pro Ala Leu Val Tyr Val Cys Arg
            180                 185                 190
```

-continued

```
Glu Lys Arg Arg Gly His Ala His His Arg Lys Ala Gly Ala Met Asn
            195                 200                 205
Ala Pro Phe Ile Leu Asp Leu Asp Cys Asp Tyr Tyr Val Asn Asn Ser
        210                 215                 220
Gln Ala Leu Arg Ala Gly Ile Cys Phe Met Ile Glu Arg Gly Gly Gly
225                 230                 235                 240
Gly Ala Ala Glu Asp Ala Gly Ala Val Ala Phe Val Gln Phe Pro Gln
                245                 250                 255
Arg Val Asp Gly Val Asp Pro Gly Asp Arg Tyr Ala Asn His Asn Arg
            260                 265                 270
Val Leu Phe Asp Cys Thr Glu Leu Gly Leu Asp Gly Leu Gln Gly Pro
        275                 280                 285
Ile Tyr Val Gly Thr Gly Cys Leu Phe Arg Arg Val Ala Leu Tyr Ser
290                 295                 300
Val Asp Leu Pro Arg Trp Arg Pro Arg Arg Ser Leu Gly Cys Arg Leu
305                 310                 315                 320
Leu Gly Glu Asp Glu Arg Leu Trp Ser Arg Met Lys Gln Met Val Ile
                325                 330                 335
Leu Ser Gly Pro Arg
            340

<210> SEQ ID NO 13
<211> LENGTH: 3517
<212> TYPE: DNA
<213> ORGANISM: Glycine max

<400> SEQUENCE: 13
gcacgagcca acaacaacac ccttatgtgg acacattagg tgaggttcaa cagctagcac      60
caatcttcct tcataaaaca caaacctttg atcacacaat ctcaccttaa tttgtgttgt     120
tgttgtgcca ttcccatatt gtcccattca ctaagacatg gaagccagcg ctggactggt     180
cgctgggtca cataaccgca atgagctagt tgtcattcat ggccatgaag agccgaaggc     240
tttgaagaac ttggatgggc aagtgtgtga gatttgtggt gatggcgtgg gactcacggt     300
ggatggagac ttgtttgtgg cttgcaatga gtgtggtttt ccagtgtgca ggccttgcta     360
tgagtatgaa aggagagaag gaagccacct ttgcccacag tgcaaaacca gatacaagcg     420
tctcaaaggg agcccccgag tggagggaga tgatgatgaa gaggatgtgg atgatattga     480
gcatgaattc aatattgatg agcaaaagaa caagcatggc caggttgcag aagccatgct     540
tcatgggagg atgagctatg aagaggtcc tgaagatgat acaattccc agttcccaac       600
acctgtcatt gctggtggtc gttctaggcc tgtaagtggg gagttcccaa tatcatctaa     660
tgcttatggg gatcagatgt tatcctcttc actgcataaa agagtgcatc catatccagt     720
gtctgaacct ggaagtgcaa gatgggacga aaaaaaaga gatggatgg aaagatagaa       780
tggatgactg gaaattgcag caaggcaatt ggggcctga accggatgaa gatccagatg      840
cagccatgtt agatgaagca aggcaaccac tgtcaaggaa agtgccaata gcatccagca     900
aaatcaatcc atatagaatg gtgattgtgg cacgtctggt tattcttgct tcttcctca      960
gatacagact catgaaccca gtacatgatg ccctggggct atggctaacc tctatcatat    1020
gtgaaatctg gtttgctttt tcatggattc tggatcagtt tcccaaatgg tttcccattg    1080
atagagagac ctaccttgac cgtctttcca tcaggtatga gcgtgaaggt gaaccaaaca    1140
tgcttgctcc tgtagatgtt tttgttagta ccgtggatcc catgaaggaa cctcctctgg    1200
ttacagcaaa cactgttctt tcaatcttgg ccatggatta cccggttgat aaaatatcat    1260
```

-continued

```
gctacatttc tgatgatgga gcctcaatgt gtacatttga gtccttatca gaaactgcag    1320
agtttgctag aaagtgggta ccgttttgta agaaattttc catagaacct cgggcacctg    1380
agatgtactt cagcgagaag attgactacc taaaggacaa agtgcaaccc acctttgtta    1440
aggagcgtcg agctatgaag agggaatacg aagagtttaa ggttaggatc aatgcacttg    1500
ttgctaaggc ccagaaagtt cctcagggag atggatcat gcaggatggg acaccatggc    1560
cagggaataa cactaaggat catcctggta tgattcaagt gtttcttggt agcagtggag    1620
gtcttgatac tgaaggaaac caacttcctc gccttgttta tgtttccaga gagaaaaggc    1680
ctggttttca acaccacaag aaagctggtg ccatgaatgc tctggttcgg gtatctgctg    1740
ttctcacaaa tgctcctttc atgttgaact tggattgtga tcactatgtc aataacagca    1800
aggctgcccg agaggccatg tgcttcttga tggacccaca aactgggaag aaggtctgct    1860
atgtccagtt tcctcaaaga tttgatggta ttgatacaca tgatcgttat gccaacagga    1920
acacagtttt ctttgatatt aacatgaagg gtctagatgg tattcaaggt cctgtatatg    1980
tggggactgg atgtgttttc aggaggcaag ctttgtatgg ctataatcct cccaagggtc    2040
caaagcgtcc aaaaatggta agctgtgatt gttgcccgtg ttttggaagc cgcaagaagt    2100
ataaggagaa gaatgatgca aatggagagg ctgcaagcct aaaagggatg gatgatgaca    2160
aagaggtgtt gatgtcccaa atgaattttg agaagaaatt tggacaatcc tctattttg     2220 tgacttctac cttgatgaa gagggtggtg tgcctccttc ttcaagtcca gctgccctgc    2280
ttaaagaagc cattcatgtg attagctgtg gatatgaaga taaaactgaa tggggacttg    2340
agcttggttg gatctatgga tctatcacag aagatattct aacaggtttt aagatgcatt    2400
gccgtgggtg gaggtccatt tattgtatgc caaagagagc tgcattcaag gtactgctc     2460 ctatcaactt gtcagatcgt ctcaaccagg ttcttcgttg ggcacttggt tccattgaga    2520 tttttctttag tcaccattgc cctctatggt atggcttcaa ggaaaagaag ctaaagtggc    2580
ttgagagatt tgcctatgca aacacaactg tctatccatt cacctccatt cctctagttg    2640
cctactgtat tcttccagca gttttgtttac tcactgacaa attcatcatg ccaccgatta    2700
gcacctttgc tggtttgtac tttgttgctc tcttctcctc aatcattgca actggtattc    2760
ttgagttgaa atggagtgga gtgagcattg aggaatggtg gagaaatgag cagttttggg    2820
tcattggtgg tgtatcagct cacctctttg ctgttataca aggtctgcta aaggttctgg    2880
ctggaattga caccaatttc actgttacat caaaggcaac agatgatgaa gagtttggag    2940
aattgtacac ctttaagtgg actacactct tgattcctcc aaccactatt ttgatcatta    3000
acattgttgg tgttgttgct ggaatctcag atgccataaa caatgggtac caatcctggg    3060
gaccactctt tggaaagctc ttcttttcct tctgggtgat tgtccatctc tatccattcc    3120
ttaaaggttt gatgggtcgc caaaatcgca cacccaccat tgttgtgatt tggtcagtgc    3180
tattggcctc tattttctcc ttactttggg taagaattga tccatttgtc ctcaagacta    3240
agggacctga taccaagcta tgtggaatca actgctaaaa aagactgctt tccctatagt    3300
attattcttt aaaagatgta tgtagggtac atacattctt ggtttcacaa accaacaaag    3360 tgcaatgca caaggatcaa taaggaaaga gtgaaaattt tgtgtatcat aaatgagtgt    3420 tatcatttt gtaaatgttc tcaaggacat ctgttttggt tggaactgcc caaaaattgc    3480
agttttatct attcactgga aaaaaaaaa aaaaaaa                              3517
```

<210> SEQ ID NO 14

```
<211> LENGTH: 1039
<212> TYPE: PRT
<213> ORGANISM: Glycine max
<220> FEATURE:
<221> NAME/KEY: UNSURE
<222> LOCATION: (201)

<400> SEQUENCE: 14
```

| | | | | | | | | | | | | | | |
|---|---|---|---|---|---|---|---|---|---|---|---|---|---|---|
| Met | Glu | Ala | Ser | Ala | Gly | Leu | Val | Ala | Gly | Ser | His | Asn | Arg | Asn | Glu |
| 1 | | | | 5 | | | | | 10 | | | | | 15 | |
| Leu | Val | Val | Ile | His | Gly | His | Glu | Glu | Pro | Lys | Ala | Leu | Lys | Asn | Leu |
| | | | | 20 | | | | | 25 | | | | | 30 | |
| Asp | Gly | Gln | Val | Cys | Glu | Ile | Cys | Gly | Asp | Gly | Val | Gly | Leu | Thr | Val |
| | | | 35 | | | | | 40 | | | | | 45 | | |
| Asp | Gly | Asp | Leu | Phe | Val | Ala | Cys | Asn | Glu | Cys | Gly | Phe | Pro | Val | Cys |
| | 50 | | | | | 55 | | | | | 60 | | | | |
| Arg | Pro | Cys | Tyr | Glu | Tyr | Glu | Arg | Arg | Glu | Gly | Ser | His | Leu | Cys | Pro |
| 65 | | | | | 70 | | | | | 75 | | | | | 80 |
| Gln | Cys | Lys | Thr | Arg | Tyr | Lys | Arg | Leu | Lys | Gly | Ser | Pro | Arg | Val | Glu |
| | | | | 85 | | | | | 90 | | | | | 95 | |
| Gly | Asp | Asp | Asp | Glu | Glu | Asp | Val | Asp | Asp | Ile | Glu | His | Glu | Phe | Asn |
| | | | | 100 | | | | | 105 | | | | | 110 | |
| Ile | Asp | Glu | Gln | Lys | Asn | Lys | His | Gly | Gln | Val | Ala | Glu | Ala | Met | Leu |
| | | | 115 | | | | | 120 | | | | | 125 | | |
| His | Gly | Arg | Met | Ser | Tyr | Gly | Arg | Gly | Pro | Glu | Asp | Asp | Asp | Asn | Ser |
| | 130 | | | | | 135 | | | | | 140 | | | | |
| Gln | Phe | Pro | Thr | Pro | Val | Ile | Ala | Gly | Gly | Arg | Ser | Arg | Pro | Val | Ser |
| 145 | | | | | 150 | | | | | 155 | | | | | 160 |
| Gly | Glu | Phe | Pro | Ile | Ser | Ser | Asn | Ala | Tyr | Gly | Asp | Gln | Met | Leu | Ser |
| | | | | 165 | | | | | 170 | | | | | 175 | |
| Ser | Ser | Leu | His | Lys | Arg | Val | His | Pro | Tyr | Pro | Val | Ser | Glu | Pro | Gly |
| | | | 180 | | | | | 185 | | | | | 190 | | |
| Ser | Ala | Arg | Trp | Asp | Glu | Lys | Lys | Xaa | Asp | Gly | Trp | Lys | Asp | Arg | Met |
| | | | 195 | | | | | 200 | | | | | 205 | | |
| Asp | Asp | Trp | Lys | Leu | Gln | Gln | Gly | Asn | Leu | Gly | Pro | Glu | Pro | Asp | Glu |
| | 210 | | | | | 215 | | | | | 220 | | | | |
| Asp | Pro | Asp | Ala | Ala | Met | Leu | Asp | Glu | Ala | Arg | Gln | Pro | Leu | Ser | Arg |
| 225 | | | | | 230 | | | | | 235 | | | | | 240 |
| Lys | Val | Pro | Ile | Ala | Ser | Ser | Lys | Ile | Asn | Pro | Tyr | Arg | Met | Val | Ile |
| | | | | 245 | | | | | 250 | | | | | 255 | |
| Val | Ala | Arg | Leu | Val | Ile | Leu | Ala | Phe | Phe | Leu | Arg | Tyr | Arg | Leu | Met |
| | | | 260 | | | | | 265 | | | | | 270 | | |
| Asn | Pro | Val | His | Asp | Ala | Leu | Gly | Leu | Trp | Leu | Thr | Ser | Ile | Ile | Cys |
| | | | | 275 | | | | | 280 | | | | | 285 | |
| Glu | Ile | Trp | Phe | Ala | Phe | Ser | Trp | Ile | Leu | Asp | Gln | Phe | Pro | Lys | Trp |
| | 290 | | | | | 295 | | | | | 300 | | | | |
| Phe | Pro | Ile | Asp | Arg | Glu | Thr | Tyr | Leu | Asp | Arg | Leu | Ser | Ile | Arg | Tyr |
| 305 | | | | | 310 | | | | | 315 | | | | | 320 |
| Glu | Arg | Glu | Gly | Glu | Pro | Asn | Met | Leu | Ala | Pro | Val | Asp | Val | Phe | Val |
| | | | | 325 | | | | | 330 | | | | | 335 | |
| Ser | Thr | Val | Asp | Pro | Met | Lys | Glu | Pro | Pro | Leu | Val | Thr | Ala | Asn | Thr |
| | | | 340 | | | | | 345 | | | | | 350 | | |
| Val | Leu | Ser | Ile | Leu | Ala | Met | Asp | Tyr | Pro | Val | Asp | Lys | Ile | Ser | Cys |
| | | | | 355 | | | | | 360 | | | | | 365 | |
| Tyr | Ile | Ser | Asp | Asp | Gly | Ala | Ser | Met | Cys | Thr | Phe | Glu | Ser | Leu | Ser |

-continued

```
        370                 375                 380
Glu Thr Ala Glu Phe Ala Arg Lys Trp Val Pro Phe Cys Lys Lys Phe
385                 390                 395                 400

Ser Ile Glu Pro Arg Ala Pro Glu Met Tyr Phe Ser Glu Lys Ile Asp
                405                 410                 415

Tyr Leu Lys Asp Lys Val Gln Pro Thr Phe Val Lys Glu Arg Arg Ala
                420                 425                 430

Met Lys Arg Glu Tyr Glu Phe Lys Val Arg Ile Asn Ala Leu Val
                435                 440                 445

Ala Lys Ala Gln Lys Val Pro Gln Gly Gly Trp Ile Met Gln Asp Gly
450                 455                 460

Thr Pro Trp Pro Gly Asn Asn Thr Lys Asp His Pro Gly Met Ile Gln
465                 470                 475                 480

Val Phe Leu Gly Ser Ser Gly Gly Leu Asp Thr Glu Gly Asn Gln Leu
                485                 490                 495

Pro Arg Leu Val Tyr Val Ser Arg Glu Lys Arg Pro Gly Phe Gln His
                500                 505                 510

His Lys Lys Ala Gly Ala Met Asn Ala Leu Val Arg Val Ser Ala Val
                515                 520                 525

Leu Thr Asn Ala Pro Phe Met Leu Asn Leu Asp Cys Asp His Tyr Val
530                 535                 540

Asn Asn Ser Lys Ala Ala Arg Glu Ala Met Cys Phe Leu Met Asp Pro
545                 550                 555                 560

Gln Thr Gly Lys Lys Val Cys Tyr Val Gln Phe Pro Gln Arg Phe Asp
                565                 570                 575

Gly Ile Asp Thr His Asp Arg Tyr Ala Asn Arg Asn Thr Val Phe Phe
                580                 585                 590

Asp Ile Asn Met Lys Gly Leu Asp Gly Ile Gln Gly Pro Val Tyr Val
                595                 600                 605

Gly Thr Gly Cys Val Phe Arg Arg Gln Ala Leu Tyr Gly Tyr Asn Pro
                610                 615                 620

Pro Lys Gly Pro Lys Arg Pro Lys Met Val Ser Cys Asp Cys Pro
625                 630                 635                 640

Cys Phe Gly Ser Arg Lys Lys Tyr Lys Glu Lys Asn Asp Ala Asn Gly
                645                 650                 655

Glu Ala Ala Ser Leu Lys Gly Met Asp Asp Lys Glu Val Leu Met
                660                 665                 670

Ser Gln Met Asn Phe Glu Lys Lys Phe Gly Gln Ser Ile Phe Val
                675                 680                 685

Thr Ser Thr Leu Met Glu Glu Gly Gly Val Pro Pro Ser Ser Ser Pro
690                 695                 700

Ala Ala Leu Leu Lys Glu Ala Ile His Val Ile Ser Cys Gly Tyr Glu
705                 710                 715                 720

Asp Lys Thr Glu Trp Gly Leu Glu Leu Gly Trp Ile Tyr Gly Ser Ile
                725                 730                 735

Thr Glu Asp Ile Leu Thr Gly Phe Lys Met His Cys Arg Gly Trp Arg
                740                 745                 750

Ser Ile Tyr Cys Met Pro Lys Arg Ala Ala Phe Lys Gly Thr Ala Pro
                755                 760                 765

Ile Asn Leu Ser Asp Arg Leu Asn Gln Val Leu Arg Trp Ala Leu Gly
                770                 775                 780

Ser Ile Glu Ile Phe Phe Ser His His Cys Pro Leu Trp Tyr Gly Phe
785                 790                 795                 800
```

-continued

```
Lys Glu Lys Lys Leu Lys Trp Leu Glu Arg Phe Ala Tyr Ala Asn Thr
                805                 810                 815
Thr Val Tyr Pro Phe Thr Ser Ile Pro Leu Val Ala Tyr Cys Ile Leu
            820                 825                 830
Pro Ala Val Cys Leu Leu Thr Asp Lys Phe Ile Met Pro Pro Ile Ser
            835                 840                 845
Thr Phe Ala Gly Leu Tyr Phe Val Ala Leu Phe Ser Ser Ile Ile Ala
            850                 855                 860
Thr Gly Ile Leu Glu Leu Lys Trp Ser Gly Val Ser Ile Glu Glu Trp
865                 870                 875                 880
Trp Arg Asn Glu Gln Phe Trp Val Ile Gly Val Ser Ala His Leu
                885                 890                 895
Phe Ala Val Ile Gln Gly Leu Leu Lys Val Leu Ala Gly Ile Asp Thr
                900                 905                 910
Asn Phe Thr Val Thr Ser Lys Ala Thr Asp Asp Glu Glu Phe Gly Glu
            915                 920                 925
Leu Tyr Thr Phe Lys Trp Thr Thr Leu Leu Ile Pro Pro Thr Thr Ile
            930                 935                 940
Leu Ile Ile Asn Ile Val Gly Val Val Ala Gly Ile Ser Asp Ala Ile
945                 950                 955                 960
Asn Asn Gly Tyr Gln Ser Trp Gly Pro Leu Phe Gly Lys Leu Phe Phe
                965                 970                 975
Ser Phe Trp Val Ile Val His Leu Tyr Pro Phe Leu Lys Gly Leu Met
                980                 985                 990
Gly Arg Gln Asn Arg Thr Pro Thr Ile Val Val Ile Trp Ser Val Leu
            995                 1000                1005
Leu Ala Ser Ile Phe Ser Leu Leu Trp Val Arg Ile Asp Pro Phe Val
            1010                1015                1020
Leu Lys Thr Lys Gly Pro Asp Thr Lys Leu Cys Gly Ile Asn Cys
1025                1030                1035
```

<210> SEQ ID NO 15
<211> LENGTH: 2125
<212> TYPE: DNA
<213> ORGANISM: Glycine max

<400> SEQUENCE: 15

```
gccaaagctc agaagatgcc agaggaaggt tggacaatgc aggatggaac tccttggcct    60
ggaaataatc ctagggatca tccgggaatg attcaggtgt ttttaggtca tagtgggggg   120
ctggatacag atggaaatga gctgcctaga cttgtttatg tttctcgtga agaagcgacca  180
ggcttccaac atcacaagaa ggctggagct atgaatgctt tgattcgagt ttctgctgtc   240
ttgaccaatg gtgcatatct tctgaatgtg gattgtgatc actatttcaa taatagcaaa   300
gccctcaaag aagccatgtg tttcatgatg atcctgttc ttggaaagaa acatgctat    360
gttcaatttc ctcagagatt tgacggcatt gacttgcacg atcgatatgc caatcgcaat   420
attgtgttct tgatatcaa catgaaaggt caggatggtg ttcagggccc agtctatgtg    480
ggaactggtt gttgtttcaa taggcaagct ttgtatggtt atgatcctgt tttgactgag   540
gaagatttgg aacctaacat tattgtaaag agttgttgcg ttctagaaa gaagggaaag    600
ggtggcaata agaagtacag tgacaagaag aaggcgatgg aagaactga atccactgta    660
cccatattta atatggaaga catagaggag ggtgttgaag gttatgatga tgaaaggaca   720
ctacttatgt ctcaaaagag cttggagaag cgttttggtc agtctccagt ttttattgct  780
```

-continued

```
gccactttca tggagcaggg tggcattcca ccttcaacga accctgcaac tcttcttaag    840
gaagcaatcc atgttatcag ctgtggttac gaagacaaga cagaatgggg caaagagatt    900
ggatggatct atggctctgt gacagaagat atcttgactg ggttcaagat gcatgctcgt    960
ggttggattt ccatctattg catgccacct cgcccagcat ttaagggttc tgctcctatc   1020
aatctttctg atcgtctcaa tcaggtgctt cggtgggcct tgggttcaat tgagatcttt   1080
ctaagcaggc attgtccctt gtggtatggc tacaatggga agttgaagcc tctgatgagg   1140
cttgcttata ttaacaccat tgtctacccg tttacctcaa tcccattgat tgcttactgt   1200
acgcttcctg cattttgtct tctcacaaat aaatttatta ttcctgagat aagcaacttt   1260
gccagtatgt ggttcattct tctctttgtc tccatttttta ccacttcaat tcttgagctt   1320
aggtggagtg gggtcagtat agaagactgg tggagaaatg aacagttctg ggttatcggt   1380
gggacatctg cgcatctctt tgctgtgttc caggggcttc taaaagtgct tgctgggatc   1440
gatacaaatt ttactgttac atcgaaggca tcggacgagg atggggactt tgccgagctt   1500
tatgtgttta aatggacatc acttctcatc cctcctacaa cagtgcttat tgtgaatttg   1560
gttgggattg tggctggtgt atcctatgcc ataaacagtg gttaccagtc ttggggtcca   1620
ctatttggca agctgttctt tgctatctgg gtcattgccc atctataccc attcttgaag   1680
ggtctcttgg gcaggcaaaa tcgtacccca accattgtta ttgtttggtc cgttcttctt   1740
gcttcaatat tctccttgct gtgggtgagg attgatccct tcacctctga ctccaacaaa   1800
ttaaccaatg gtcaatgtgg catcaactgt tagttctctt gtatgattca ttttgtgttg   1860
ttattccctt ttgcttggag atacacaagg ttgctgtcgt gtatatagca agaatttttca   1920
gcctatcaaa gttgtctgga ggattgaacc cctgaaatag atgggaatgt accctctctg   1980
tttctattat ttatctacat gttccttaca agaatagtca gtagtaatgt tgaggtgtat   2040
gttatatttt ttccccacag aatataaatt tgttcatgcg aatatttaat gaaagccaac   2100
aaggtcctgt gttgttttgt tcttt                                         2125
```

<210> SEQ ID NO 16
<211> LENGTH: 610
<212> TYPE: PRT
<213> ORGANISM: Glycine max

<400> SEQUENCE: 16

```
Ala Lys Ala Gln Lys Met Pro Glu Glu Gly Trp Thr Met Gln Asp Gly
 1               5                  10                  15

Thr Pro Trp Pro Gly Asn Asn Pro Arg Asp His Pro Gly Met Ile Gln
            20                  25                  30

Val Phe Leu Gly His Ser Gly Gly Leu Asp Thr Asp Gly Asn Glu Leu
        35                  40                  45

Pro Arg Leu Val Tyr Val Ser Arg Glu Lys Arg Pro Gly Phe Gln His
    50                  55                  60

His Lys Lys Ala Gly Ala Met Asn Ala Leu Ile Arg Val Ser Ala Val
65                  70                  75                  80

Leu Thr Asn Gly Ala Tyr Leu Leu Asn Val Asp Cys Asp His Tyr Phe
                85                  90                  95

Asn Asn Ser Lys Ala Leu Lys Glu Ala Met Cys Phe Met Met Asp Pro
            100                 105                 110

Val Leu Gly Lys Lys Thr Cys Tyr Val Gln Phe Pro Gln Arg Phe Asp
        115                 120                 125
```

-continued

```
Gly Ile Asp Leu His Asp Arg Tyr Ala Asn Arg Asn Ile Val Phe Phe
130                 135                 140

Asp Ile Asn Met Lys Gly Gln Asp Gly Val Gln Gly Pro Val Tyr Val
145                 150                 155                 160

Gly Thr Gly Cys Cys Phe Asn Arg Gln Ala Leu Tyr Gly Tyr Asp Pro
                165                 170                 175

Val Leu Thr Glu Glu Asp Leu Glu Pro Asn Ile Ile Val Lys Ser Cys
            180                 185                 190

Cys Gly Ser Arg Lys Lys Gly Lys Gly Asn Lys Lys Tyr Ser Asp
        195                 200                 205

Lys Lys Lys Ala Met Gly Arg Thr Glu Ser Thr Val Pro Ile Phe Asn
210                 215                 220

Met Glu Asp Ile Glu Glu Gly Val Glu Gly Tyr Asp Asp Glu Arg Thr
225                 230                 235                 240

Leu Leu Met Ser Gln Lys Ser Leu Glu Lys Arg Phe Gly Gln Ser Pro
                245                 250                 255

Val Phe Ile Ala Ala Thr Phe Met Glu Gln Gly Gly Ile Pro Pro Ser
            260                 265                 270

Thr Asn Pro Ala Thr Leu Leu Lys Glu Ala Ile His Val Ile Ser Cys
        275                 280                 285

Gly Tyr Glu Asp Lys Thr Glu Trp Gly Lys Glu Ile Gly Trp Ile Tyr
290                 295                 300

Gly Ser Val Thr Glu Asp Ile Leu Thr Gly Phe Lys Met His Ala Arg
305                 310                 315                 320

Gly Trp Ile Ser Ile Tyr Cys Met Pro Pro Arg Pro Ala Phe Lys Gly
                325                 330                 335

Ser Ala Pro Ile Asn Leu Ser Asp Arg Leu Asn Gln Val Leu Arg Trp
            340                 345                 350

Ala Leu Gly Ser Ile Glu Ile Phe Leu Ser Arg His Cys Pro Leu Trp
        355                 360                 365

Tyr Gly Tyr Asn Gly Lys Leu Lys Pro Leu Met Arg Leu Ala Tyr Ile
370                 375                 380

Asn Thr Ile Val Tyr Pro Phe Thr Ser Ile Pro Leu Ile Ala Tyr Cys
385                 390                 395                 400

Thr Leu Pro Ala Phe Cys Leu Leu Thr Asn Lys Phe Ile Ile Pro Glu
                405                 410                 415

Ile Ser Asn Phe Ala Ser Met Trp Phe Ile Leu Leu Phe Val Ser Ile
            420                 425                 430

Phe Thr Thr Ser Ile Leu Glu Leu Arg Trp Ser Gly Val Ser Ile Glu
        435                 440                 445

Asp Trp Trp Arg Asn Glu Gln Phe Trp Val Ile Gly Gly Thr Ser Ala
450                 455                 460

His Leu Phe Ala Val Phe Gln Gly Leu Leu Lys Val Leu Ala Gly Ile
465                 470                 475                 480

Asp Thr Asn Phe Thr Val Thr Ser Lys Ala Ser Asp Glu Asp Gly Asp
                485                 490                 495

Phe Ala Glu Leu Tyr Val Phe Lys Trp Thr Ser Leu Leu Ile Pro Pro
            500                 505                 510

Thr Thr Val Leu Ile Val Asn Leu Val Gly Ile Val Ala Gly Val Ser
        515                 520                 525

Tyr Ala Ile Asn Ser Gly Tyr Gln Ser Trp Gly Pro Leu Phe Gly Lys
530                 535                 540

Leu Phe Phe Ala Ile Trp Val Ile Ala His Leu Tyr Pro Phe Leu Lys
```

```
                    545                 550                 555                 560
Gly Leu Leu Gly Arg Gln Asn Arg Thr Pro Thr Ile Val Ile Val Trp
                565                 570                 575
Ser Val Leu Leu Ala Ser Ile Phe Ser Leu Leu Trp Val Arg Ile Asp
            580                 585                 590
Pro Phe Thr Ser Asp Ser Asn Lys Leu Thr Asn Gly Gln Cys Gly Ile
        595                 600                 605
Asn Cys
    610

<210> SEQ ID NO 17
<211> LENGTH: 2890
<212> TYPE: DNA
<213> ORGANISM: Glycine max

<400> SEQUENCE: 17
gcacgagctc cacccagtta atgatgcata tggcttgtgg ttgacatcag tcatctgtga      60
aatatggttt gctgtatcat ggataatgga tcagtttcca aaatggtacc caatacagcg     120
agaaacatac cttgatcgtc tgtcactcag gtatgaaaaa gaagggaagc catctgagtt     180
gtccagtgta gacgtctttg tcagtactgt tgatcccatg aaggaacctc cactgattac     240
agcaaacact gttctatcta tccttgctgt tgattatcca gttgataaag ttgcatgcta     300
tgtctcagat gatggtgctg ctatgcttac ttttgaagca ctgtctgaga catctgaatt     360
tgctaggaga tgggttccat tttgtaagaa atacaatatt gagccccggg caccagaatg     420
gtactttggt cagaagatgg actatctgaa aaataaagta cacccagcat tgtcaggga     480
aggagagca atgaagaggg attatgaaga atttaaggtg aggattaaca gtttggtggc     540
aacagcacaa aaggttcctg aggatggatg gaccatgcaa gatgggactc cttggcctgg     600
aaataatgtg agggatcatc ctggcatgat tcaggtcttc cttgggcagg atggtgttcg     660
tgatgttgaa ggaaatgagc tacccgcctt ggtctacgtt tctagagaaa agaggccagg     720
gtttgatcac cacaaaaagg ctggtgcaat gaatgctctg gtacgggctt cagcaattat     780
cactaatgca ccctatcttc tgaatgttga ttgtgatcac tacattaaca atagcaaggc     840
acttagagaa gctatgtgtt ttatgatgga tcctcaacta gggaaaaagg tttgctatgt     900
gcaatttcct cagcgatttg atggaattga tagacatgat agatattcaa acagaaatgt     960
tgtatttttc gatattaaca tgaaaggatt ggatgggata caaggtccaa tatatgtcgg    1020
aactggatgt gtttttcagaa ggtacgcact ttatggatat gatgcacctg ccaagaagaa    1080
accaccgagc aaaacttgta actgttggcc aaagtggtgc tgcctatgtt gtggctctag    1140
aaagaaaaag aatgccaata gtaagaagga gaaaagagg aaggtgaagc acagtgaagc    1200
atcaaagcag atacatgcac ttgaaaatat tgaggcgggg aatgaaggaa ccaacaatga    1260
gaagacatcc aatctgactc aaacaaagtt ggagaagagg tttggacagt ctccagtatt    1320
tgtagcctcc acacttttgg atgatggtgg agttccacat ggcgtgagtc ctgcatcact    1380
tttaaaagaa gccatccagg tcatcagttg tggttatgaa gacaaaacag aatggggaaa    1440
agaagttggg tggatatatg ttctgtgac agaggatatc ttgactggat ttaaaatgca    1500
ttgccatggt tggcggtctg tgtattgcat tcctaagcgg cctgcatta aggggtctgc    1560
gcctatcaac ctttcagatc gtctgcacca agttcttcgg tgggctcttg ggtctgttga    1620
gatttttttc agcagacatt gtccaatctg gtatggctat ggtggtggat tgaaattgtt    1680
ggaacgattt tcctacatta actcggtcgt atatccctgg acttccctcc cattgcttgt    1740
```

```
ctactgtact ctaccagcca tatgccttct gactggaaaa tttatcgtac ccgagattag    1800
caactatgcc agtcttgtgt tcatggccct cttcatatcc attgcagcaa ctggcatcct    1860
tgagatgcaa tggggcggtg ttagcataga cgactggtgg aggaacgaac agttttgggt    1920
gatcggaggt gtttcttccc atctatttgc cctatttcag ggtttactga aggtcttggc    1980
tggtgtgaac acaaacttca ctgtgacctc aaaagcagca gatgatggag aattctcaga    2040
actctacata ttcaagtgga catcactctt gatccctcca atgactttac ttatcatgaa    2100
tattgtcggg gtggttgtcg ggatctcaga tgccatcaac aatggttatg actcatgggg    2160
acctctcttt ggtagattgt tctttgcatt gtgggtgatc ctccatctct accccttctt    2220 gaagggttg cttggaaaac aagatagaat gccaaccatt atattggttt ggtcaatcct    2280
tctggcctcc atcttgactc tcatgtgggt cagaattaac ccgtttgtgt caagagacgg    2340
ccccgtgtta gaaatttgtg gattgaattg cgacgagtcg tgaataaaga aaagctgaag    2400
aagaagggtt agttatttt cagctacact gcagtcatgt tgaagaatgc agccagcaca    2460
tgcttcacaa agttgcacga attttcggat ggaagtttta ttttttcgggt gtgtagagat    2520 taaagagagg aaggggaggg ggctgacaca ttgttacctt gtaatagggt ttttcattt    2580 attctttgat tatattttct gtgggtttta gtgttattct ctttccagtt tcatgtatta    2640
taagaaagag gcattgaatg ataaattatt ccctcttcaa aatgggggat cctcagtctc    2700
aagaaattac ttggtcatat ttttaggtat gggtcttgtt ctgtttaaaa ccatttgtaa    2760
taccgtcaaa actatggata tcttgttcc tcagatgtgt ttttgtgttt tattatttaa    2820
cactcaggaa ccttttggtt tgattcaatt attcaatgtt tggatggcac taaaaaaaaa    2880
aaaaaaaaaa                                                            2890
```

<210> SEQ ID NO 18
<211> LENGTH: 793
<212> TYPE: PRT
<213> ORGANISM: Glycine max

<400> SEQUENCE: 18

```
His Glu Leu His Pro Val Asn Asp Ala Tyr Gly Leu Trp Leu Thr Ser
  1               5                  10                  15

Val Ile Cys Glu Ile Trp Phe Ala Val Ser Trp Ile Met Asp Gln Phe
             20                  25                  30

Pro Lys Trp Tyr Pro Ile Gln Arg Glu Thr Tyr Leu Asp Arg Leu Ser
         35                  40                  45

Leu Arg Tyr Glu Lys Glu Gly Lys Pro Ser Glu Leu Ser Ser Val Asp
     50                  55                  60

Val Phe Val Ser Thr Val Asp Pro Met Lys Glu Pro Pro Leu Ile Thr
 65                  70                  75                  80

Ala Asn Thr Val Leu Ser Ile Leu Ala Val Asp Tyr Pro Val Asp Lys
                 85                  90                  95

Val Ala Cys Tyr Val Ser Asp Asp Gly Ala Ala Met Leu Thr Phe Glu
            100                 105                 110

Ala Leu Ser Glu Thr Ser Glu Phe Ala Arg Arg Trp Val Pro Phe Cys
        115                 120                 125

Lys Lys Tyr Asn Ile Glu Pro Arg Ala Pro Glu Trp Tyr Phe Gly Gln
    130                 135                 140

Lys Met Asp Tyr Leu Lys Asn Lys Val His Pro Ala Phe Val Arg Glu
145                 150                 155                 160
```

```
Arg Arg Ala Met Lys Arg Asp Tyr Glu Glu Phe Lys Val Arg Ile Asn
            165                 170                 175

Ser Leu Val Ala Thr Ala Gln Lys Val Pro Glu Asp Gly Trp Thr Met
            180                 185                 190

Gln Asp Gly Thr Pro Trp Pro Gly Asn Asn Val Arg Asp His Pro Gly
            195                 200                 205

Met Ile Gln Val Phe Leu Gly Gln Asp Gly Val Arg Asp Val Glu Gly
            210                 215                 220

Asn Glu Leu Pro Arg Leu Val Tyr Val Ser Arg Glu Lys Arg Pro Gly
225                 230                 235                 240

Phe Asp His His Lys Lys Ala Gly Ala Met Asn Ala Leu Val Arg Ala
            245                 250                 255

Ser Ala Ile Ile Thr Asn Ala Pro Tyr Leu Leu Asn Val Asp Cys Asp
            260                 265                 270

His Tyr Ile Asn Asn Ser Lys Ala Leu Arg Glu Ala Met Cys Phe Met
            275                 280                 285

Met Asp Pro Gln Leu Gly Lys Lys Val Cys Tyr Val Gln Phe Pro Gln
            290                 295                 300

Arg Phe Asp Gly Ile Asp Arg His Asp Arg Tyr Ser Asn Arg Asn Val
305                 310                 315                 320

Val Phe Phe Asp Ile Asn Met Lys Gly Leu Asp Gly Ile Gln Gly Pro
            325                 330                 335

Ile Tyr Val Gly Thr Gly Cys Val Phe Arg Arg Tyr Ala Leu Tyr Gly
            340                 345                 350

Tyr Asp Ala Pro Ala Lys Lys Lys Pro Pro Ser Lys Thr Cys Asn Cys
            355                 360                 365

Trp Pro Lys Trp Cys Cys Leu Cys Cys Gly Ser Arg Lys Lys Lys Asn
            370                 375                 380

Ala Asn Ser Lys Lys Glu Lys Lys Arg Lys Val Lys His Ser Glu Ala
385                 390                 395                 400

Ser Lys Gln Ile His Ala Leu Glu Asn Ile Glu Ala Gly Asn Glu Gly
            405                 410                 415

Thr Asn Asn Glu Lys Thr Ser Asn Leu Thr Gln Thr Lys Leu Glu Lys
            420                 425                 430

Arg Phe Gly Gln Ser Pro Val Phe Val Ala Ser Thr Leu Leu Asp Asp
            435                 440                 445

Gly Gly Val Pro His Gly Val Ser Pro Ala Ser Leu Leu Lys Glu Ala
450                 455                 460

Ile Gln Val Ile Ser Cys Gly Tyr Glu Asp Lys Thr Glu Trp Gly Lys
465                 470                 475                 480

Glu Val Gly Trp Ile Tyr Gly Ser Val Thr Glu Asp Ile Leu Thr Gly
            485                 490                 495

Phe Lys Met His Cys His Gly Trp Arg Ser Val Tyr Cys Ile Pro Lys
            500                 505                 510

Arg Pro Ala Phe Lys Gly Ser Ala Pro Ile Asn Leu Ser Asp Arg Leu
            515                 520                 525

His Gln Val Leu Arg Trp Ala Leu Gly Ser Val Glu Ile Phe Phe Ser
            530                 535                 540

Arg His Cys Pro Ile Trp Tyr Gly Tyr Gly Gly Gly Leu Lys Leu Leu
545                 550                 555                 560

Glu Arg Phe Ser Tyr Ile Asn Ser Val Val Tyr Pro Trp Thr Ser Leu
            565                 570                 575

Pro Leu Leu Val Tyr Cys Thr Leu Pro Ala Ile Cys Leu Leu Thr Gly
```

|   |   | 580 |   |   |   | 585 |   |   |   | 590 |   |
|---|---|---|---|---|---|---|---|---|---|---|---|

Lys Phe Ile Val Pro Glu Ile Ser Asn Tyr Ala Ser Leu Val Phe Met
    595                      600                    605

Ala Leu Phe Ile Ser Ile Ala Ala Thr Gly Ile Leu Glu Met Gln Trp
610                      615                    620

Gly Gly Val Ser Ile Asp Asp Trp Trp Arg Asn Glu Gln Phe Trp Val
625                      630                    635                    640

Ile Gly Gly Val Ser Ser His Leu Phe Ala Leu Phe Gln Gly Leu Leu
                645                    650                    655

Lys Val Leu Ala Gly Val Asn Thr Asn Phe Thr Val Thr Ser Lys Ala
    660                      665                    670

Ala Asp Asp Gly Glu Phe Ser Glu Leu Tyr Ile Phe Lys Trp Thr Ser
        675                    680                    685

Leu Leu Ile Pro Pro Met Thr Leu Leu Ile Met Asn Ile Val Gly Val
690                      695                    700

Val Val Gly Ile Ser Asp Ala Ile Asn Asn Gly Tyr Asp Ser Trp Gly
705                      710                    715                    720

Pro Leu Phe Gly Arg Leu Phe Phe Ala Leu Trp Val Ile Leu His Leu
                725                    730                    735

Tyr Pro Phe Leu Lys Gly Leu Leu Gly Lys Gln Asp Arg Met Pro Thr
    740                      745                    750

Ile Ile Leu Val Trp Ser Ile Leu Leu Ala Ser Ile Leu Thr Leu Met
        755                    760                    765

Trp Val Arg Ile Asn Pro Phe Val Ser Arg Asp Gly Pro Val Leu Glu
    770                      775                    780

Ile Cys Gly Leu Asn Cys Asp Glu Ser
785                      790

<210> SEQ ID NO 19
<211> LENGTH: 1733
<212> TYPE: DNA
<213> ORGANISM: Triticum aestivum
<220> FEATURE:
<221> NAME/KEY: unsure
<222> LOCATION: (262)

<400> SEQUENCE: 19

| gaagctatgt | gcttcctaat | ggatccaaac | ctaggtccgc | aagtctgtta | tgtgcagttc | 60 |
| ccacaaaggt | ttgatggtat | tgataggaat | gatcgatatg | caaacaggaa | cactgtcttt | 120 |
| tttgatatta | acttgagggg | ccttgacggc | attcaaggac | cagtttatgt | gggaactggt | 180 |
| tgtgttttca | acagaacggc | tatctatggt | tatgagcccc | caattaaggc | gaagaagcca | 240 |
| ggtttcttgg | catcattatg | tngggcaag | aagaaggcaa | gcaagtcaaa | gaaaaggagc | 300 |
| tcagataaga | aaaagtcgaa | caagcatgtg | gacagttctg | ttccagtatt | caatctcgaa | 360 |
| gacatagagg | agggtgttga | aggtgctggg | tttgatgatg | agaaatcagt | tctcatgtct | 420 |
| caaatgagct | tagagaagag | atttggccag | tcagcagcat | tgttgcctc | cactctgatg | 480 |
| gaatatggtg | gtgttcctca | gtcgtccact | ccagaatctc | ttttgaaaga | agctatccat | 540 |
| gtcataagtt | gtggctatga | ggacaagtct | gaatgggaa | ctgagattgg | ttggatctat | 600 |
| ggatctgtca | cagaagatat | tctaactgga | ttcaagatgc | acgcaagagg | ctggcgttca | 660 |
| atctattgca | tgcccaagcg | cccagctttc | aagggatctg | cccccatcaa | tctttcagat | 720 |
| cgtctgaatc | aagtgctgcg | gtgggctctt | ggttctgttg | aaattctttt | cagccggcat | 780 |
| tgccccttat | ggtatggcta | cggagggcgc | ctcaagttcc | tggagagatt | cgcttacatc | 840 |

-continued

```
aacaccacca tttacccact aacctctctc ccgcttctag tctattgtat attgcctgct      900
atctgtctgc tcactggaaa gttcatcatg ccagagatta gcaacttggc cagtatctgg      960
ttcattgcgc tcttcctttc aatttttcgcc actggtatcc ttgagatgag gtggagtggt    1020
gttggcattg acgagtggtg gaggaatgaa cagttctggg tcattggagg tatctctgcc    1080
catctgtttg ccgtctttca gggtcttctg aaggtgcttg caggtatcga caccaacttc    1140
actgtcacct caaaggctaa tgatgaagaa ggcgactttg ctgagctcta catgttcaag    1200
tggacgacgc ttcttatccc tccgacgacc attttgatca ttaacatggt cggtgtcgtt    1260
gctggtacct cctacgccat caacagtggt taccaatcat gggggccgct ctttgggaag    1320
ctcttctttg ccttctgggt gattgttcac ttatacccat tcctcaaggg tcttatgggc    1380
aggcaaaacc gcacaccgac gattgtcatc gtctggctg tcctcctcgc ttctatcttc    1440
tccttgctgt gggttcgtgt tgatccattc actacccgtc tcgctggccc aaatatccaa    1500
acctgtggca tcaactgcta ggaaagtggg agtttgtaga cagaaaat ataacagtga    1560
tcgagcgacc acctgtggag ccagagaata tttatgttgg ggttgtgaat tactacgttt    1620
gagaaagttg tcaaaattga gaaaacacat ttgtaaatag atgtaataga ctatctaccg    1680
ttttcatgag gttaagctct ctttttttgg aaaaaaaaaa aaaaaaaaaa aaa            1733
```

```
<210> SEQ ID NO 20
<211> LENGTH: 506
<212> TYPE: PRT
<213> ORGANISM: Triticum aestivum
<220> FEATURE:
<221> NAME/KEY: UNSURE
<222> LOCATION: (88)

<400> SEQUENCE: 20
```

Glu Ala Met Cys Phe Leu Met Asp Pro Asn Leu Gly Pro Gln Val Cys
 1               5                  10                  15

Tyr Val Gln Phe Pro Gln Arg Phe Asp Gly Ile Asp Arg Asn Asp Arg
             20                  25                  30

Tyr Ala Asn Arg Asn Thr Val Phe Phe Asp Ile Asn Leu Arg Gly Leu
         35                  40                  45

Asp Gly Ile Gln Gly Pro Val Tyr Val Gly Thr Gly Cys Val Phe Asn
     50                  55                  60

Arg Thr Ala Ile Tyr Gly Tyr Glu Pro Pro Ile Lys Ala Lys Lys Pro
 65                  70                  75                  80

Gly Phe Leu Ala Ser Leu Cys Xaa Gly Lys Lys Ala Ser Lys Ser
                 85                  90                  95

Lys Lys Arg Ser Ser Asp Lys Lys Lys Ser Asn Lys His Val Asp Ser
            100                 105                 110

Ser Val Pro Val Phe Asn Leu Glu Asp Ile Glu Glu Gly Val Glu Gly
        115                 120                 125

Ala Gly Phe Asp Asp Glu Lys Ser Val Leu Met Ser Gln Met Ser Leu
    130                 135                 140

Glu Lys Arg Phe Gly Gln Ser Ala Ala Phe Ala Ser Thr Leu Met
145                 150                 155                 160

Glu Tyr Gly Gly Val Pro Gln Ser Ser Thr Pro Glu Ser Leu Leu Lys
                165                 170                 175

Glu Ala Ile His Val Ile Ser Cys Gly Tyr Glu Asp Lys Ser Glu Trp
            180                 185                 190

Gly Thr Glu Ile Gly Trp Ile Tyr Gly Ser Val Thr Glu Asp Ile Leu

```
                 195                 200                 205
Thr Gly Phe Lys Met His Ala Arg Gly Trp Arg Ser Ile Tyr Cys Met
    210                 215                 220

Pro Lys Arg Pro Ala Phe Lys Gly Ser Ala Pro Ile Asn Leu Ser Asp
225                 230                 235                 240

Arg Leu Asn Gln Val Leu Arg Trp Ala Leu Gly Ser Val Glu Ile Leu
                245                 250                 255

Phe Ser Arg His Cys Pro Leu Trp Tyr Gly Tyr Gly Arg Leu Lys
            260                 265                 270

Phe Leu Glu Arg Phe Ala Tyr Ile Asn Thr Thr Ile Tyr Pro Leu Thr
        275                 280                 285

Ser Leu Pro Leu Leu Val Tyr Cys Ile Leu Pro Ala Ile Cys Leu Leu
    290                 295                 300

Thr Gly Lys Phe Ile Met Pro Glu Ile Ser Asn Leu Ala Ser Ile Trp
305                 310                 315                 320

Phe Ile Ala Leu Phe Leu Ser Ile Phe Ala Thr Gly Ile Leu Glu Met
                325                 330                 335

Arg Trp Ser Gly Val Gly Ile Asp Glu Trp Trp Arg Asn Glu Gln Phe
            340                 345                 350

Trp Val Ile Gly Gly Ile Ser Ala His Leu Phe Ala Val Phe Gln Gly
        355                 360                 365

Leu Leu Lys Val Leu Ala Gly Ile Asp Thr Asn Phe Thr Val Thr Ser
    370                 375                 380

Lys Ala Asn Asp Glu Glu Gly Asp Phe Ala Glu Leu Tyr Met Phe Lys
385                 390                 395                 400

Trp Thr Thr Leu Leu Ile Pro Pro Thr Thr Ile Leu Ile Ile Asn Met
                405                 410                 415

Val Gly Val Val Ala Gly Thr Ser Tyr Ala Ile Asn Ser Gly Tyr Gln
            420                 425                 430

Ser Trp Gly Pro Leu Phe Gly Lys Leu Phe Ala Phe Trp Val Ile
        435                 440                 445

Val His Leu Tyr Pro Phe Leu Lys Gly Leu Met Gly Arg Gln Asn Arg
    450                 455                 460

Thr Pro Thr Ile Val Ile Val Trp Ala Val Leu Leu Ala Ser Ile Phe
465                 470                 475                 480

Ser Leu Leu Trp Val Arg Val Asp Pro Phe Thr Arg Leu Ala Gly
                485                 490                 495

Pro Asn Ile Gln Thr Cys Gly Ile Asn Cys
            500                 505

<210> SEQ ID NO 21
<211> LENGTH: 1029
<212> TYPE: DNA
<213> ORGANISM: Triticum aestivum

<400> SEQUENCE: 21
gcacgagccg ctcctcacca acggccagat ggttgatgac atcccgccgg agcagcacgc    60
gctcgtgccg tcctacatga gcggcggcgg cggcgggggc aagaggatcc acccgctccc   120
tttcgcagat cccaaccttc cagtgcaacc gagatccatg gacccgtcca aggatctggc   180
cgcctacgga tatggcagcg tggcctggaa ggagagaatg gagggctgga agcagaagca   240
ggagcgcctg cagcatgtca ggagcgaggg tggcggtgat tgggatggcg acgatgcaga   300
tctgccacta atggatgaag ctaggcagcc attgtccaga aaagtcccta tatcatcaag   360
```

-continued

```
ccgaattaat ccctacagga tgattatcgt tatccggttg gtggttttgg gtttcttctt    420
ccactaccga gtgatgcatc cggcgaaaga tgcatttgca ttgtggctca tatctgtaat    480
ctgtgaaatc tggtttgcga tgtcctgtat tcttgatcag ttcccaaagt ggtttccaat    540
cgagagagag acttacctgg accgtttgtc actaaggttt gacaaggaag gtcaaccctc    600
tcagcttgct ccaatcgact ctttgtcag tacggttgat cccacaaagg aacctccctt     660
ggtcacagcg aacactgtcc tttccatcct ttctgtggat tatccggttg agaaggtctc    720
ctgctatgtt tctgatgatg gtgctgcaat gcttacgttt gaagcattgt ctgaaacatc    780
tgaatttgca aagaaatggg ttcctttcag caaaaagttt aatatcgagc ctcgtgctcc    840
tgagtggtac ttccaacaga agatagacta cctgaaagac aaggttgctg cttcatttgt    900
tagggagagg agggcgatga agagagaata cgaggaattc aaggtaagga tcaatgcctt    960
ggttgcaaaa gcccaaaagg ttcctgagga aggatggaca atgcaagatg aagcccctg    1020 gcctggaaa                                                           1029
```

<210> SEQ ID NO 22
<211> LENGTH: 340
<212> TYPE: PRT
<213> ORGANISM: Triticum aestivum

<400> SEQUENCE: 22

```
Pro Leu Leu Thr Asn Gly Gln Met Val Asp Asp Ile Pro Pro Glu Gln
  1               5                  10                  15

His Ala Leu Val Pro Ser Tyr Met Ser Gly Gly Gly Gly Gly Gly Lys
             20                  25                  30

Arg Ile His Pro Leu Pro Phe Ala Asp Pro Asn Leu Pro Val Gln Pro
         35                  40                  45

Arg Ser Met Asp Pro Ser Lys Asp Leu Ala Ala Tyr Gly Tyr Gly Ser
     50                  55                  60

Val Ala Trp Lys Glu Arg Met Glu Gly Trp Lys Gln Lys Gln Glu Arg
 65                  70                  75                  80

Leu Gln His Val Arg Ser Glu Gly Gly Gly Asp Trp Asp Gly Asp Asp
                 85                  90                  95

Ala Asp Leu Pro Leu Met Asp Glu Ala Arg Gln Pro Leu Ser Arg Lys
            100                 105                 110

Val Pro Ile Ser Ser Ser Arg Ile Asn Pro Tyr Arg Met Ile Ile Val
        115                 120                 125

Ile Arg Leu Val Val Leu Gly Phe Phe His Tyr Arg Val Met His
    130                 135                 140

Pro Ala Lys Asp Ala Phe Ala Leu Trp Leu Ile Ser Val Ile Cys Glu
145                 150                 155                 160

Ile Trp Phe Ala Met Ser Cys Ile Leu Asp Gln Phe Pro Lys Trp Phe
                165                 170                 175

Pro Ile Glu Arg Glu Thr Tyr Leu Asp Arg Leu Ser Leu Arg Phe Asp
            180                 185                 190

Lys Glu Gly Gln Pro Ser Gln Leu Ala Pro Ile Asp Phe Phe Val Ser
        195                 200                 205

Thr Val Asp Pro Thr Lys Glu Pro Pro Leu Val Thr Ala Asn Thr Val
    210                 215                 220

Leu Ser Ile Leu Ser Val Asp Tyr Pro Val Glu Lys Val Ser Cys Tyr
225                 230                 235                 240

Val Ser Asp Asp Gly Ala Ala Met Leu Thr Phe Glu Ala Leu Ser Glu
                245                 250                 255
```

```
Thr Ser Glu Phe Ala Lys Lys Trp Val Pro Phe Ser Lys Lys Phe Asn
            260                 265                 270

Ile Glu Pro Arg Ala Pro Glu Trp Tyr Phe Gln Gln Lys Ile Asp Tyr
        275                 280                 285

Leu Lys Asp Lys Val Ala Ala Ser Phe Val Arg Glu Arg Arg Ala Met
        290                 295                 300

Lys Arg Glu Tyr Glu Glu Phe Lys Val Arg Ile Asn Ala Leu Val Ala
305                 310                 315                 320

Lys Ala Gln Lys Val Pro Glu Glu Gly Trp Thr Met Gln Asp Gly Ser
                325                 330                 335

Pro Trp Pro Gly
            340

<210> SEQ ID NO 23
<211> LENGTH: 2663
<212> TYPE: DNA
<213> ORGANISM: Picramnia pentandra

<400> SEQUENCE: 23
gcacgaggaa agaggggaag ccatctgagc tagctggctt agacatattt gtcagtacgg      60
tggatcctat gaaagaacct ccacttatca ctgcaaatac tgtgctatcc atccttgcag     120
ttgattatcc agttgataaa gttacatgct acgtgtcaga tgatggtgct gccatgctta    180
cttttgaagc actttctgaa acatctgaat ttgcacgaaa atgggtccct ttctgtaaga    240
agtttagcat tgagcctcga gcaccagaat ggtatttctc tcagaagatg gactatttga    300
agaacaaagt acacccatca tttgttaggg aaagacgtgc tatgaagaga gaatatgaag    360
tattcaaagt tcggataaat ggtttggttg ccatggcaca aaaggttccc gaggatggtt    420
ggacgatgca ggatgggact ccttggcctg gaaataatgt gcgagaccat cctggcatga    480
ttcaggtttt ccttggtcac aatggtgtcc gtgatgttga aggaaacgag ttgcctcgtc    540
tgatatatgt ttctcgtgag aagagacctg ctttgagcca cataaaaag gctggtgcaa    600 tgaattcttt ggtacgggtc tccgcggtta tctcaaatgc accctatata ctaaacgttg    660
actgtgatca ttacatcaac aatagcaaag cactgagaga agccatgtgt tcatgatgg    720 atccaacatc ggggaagaaa ttatgctatg tgcagttttcc tcaaagattt gatggcattg    780
atcgccatga tcgatattcc aaccggaatg ttgtattctt tgatataaat atgaaaggat    840
tagatggcat acaagggcct atatatgttg aacgggatg tgttttcaga agagtagcac    900
tttatggcta tgatgcacca gtcactaaga agtccccggg aaaagcttgt aactgttggc    960
ctaaatggtt gtgctgctgt tgtgggtcca gaaagaacaa gaaatcgaaa ccaaagaagg  1020
agaagaagaa gtctaaaaat agggaagcat caaagcagat acatgctctt gaaaatattg    1080
aagaaggtat gggaggattg aactctgaga atcatgtga caaccccca ctgaaattgg    1140 agaagaagtt tggacagtct ccagtgttcg tggcttctac tcttctagaa gatggtggag    1200
tccctcaaga tgcaactcct gcagcactac tgaaagaagc catacaggtc atcagctgtg    1260
gttatgaaga taaaacagaa tgggggaagg aagttggttg gatatatggc tctgtaacgg    1320
aggatattct gactggattc aagatgcact gccatggatg gcggtctgtg tactgcatgc    1380
ctgcacgccc cgcatttaag gggtcagctc ccatcaacct ttcagatcgt ctacatcagg    1440
ttcttcggtg ggcccttgga tctgtggaga ttttcttgag cagacattgt ccactctggt    1500
atggctatgg tggtggatta aaatggttag agcggttttc ctatgtcagt tcggttgttt    1560
```

-continued

```
atccttggac ctccattcct ttgcttgttt actgcacact gccagccatt tgccttctta      1620
ctgggaaatt cattgttcct gagattagca actatgcaag catcttgttt atgctcctct      1680
tcatatttat tgctgcaacc agcattcttg agatgcaatg gggtggtgtt ggaatagatg      1740
attggtggag aaatgagcaa ttttgggtca ttggaggtgt ttcatcacat cttttttgctc     1800 tcttccaagg tttactgaag gttctggctg gtgtgaacac aaacttcact gttacctcta     1860
aggctgctga tgaaggggat ttctcagagc tttacctctt caagtggaca accttattaa     1920
ttcctcccac aacgttgttg atcataaata ttgttggggt tgtggttggc gtctccgatg     1980
ccatcaataa tggttatgat tcatggggtc ctttgtttgg tcggctattt ttcgcattct     2040
gggtcattgt ccacctctat cctttcctca agggtttgct gggaaacaa gatcgcactc      2100 caaccattat tgtggtctgg tctattctgc tggcttcaat tctaacccctt ttgtgggtac    2160 gaataaatcc atttgtgtcg agagatggcc ctgtcttgga agtgtgtggg ttaaattgtg     2220
actaggagac atgaataaaa tggttatgat gtttttttttt ggtcaaaatc cctgatgtct    2280
gttgtggagc tatggattat gtctattgat tgcaagtgat gcttgcaccg atgcatcact     2340
gggaagatac aatttttgtgc aagtttatag gttggtggtg tgtagatatt aagatgagga   2400
gggttgacac attgtcattt gttttacaga gttttcatta attcttttat tattttttgt     2460
gggtgtagtt ttttgttgtc ttagcttttt tcttcagatc tcctgtatt ctaagaaata     2520 attgagtcat aatttgtttc attgtcaatg tttaggaata atttctcatc tgttgtttct     2580
gctgtttcgt cttggaaaca tggacgtgta tgtttctggt atgaagttac tggaatatta     2640
tgggtaaaaa aaaaaaaaaa aaa                                             2663
```

<210> SEQ ID NO 24
<211> LENGTH: 740
<212> TYPE: PRT
<213> ORGANISM: Picramnia pentandra

<400> SEQUENCE: 24

```
Thr Arg Lys Glu Gly Lys Pro Ser Glu Leu Ala Gly Leu Asp Ile Phe
  1               5                  10                  15

Val Ser Thr Val Asp Pro Met Lys Glu Pro Pro Leu Ile Thr Ala Asn
             20                  25                  30

Thr Val Leu Ser Ile Leu Ala Val Asp Tyr Pro Val Asp Lys Val Thr
         35                  40                  45

Cys Tyr Val Ser Asp Asp Gly Ala Ala Met Leu Thr Phe Glu Ala Leu
     50                  55                  60

Ser Glu Thr Ser Glu Phe Ala Arg Lys Trp Val Pro Phe Cys Lys Lys
 65                  70                  75                  80

Phe Ser Ile Glu Pro Arg Ala Pro Glu Trp Tyr Phe Ser Gln Lys Met
                 85                  90                  95

Asp Tyr Leu Lys Asn Lys Val His Pro Ser Phe Val Arg Glu Arg
            100                 105                 110

Ala Met Lys Arg Glu Tyr Glu Val Phe Lys Val Arg Ile Asn Gly Leu
        115                 120                 125

Val Ala Met Ala Gln Lys Val Pro Glu Asp Gly Trp Thr Met Gln Asp
    130                 135                 140

Gly Thr Pro Trp Pro Gly Asn Asn Val Arg Asp His Pro Gly Met Ile
145                 150                 155                 160

Gln Val Phe Leu Gly His Asn Gly Val Arg Asp Val Glu Gly Asn Glu
                165                 170                 175
```

-continued

```
Leu Pro Arg Leu Ile Tyr Val Ser Arg Glu Lys Arg Pro Gly Phe Glu
            180                 185                 190

His His Lys Lys Ala Gly Ala Met Asn Ser Leu Val Arg Val Ser Ala
            195                 200                 205

Val Ile Ser Asn Ala Pro Tyr Ile Leu Asn Val Asp Cys Asp His Tyr
    210                 215                 220

Ile Asn Asn Ser Lys Ala Leu Arg Glu Ala Met Cys Phe Met Met Asp
225                 230                 235                 240

Pro Thr Ser Gly Lys Lys Leu Cys Tyr Val Gln Phe Pro Gln Arg Phe
                245                 250                 255

Asp Gly Ile Asp Arg His Asp Arg Tyr Ser Asn Arg Asn Val Val Phe
                260                 265                 270

Phe Asp Ile Asn Met Lys Gly Leu Asp Gly Ile Gln Gly Pro Ile Tyr
            275                 280                 285

Val Gly Thr Gly Cys Val Phe Arg Arg Val Ala Leu Tyr Gly Tyr Asp
    290                 295                 300

Ala Pro Val Thr Lys Lys Ser Pro Gly Lys Ala Cys Asn Cys Trp Pro
305                 310                 315                 320

Lys Trp Leu Cys Cys Cys Gly Ser Arg Lys Asn Lys Lys Ser Lys
                325                 330                 335

Pro Lys Lys Glu Lys Lys Ser Lys Asn Arg Glu Ala Ser Lys Gln
            340                 345                 350

Ile His Ala Leu Glu Asn Ile Glu Glu Gly Met Gly Gly Leu Asn Ser
            355                 360                 365

Glu Lys Ser Cys Glu Thr Thr Pro Leu Lys Leu Glu Lys Lys Phe Gly
        370                 375                 380

Gln Ser Pro Val Phe Val Ala Ser Thr Leu Leu Glu Asp Gly Gly Val
385                 390                 395                 400

Pro Gln Asp Ala Thr Pro Ala Ala Leu Leu Lys Glu Ala Ile Gln Val
            405                 410                 415

Ile Ser Cys Gly Tyr Glu Asp Lys Thr Glu Trp Gly Lys Glu Val Gly
                420                 425                 430

Trp Ile Tyr Gly Ser Val Thr Glu Asp Ile Leu Thr Gly Phe Lys Met
            435                 440                 445

His Cys His Gly Trp Arg Ser Val Tyr Cys Met Pro Ala Arg Pro Ala
450                 455                 460

Phe Lys Gly Ser Ala Pro Ile Asn Leu Ser Asp Arg Leu His Gln Val
465                 470                 475                 480

Leu Arg Trp Ala Leu Gly Ser Val Glu Ile Phe Leu Ser Arg His Cys
                485                 490                 495

Pro Leu Trp Tyr Gly Tyr Gly Gly Gly Leu Lys Trp Leu Glu Arg Phe
            500                 505                 510

Ser Tyr Val Ser Ser Val Val Tyr Pro Trp Thr Ser Ile Pro Leu Leu
            515                 520                 525

Val Tyr Cys Thr Leu Pro Ala Ile Cys Leu Leu Thr Gly Lys Phe Ile
    530                 535                 540

Val Pro Glu Ile Ser Asn Tyr Ala Ser Ile Leu Phe Met Leu Leu Phe
545                 550                 555                 560

Ile Phe Ile Ala Ala Thr Ser Ile Leu Glu Met Gln Trp Gly Gly Val
                565                 570                 575

Gly Ile Asp Asp Trp Trp Arg Asn Glu Gln Phe Trp Val Ile Gly Gly
            580                 585                 590

Val Ser Ser His Leu Phe Ala Leu Phe Gln Gly Leu Leu Lys Val Leu
```

-continued

```
                    595                 600                 605
Ala Gly Val Asn Thr Asn Phe Thr Val Thr Ser Lys Ala Ala Asp Glu
    610                 615                 620

Gly Asp Phe Ser Glu Leu Tyr Leu Phe Lys Trp Thr Thr Leu Leu Ile
625                 630                 635                 640

Pro Pro Thr Thr Leu Leu Ile Ile Asn Ile Val Gly Val Val Val Gly
                645                 650                 655

Val Ser Asp Ala Ile Asn Asn Gly Tyr Asp Ser Trp Gly Pro Leu Phe
            660                 665                 670

Gly Arg Leu Phe Phe Ala Phe Trp Val Ile Val His Leu Tyr Pro Phe
        675                 680                 685

Leu Lys Gly Leu Leu Gly Lys Gln Asp Arg Thr Pro Thr Ile Ile Val
    690                 695                 700

Val Trp Ser Ile Leu Leu Ala Ser Ile Leu Thr Leu Leu Trp Val Arg
705                 710                 715                 720

Ile Asn Pro Phe Val Ser Arg Asp Gly Pro Val Leu Glu Val Cys Gly
                725                 730                 735

Leu Asn Cys Asp
            740

<210> SEQ ID NO 25
<211> LENGTH: 3563
<212> TYPE: DNA
<213> ORGANISM: Impatiens balsamia

<400> SEQUENCE: 25
gcacgagagg caaacgccgg actagtcgcc ggatcttaca agcggaacga gcttgtccga      60
attcgccacg attcagatgg cgggcagccg aagcccctaa aagaggctaa cggacagata     120
tgtcagatat gcggtgacac agtcggaaaa tcagccaccg gcgacacttt cgttgcctgt     180
aatgaatgtg gattccccgt ttgccggcct tgttacgagt acgaaaggaa agatggaaac     240
caatgctgcc ctcagtgcaa gaccagatac aaaagacaga agggagtcc tagagttgaa      300
ggagatgaag aagaggagga tgtggatgat ttggaaaacg agttcaatta ttccggtaaa     360
gggaagaacc agaagaaggt aaccacggca aggcggccat ggcagggaga tcagcaggat     420
attgagctct ctgtttcatc atctaggcat gatgaatccc aacaacctgt acctcttctc     480
actcacgggc actcggtatc gggcgaaatt cccactcccg ataatcattc tataaggact     540
acatcaggtc ccataggccc tgtggaaaaa tccattccct atatcgatcc aggcagcca      600
gttgctgtga gaataattgt tgaccctcc aaggacttga actcgtacgg gcttggcaat      660
gtggattgga aggaaagggt tgaaggttgg aaacttaagc aggagaaaaa tatggtgcaa     720
atgaccagta gatatcctga agggaaagga gatactgaag gtacgggatc aaatggggag     780
gaacttcaaa tggctgccga cgatatccga caacccatga gccgaatcgt gcccatttcg     840
tcgacgcacc tcactcccta cagagtggtt atcatacttc ggttaattat cctcggtttc     900
ttcttgcaat accgttgtac tcatccagtg aaagatgctt atccattatg gcttacctcg     960
gttatttgtg aagtttggtt tgcattgtca tggctgcttg atcagttccc taaatggtcg    1020
cctgtgaacc gcgagactta tctcgacaga ctgtccatga gattcgatag ggaaggggag    1080
ccttcgcaat tggcgccaat tgacgtattt gttagtaccg tggatccttt gaaagagcca    1140
ccactcgtga cagccaacac ggttttgtct atcctggccg tggattaccc tgttgacaaa    1200
gtctcttgct atgtttcgga tgacggttca gcaatgttga ccttcgaagc tctatccgag    1260
```

-continued

```
acagccgagt tgctaagaa atgggcaccc ttctgtaaga aacatagtat tgaacctcgg    1320
gcgcccgaat tttatttcgc tcaaaagatt gattacttga aggataaggt gcagccttct    1380
ttcgtgaagg agcggagggc gatgaagagg gaatacgaag aatttaaggt taggattaat    1440
gcgcttgttg cgaaagcgca aaaagtgcca gaagaaggat ggacgatgca agatggaact    1500
ccatggccgg gaaataactc gagagatcat cctggaatga ttcaggtttt tttaggccat    1560
agtggggtt tcgatacgga gggaaatgag ttacctcggc tggtgtacgt ttctcgtgag    1620
aaacgtcctg gatttcagca tcacaagaaa gccggggcaa tgaacgcatt gattcgagta    1680
tcggcagtgc tgacaaatgg ggcttatctg cttaacgtgg attgtgatca ctacttcaac    1740
aacagcaaat gtctaaaaga ggcaatgtgc tttatgatgg atccaaacct tggaaagaaa    1800
acatgttacg ttcagttccc tcaacggttt gatggtattg acttgcacga tcgatatgct    1860
aaccgtaaca ttgtcttctt cgatatcaac ttgaagggt tggacggcat tcagggccca    1920
gtttatgtgg gtaccggttg ttgtttcaac agacaggcgc tatacgggta tgatccagtc    1980
ttaacagagg aggatttgga accgaatatc atcatcaaga gctgttgcgg ctcgaggaaa    2040
aagggtaaag gtggcaacaa gaagtacatt gacaaaaaca gagcactaaa gcgaaccgaa    2100
tcaaccgcgc ccattttcaa tatggaagat attgaagagg gcattgaagg ttacgatgac    2160
gagagatctt ttctcatggc acagagttac gaaaagcggt tcggtcaatc ccctgttctt    2220
attgctgcca cgttcatgga acaaggcggc cttcctcctt ccacaaactc tgcaaccctc    2280
ttgaaagaag caatccatgt tattagctgt gggtacgagg acaagactga atggggcaaa    2340
gagattggat ggatatatgg atctgtaacg gaagatatct tgaccgggtt caagatgcat    2400
acgagaggat ggatttcaat ctactgcatg ccgccacgcc ctgccttcaa aggatctgca    2460
cccattaatc tttcggatcg tttgaaccag gtccttcgat gggctctcgg atcgattgag    2520
attcttttga gtagacattg ccccatttgg tatggctaca gcggtagact caagttcttg    2580
gagagattgg cttatatcaa tactattgtt tatccactca cctccattcc tttacttgct    2640
tattgcaccc ttcctgctat ctgcttactc accggaaagt tcatcgttcc ggagataagc    2700
aactacgcga gcatctggtt cattcttctg ttcgtgtcta ttttctcgac gggaatactg    2760
gagctaagat gggcggggt tacactggag gactggtgga gaaacgagca attctgggta    2820
atcggtggca cgtcggctca tctctttgcc gtgttccaag gcctgctaaa agtgcttgcg    2880
gggatcgaca cgaatttcac cgtcacgtcg aaagcgtcgg acgaggacgg ggactttgcg    2940
gagctttacg ttttcaagtg gacttccctt ctcatccctc cgaccaccat tctggttgtg    3000
aacatggtgg ggatagtggc cggcgtctcg ttcgccatca acagtggata ccagtcgtgg    3060
ggaccgctct tcggaaggtt gttctttgcg atatgggtta ttgtccattt gtacccattc    3120
cttaagggtt tgttgggacg gcagaatcgg acacccacga ttgttattgt ctggtctgta    3180
cttttggctt ccatattttc tcttctatgg gtgcgtattg atccgtttac atcggactcg    3240
acaaaggctc gggggcaatg tgggatcgat tgctgagaat tgagattgtc ccgagtctgt    3300
tgttacagta aatagatggg catggccgcc atagagaaga tgaagaaggt aactacttaa    3360
attggcgtcc acattttgtt aggcttctgc ccttcacaga caatgagggc caaagtgttt    3420
gatatgtcta ggtattaatg tgttatacca actctaatct aaaacagtgt aatggattcc    3480
agaatgacga atgacttgtt cggtttcaat tatttgaatt cctcaaaaac taatatcttt    3540
tcccaaaaaa aaaaaaaaa aaa                                              3563
```

-continued

```
<210> SEQ ID NO 26
<211> LENGTH: 1091
<212> TYPE: PRT
<213> ORGANISM: Impatiens balsamia

<400> SEQUENCE: 26
```

| Ala | Arg | Glu | Ala | Asn | Ala | Gly | Leu | Val | Ala | Gly | Ser | Tyr | Lys | Arg | Asn |
|---|---|---|---|---|---|---|---|---|---|---|---|---|---|---|---|
| 1 | | | | 5 | | | | | 10 | | | | | 15 | |

| Glu | Leu | Val | Arg | Ile | Arg | His | Asp | Ser | Asp | Gly | Gln | Pro | Lys | Pro |
|---|---|---|---|---|---|---|---|---|---|---|---|---|---|---|
| | | | 20 | | | | | 25 | | | | | 30 | |

| Leu | Lys | Glu | Ala | Asn | Gly | Gln | Ile | Cys | Gln | Ile | Cys | Gly | Asp | Thr | Val |
|---|---|---|---|---|---|---|---|---|---|---|---|---|---|---|---|
| | | 35 | | | | | 40 | | | | | 45 | | | |

| Gly | Lys | Ser | Ala | Thr | Gly | Asp | Thr | Phe | Val | Ala | Cys | Asn | Glu | Cys | Gly |
|---|---|---|---|---|---|---|---|---|---|---|---|---|---|---|---|
| | 50 | | | | | 55 | | | | | 60 | | | | |

| Phe | Pro | Val | Cys | Arg | Pro | Cys | Tyr | Glu | Tyr | Glu | Arg | Lys | Asp | Gly | Asn |
|---|---|---|---|---|---|---|---|---|---|---|---|---|---|---|---|
| 65 | | | | | 70 | | | | | 75 | | | | | 80 |

| Gln | Cys | Cys | Pro | Gln | Cys | Lys | Thr | Arg | Tyr | Lys | Arg | Gln | Lys | Gly | Ser |
|---|---|---|---|---|---|---|---|---|---|---|---|---|---|---|---|
| | | | | 85 | | | | | 90 | | | | | 95 | |

| Pro | Arg | Val | Glu | Gly | Asp | Glu | Glu | Glu | Asp | Val | Asp | Asp | Leu | Glu |
|---|---|---|---|---|---|---|---|---|---|---|---|---|---|---|
| | | | | 100 | | | | | 105 | | | | | 110 |

| Asn | Glu | Phe | Asn | Tyr | Ser | Gly | Lys | Gly | Lys | Asn | Gln | Lys | Lys | Val | Thr |
|---|---|---|---|---|---|---|---|---|---|---|---|---|---|---|---|
| | | 115 | | | | | 120 | | | | | 125 | | | |

| Thr | Ala | Arg | Arg | Pro | Trp | Gln | Gly | Asp | Gln | Gln | Asp | Ile | Glu | Leu | Ser |
|---|---|---|---|---|---|---|---|---|---|---|---|---|---|---|---|
| | 130 | | | | | 135 | | | | | 140 | | | | |

| Val | Ser | Ser | Arg | His | Asp | Glu | Ser | Gln | Gln | Pro | Val | Pro | Leu | Leu |
|---|---|---|---|---|---|---|---|---|---|---|---|---|---|---|
| 145 | | | | | 150 | | | | | 155 | | | | | 160 |

| Thr | His | Gly | His | Ser | Val | Ser | Gly | Glu | Ile | Pro | Thr | Pro | Asp | Asn | His |
|---|---|---|---|---|---|---|---|---|---|---|---|---|---|---|---|
| | | | | 165 | | | | | 170 | | | | | 175 | |

| Ser | Ile | Arg | Thr | Thr | Ser | Gly | Pro | Ile | Gly | Pro | Val | Glu | Lys | Ser | Ile |
|---|---|---|---|---|---|---|---|---|---|---|---|---|---|---|---|
| | | | 180 | | | | | 185 | | | | | 190 | | |

| Pro | Tyr | Ile | Asp | Pro | Arg | Gln | Pro | Val | Ala | Val | Arg | Ile | Ile | Val | Asp |
|---|---|---|---|---|---|---|---|---|---|---|---|---|---|---|---|
| | | 195 | | | | | 200 | | | | | 205 | | | |

| Pro | Ser | Lys | Asp | Leu | Asn | Ser | Tyr | Gly | Leu | Gly | Asn | Val | Asp | Trp | Lys |
|---|---|---|---|---|---|---|---|---|---|---|---|---|---|---|---|
| | 210 | | | | | 215 | | | | | 220 | | | | |

| Glu | Arg | Val | Glu | Gly | Trp | Lys | Leu | Lys | Gln | Glu | Lys | Asn | Met | Val | Gln |
|---|---|---|---|---|---|---|---|---|---|---|---|---|---|---|---|
| 225 | | | | | 230 | | | | | 235 | | | | | 240 |

| Met | Thr | Ser | Arg | Tyr | Pro | Glu | Gly | Lys | Gly | Asp | Thr | Glu | Gly | Thr | Gly |
|---|---|---|---|---|---|---|---|---|---|---|---|---|---|---|---|
| | | | 245 | | | | | 250 | | | | | 255 | | |

| Ser | Asn | Gly | Glu | Glu | Leu | Gln | Met | Ala | Ala | Asp | Asp | Ile | Arg | Gln | Pro |
|---|---|---|---|---|---|---|---|---|---|---|---|---|---|---|---|
| | | 260 | | | | | 265 | | | | | 270 | | | |

| Met | Ser | Arg | Ile | Val | Pro | Ile | Ser | Ser | Thr | His | Leu | Thr | Pro | Tyr | Arg |
|---|---|---|---|---|---|---|---|---|---|---|---|---|---|---|---|
| | 275 | | | | | 280 | | | | | 285 | | | | |

| Val | Val | Ile | Ile | Leu | Arg | Leu | Ile | Ile | Leu | Gly | Phe | Phe | Leu | Gln | Tyr |
|---|---|---|---|---|---|---|---|---|---|---|---|---|---|---|---|
| | 290 | | | | | 295 | | | | | 300 | | | | |

| Arg | Cys | Thr | His | Pro | Val | Lys | Asp | Ala | Tyr | Pro | Leu | Trp | Leu | Thr | Ser |
|---|---|---|---|---|---|---|---|---|---|---|---|---|---|---|---|
| 305 | | | | | 310 | | | | | 315 | | | | | 320 |

| Val | Ile | Cys | Glu | Val | Trp | Phe | Ala | Leu | Ser | Trp | Leu | Leu | Asp | Gln | Phe |
|---|---|---|---|---|---|---|---|---|---|---|---|---|---|---|---|
| | | | | 325 | | | | | 330 | | | | | 335 | |

| Pro | Lys | Trp | Ser | Pro | Val | Asn | Arg | Glu | Thr | Tyr | Leu | Asp | Arg | Leu | Ser |
|---|---|---|---|---|---|---|---|---|---|---|---|---|---|---|---|
| | | | 340 | | | | | 345 | | | | | 350 | | |

| Met | Arg | Phe | Asp | Arg | Glu | Gly | Glu | Pro | Ser | Gln | Leu | Ala | Pro | Ile | Asp |
|---|---|---|---|---|---|---|---|---|---|---|---|---|---|---|---|
| | 355 | | | | | 360 | | | | | 365 | | | | |

| Val | Phe | Val | Ser | Thr | Val | Asp | Pro | Leu | Lys | Glu | Pro | Pro | Leu | Val | Thr |
|---|---|---|---|---|---|---|---|---|---|---|---|---|---|---|---|
| | 370 | | | | | 375 | | | | | 380 | | | | |

```
-continued

Ala Asn Thr Val Leu Ser Ile Leu Ala Val Asp Tyr Pro Val Asp Lys
385                 390                 395                 400

Val Ser Cys Tyr Val Ser Asp Asp Gly Ser Ala Met Leu Thr Phe Glu
                405                 410                 415

Ala Leu Ser Glu Thr Ala Glu Phe Ala Lys Lys Trp Ala Pro Phe Cys
            420                 425                 430

Lys Lys His Ser Ile Glu Pro Arg Ala Pro Glu Phe Tyr Phe Ala Gln
        435                 440                 445

Lys Ile Asp Tyr Leu Lys Asp Lys Val Gln Pro Ser Phe Val Lys Glu
    450                 455                 460

Arg Arg Ala Met Lys Arg Glu Tyr Glu Glu Phe Lys Val Arg Ile Asn
465                 470                 475                 480

Ala Leu Val Ala Lys Ala Gln Lys Val Pro Glu Glu Gly Trp Thr Met
                485                 490                 495

Gln Asp Gly Thr Pro Trp Pro Gly Asn Asn Ser Arg Asp His Pro Gly
            500                 505                 510

Met Ile Gln Val Phe Leu Gly His Ser Gly Gly Phe Asp Thr Glu Gly
        515                 520                 525

Asn Glu Leu Pro Arg Leu Val Tyr Val Ser Arg Glu Lys Arg Pro Gly
    530                 535                 540

Phe Gln His His Lys Lys Ala Gly Ala Met Asn Ala Leu Ile Arg Val
545                 550                 555                 560

Ser Ala Val Leu Thr Asn Gly Ala Tyr Leu Leu Asn Val Asp Cys Asp
                565                 570                 575

His Tyr Phe Asn Asn Ser Lys Cys Leu Lys Glu Ala Met Cys Phe Met
            580                 585                 590

Met Asp Pro Asn Leu Gly Lys Lys Thr Cys Tyr Val Gln Phe Pro Gln
        595                 600                 605

Arg Phe Asp Gly Ile Asp Leu His Asp Arg Tyr Ala Asn Arg Asn Ile
    610                 615                 620

Val Phe Phe Asp Ile Asn Leu Lys Gly Leu Asp Gly Ile Gln Gly Pro
625                 630                 635                 640

Val Tyr Val Gly Thr Gly Cys Cys Phe Asn Arg Gln Ala Leu Tyr Gly
                645                 650                 655

Tyr Asp Pro Val Leu Thr Glu Glu Asp Leu Glu Pro Asn Ile Ile Ile
            660                 665                 670

Lys Ser Cys Cys Gly Ser Arg Lys Lys Gly Lys Gly Asn Lys Lys
        675                 680                 685

Tyr Ile Asp Lys Asn Arg Ala Leu Lys Arg Thr Glu Ser Thr Ala Pro
    690                 695                 700

Ile Phe Asn Met Glu Asp Ile Glu Glu Gly Ile Glu Gly Tyr Asp Asp
705                 710                 715                 720

Glu Arg Ser Phe Leu Met Ala Gln Ser Tyr Glu Lys Arg Phe Gly Gln
                725                 730                 735

Ser Pro Val Leu Ile Ala Ala Thr Phe Met Glu Gln Gly Gly Leu Pro
            740                 745                 750

Pro Ser Thr Asn Ser Ala Thr Leu Leu Lys Glu Ala Ile His Val Ile
        755                 760                 765

Ser Cys Gly Tyr Glu Asp Lys Thr Glu Trp Gly Lys Glu Ile Gly Trp
    770                 775                 780

Ile Tyr Gly Ser Val Thr Glu Asp Ile Leu Thr Gly Phe Lys Met His
785                 790                 795                 800

Thr Arg Gly Trp Ile Ser Ile Tyr Cys Met Pro Pro Arg Pro Ala Phe
```

-continued

```
                805                 810                 815
Lys Gly Ser Ala Pro Ile Asn Leu Ser Asp Arg Leu Asn Gln Val Leu
            820                 825                 830
Arg Trp Ala Leu Gly Ser Ile Glu Ile Leu Leu Ser Arg His Cys Pro
        835                 840                 845
Ile Trp Tyr Gly Tyr Ser Gly Arg Leu Lys Phe Leu Glu Arg Leu Ala
    850                 855                 860
Tyr Ile Asn Thr Ile Val Tyr Pro Leu Thr Ser Ile Pro Leu Leu Ala
865                 870                 875                 880
Tyr Cys Thr Leu Pro Ala Ile Cys Leu Leu Thr Gly Lys Phe Ile Val
            885                 890                 895
Pro Glu Ile Ser Asn Tyr Ala Ser Ile Trp Phe Ile Leu Leu Phe Val
        900                 905                 910
Ser Ile Phe Ser Thr Gly Ile Leu Glu Leu Arg Trp Ser Gly Val Thr
    915                 920                 925
Leu Glu Asp Trp Trp Arg Asn Glu Gln Phe Trp Val Ile Gly Gly Thr
930                 935                 940
Ser Ala His Leu Phe Ala Val Phe Gln Gly Leu Leu Lys Val Leu Ala
945                 950                 955                 960
Gly Ile Asp Thr Asn Phe Thr Val Thr Ser Lys Ala Ser Asp Glu Asp
            965                 970                 975
Gly Asp Phe Ala Glu Leu Tyr Val Phe Lys Trp Thr Ser Leu Leu Ile
        980                 985                 990
Pro Pro Thr Thr Ile Leu Val Val Asn Met Val Gly Ile Val Ala Gly
    995                 1000                1005
Val Ser Phe Ala Ile Asn Ser Gly Tyr Gln Ser Trp Gly Pro Leu Phe
    1010                1015                1020
Gly Arg Leu Phe Phe Ala Ile Trp Val Ile Val His Leu Tyr Pro Phe
1025                1030                1035                1040
Leu Lys Gly Leu Leu Gly Arg Gln Asn Arg Thr Pro Thr Ile Val Ile
            1045                1050                1055
Val Trp Ser Val Leu Leu Ala Ser Ile Phe Ser Leu Leu Trp Val Arg
        1060                1065                1070
Ile Asp Pro Phe Thr Ser Asp Ser Thr Lys Ala Arg Gly Gln Cys Gly
    1075                1080                1085
Ile Asp Cys
    1090

<210> SEQ ID NO 27
<211> LENGTH: 1560
<212> TYPE: DNA
<213> ORGANISM: Glycine max

<400> SEQUENCE: 27
gcacgagggg aagggaacc atcacagcta gcagctgttg acattttgt cagtactgtt      60 gatccattaa agaaccccc gcttgtgact gctaacactg tcctatctat tctttctgtt    120
gactacccag tggataaggt ctcctgttat gtctctgatg atggtgctgc tatgttgaca    180
tttgaagctc tggctgagac atcagaattt gctaggaaat gggttccttt cagcaagaaa    240
tataatatcg aacctcgggc acctgagtgg tattttgcac agaagattga ctacttgaaa    300
gataaggttc aaccatcatt tgtcaaagat cgtagagcaa tgaagagaga atatgaagaa    360
tttaaaattc gcatcaatgg acttgttgca aggcacaaa agattcctga gaaggatgg     420 gtgatgcaag atggtacgcc atggcctgga acaacacta gagaccatcc aggaatgatt    480
```

-continued

```
caggttttct tgggccaaag tggaggactt gacactgagg gtaatgaact tccacgttta      540
gtctatgttt ctcgtgaaaa gcgtccaggg ttccaacatc acaagaaggc tggtgccatg      600
aatgcacttg ttcgagtgtc agcagtcctt actaatggac ctttcttatt gaatcttgat      660
tgtgatcact acataaacaa cagtaaagcc ttgagggaag ctatgtgctt tatgatggat      720
cccaaccttg ggaaaaatgt ttgctatgtc cagtttccac agaggtttga tggtattgat      780
aggaatgatc gatatgccaa tcgcaatact gttttctttg atataaactt gagaggtttg      840
gatggcattc aaggtcctgt ttatgtgggt actggatgtg tctttaatag aacagctttg      900
tatggctacg aacctcctat taaacccaag cataaaaagc ctgggtttct ttcttcactc      960
tgtggtggta accgaaagaa gagatcaaaa tctagcaaga aaggctcaga caagaaaaaa     1020
tctagcaaga atgttgaccc aactgtgccc atctttagtc ttgaggatat agaagagggg     1080
gtggaaggtg ctggatttga tgatgagaaa tcactactta tgtcacaaat gagcctcgag     1140
aaaaggtttg gtcagtctgc tgtctttgtt gcctctacac tcatggagaa tggtggcgtt     1200
cctcagtctg caactccaga aactcttctt aaggaagcta ttcatgttat cagttgtggt     1260
tacgaggata aatcagaatg gggaagtgag gtatgagtta ccttatgttt aatggtcttt     1320
tatgtttctt attcccagtc gcatcctgtt atcagattaa tgttagcaga ttagtgtgca     1380
ttcagggacc aaagatccaa tgaattaaac ttaaatatga taaagtatga acagtatagt     1440
actgtctttt ttgagcctaa tatattaccc tctttgtaca gagttaaaag gggagcttta     1500 aaatcttttcc ttttctaagt aatgtgtgag atttcactag aaaaaaaaaa aaaaaaaaaa     1560
```

<210> SEQ ID NO 28
<211> LENGTH: 431
<212> TYPE: PRT
<213> ORGANISM: Glycine max

<400> SEQUENCE: 28

```
Ala Arg Gly Glu Gly Glu Pro Ser Gln Leu Ala Ala Val Asp Ile Phe
  1               5                  10                  15

Val Ser Thr Val Asp Pro Leu Lys Glu Pro Pro Leu Val Thr Ala Asn
                 20                  25                  30

Thr Val Leu Ser Ile Leu Ser Val Asp Tyr Pro Val Asp Lys Val Ser
             35                  40                  45

Cys Tyr Val Ser Asp Asp Gly Ala Ala Met Leu Thr Phe Glu Ala Leu
         50                  55                  60

Ala Glu Thr Ser Glu Phe Ala Arg Lys Trp Val Pro Phe Ser Lys Lys
     65                  70                  75                  80

Tyr Asn Ile Glu Pro Arg Ala Pro Glu Trp Tyr Phe Ala Gln Lys Ile
                 85                  90                  95

Asp Tyr Leu Lys Asp Lys Val Gln Pro Ser Phe Val Lys Asp Arg Arg
            100                 105                 110

Ala Met Lys Arg Glu Tyr Glu Glu Phe Lys Ile Arg Ile Asn Gly Leu
        115                 120                 125

Val Ala Lys Ala Gln Lys Ile Pro Glu Glu Gly Trp Val Met Gln Asp
    130                 135                 140

Gly Thr Pro Trp Pro Gly Asn Asn Thr Arg Asp His Pro Gly Met Ile
145                 150                 155                 160

Gln Val Phe Leu Gly Gln Ser Gly Gly Leu Asp Thr Glu Gly Asn Glu
                165                 170                 175

Leu Pro Arg Leu Val Tyr Val Ser Arg Glu Lys Arg Pro Gly Phe Gln
```

```
                    180                 185                 190
His His Lys Lys Ala Gly Ala Met Asn Ala Leu Val Arg Val Ser Ala
            195                 200                 205
Val Leu Thr Asn Gly Pro Phe Leu Leu Asn Leu Asp Cys Asp His Tyr
    210                 215                 220
Ile Asn Ser Lys Ala Leu Arg Glu Ala Met Cys Phe Met Met Asp
225                 230                 235                 240
Pro Asn Leu Gly Lys Asn Val Cys Tyr Val Gln Phe Pro Gln Arg Phe
                245                 250                 255
Asp Gly Ile Asp Arg Asn Asp Arg Tyr Ala Asn Arg Asn Thr Val Phe
            260                 265                 270
Phe Asp Ile Asn Leu Arg Gly Leu Asp Gly Ile Gln Gly Pro Val Tyr
        275                 280                 285
Val Gly Thr Gly Cys Val Phe Asn Arg Thr Ala Leu Tyr Gly Tyr Glu
    290                 295                 300
Pro Pro Ile Lys Pro Lys His Lys Lys Pro Gly Phe Leu Ser Ser Leu
305                 310                 315                 320
Cys Gly Gly Asn Arg Lys Lys Arg Ser Lys Ser Ser Lys Lys Gly Ser
                325                 330                 335
Asp Lys Lys Lys Ser Ser Lys Asn Val Asp Pro Thr Val Pro Ile Phe
            340                 345                 350
Ser Leu Glu Asp Ile Glu Glu Gly Val Glu Gly Ala Gly Phe Asp Asp
        355                 360                 365
Glu Lys Ser Leu Leu Met Ser Gln Met Ser Leu Glu Lys Arg Phe Gly
    370                 375                 380
Gln Ser Ala Val Phe Val Ala Ser Thr Leu Met Glu Asn Gly Gly Val
385                 390                 395                 400
Pro Gln Ser Ala Thr Pro Glu Thr Leu Leu Lys Glu Ala Ile His Val
                405                 410                 415
Ile Ser Cys Gly Tyr Glu Asp Lys Ser Glu Trp Gly Ser Glu Val
            420                 425                 430

<210> SEQ ID NO 29
<211> LENGTH: 3626
<212> TYPE: DNA
<213> ORGANISM: Triticum aestivum

<400> SEQUENCE: 29
gcacgaggaa ccccgctcca gctctgtcgt cggtgcgggt tggatcgctc tgccgcgcca    60
tggacggcga cgcggacgcc ctgaagtccg ggaggcacgg ggccgggac gtgtgccaga   120 tctgcgccga cggcctgggc accacgttgg acggcgacgc cttcaccgcc tgcgacgtct   180
gccgcttccc ggtctgccgc ccctgctacg agcacgagcg caaggagggc acccaggcct   240
gcctccagtg caagaccaag tacaagcgcc acagagggag cccagcgatc cgcggggagg   300
aaggcgacga cactgatgcc gatgatggta gtgacttcaa ctaccctgca tctggcactg   360
aggaccagaa gcagaagatt gctgacagga tgcgcagctg cgcatgaac ccgggggca   420 gtggcaatgt tggccacccc aagtatgaca gtggcgagat cggcctctcc aagtatgaca   480
gtggagagat ccctagggga tacgtcccctt cagtcaccaa cagccagatg tcaggagaaa   540
tccctggagc ttcgcctgat catcacatga tgtcccctac ggggaacatc agcagacgtg   600
ctccgtttcc ctatgtgaat cattcaccaa atccgtcaag ggagttctcc ggcagtattg   660
ggaatgttgc ctggaaagag agagttgatg gctggaaaat gaagcaggac aagggtgcga   720
```

-continued

| | |
|---|---|
| ttcccatgac taatgggaca agcattgctc cctctgaagg tcgggcagct actgacatcg | 780 |
| atgcatctac tgaatacaac atggaagacg ctttactgaa tgatgaaact cgccagcctc | 840 |
| tatctagaaa agtccccatt gcttcctcca aaataaatcc ctacagaatg gtcattgttc | 900 |
| tgcggttggt tgttctaagc atcttcctgc actaccgtct cacaaatcct gtgcgtaatg | 960 |
| catacccact gtggctttta tctgttatat gtgagatttg gtttgcttta tcctggatac | 1020 |
| tggatcagtt cccgaagtgg tttccaatca accgggagac ctaccttgat agactggctt | 1080 |
| taaggtatga ccgagaaggt gaaccgtctc agttggctgc tgttgacata tttgtcagta | 1140 |
| cagtcgaccc cttgaaggag ccacctatcg tcactgccaa cactgtgcta tccattcttg | 1200 |
| ctgttgatta tcccgtggac aaggtctctt gctatgtatc tgatgacgga gcttcaatgc | 1260 |
| tgacttttga cgcattggct gagacttcag agtttgctag gaaatgggta ccatttgtga | 1320 |
| agaagtatga cattgaaccc agagctcccg agttttactt ttgccagaaa attgattacc | 1380 |
| tgaaagacaa agtccagcct tcatttgtta agaccgccg ggccatgaag agagaatatg | 1440 |
| aagaatttaa aatcaggata aatgccctag tttctaaggc attgaaagtc cccgaggaag | 1500 |
| gatggatcat gcaagatggc acaccatggc caggaaacaa taccagggat catcctggaa | 1560 |
| tgattcaggt tttccttggt cacagtggtg gccttgatac tgagggtaat gagctccccc | 1620 |
| gtttagttta tgtgtctcgt gaaaagcgtc ctgggttcca gcaccacaag aaggctggtg | 1680 |
| ccatgaatgc ccttgttcgt gtctcagctg tccttactaa tggacaatac atgttgaatc | 1740 |
| ttgattgtga tcactacatc aacaacagca aggctgtccg agaagctatg tgcttcctaa | 1800 |
| tggatccaaa cctaggtccg caagtctgtt atgtgcagtt cccacaaagg tttgatggga | 1860 |
| ttgataggaa tgatcgatat gcaaacagga acactgtctt ttttgatatt aacttgaggg | 1920 |
| gccttgacgg cattcaagga ccagtttatg tgggaactgg ttgtgttttc aacagaacag | 1980 |
| ctatctatgg ttatgagccc ccaattaagg cgaagaagcc aggtttcttg gcatcactat | 2040 |
| gtggggcaa gaagaaggca agcaagtcaa agaaaaggag ctcagataag aaaaagtcga | 2100 |
| acaagcatgt ggacagttct gttccagtat tcaatctcga agacatagag gagggtgttg | 2160 |
| aaggtgctgg gtttgatgat gagaaatcag ttctcatgtc tcaaatgagc ttagagaaga | 2220 |
| gatttggcca gtcagcagca tttgttgcct ccactctgat ggaatatggt ggtgttcctc | 2280 |
| agtcctccac tccagaatct cttttgaaag aagctatcca tgtcataagt tgtggctatg | 2340 |
| aggacaagtc tgaatgggga actgagattg gttggatcta tggatctgtc acagaagata | 2400 |
| ttcttactgg attcaagatg cacgcaagag gctggcgttc agtctattgc atgcccaagc | 2460 |
| gcccagcttt caagggatct gccccatca atctttcaga tcgtctgaac caagtgctgc | 2520 |
| ggtgggctct cggttctgtt gaaattcttt tcagccggca ttgcccctta tggtatggct | 2580 |
| acggagggcg cctcaagttc ctggagagat tcgcttacat caacaccacc atttacccac | 2640 |
| taacctctct cccgcttcta gtctattgta tattgcctgc tatctgtctg ctcactggaa | 2700 |
| agttcatcat gccagagatt agcaacttgg ccagtatctg gttcattgcg ctcttccttt | 2760 |
| caattttcgc cactggtatc cttgagatga ggtggagtgg tgttggcatt gacgagtggt | 2820 |
| ggaggaatga acagttctgg gtcattggag gtatctctgc acatctgttt gccgtctttc | 2880 |
| agggtcttct gaaggtgctt gccggtatcg acaccaactt cactgtcacc tcaaaggcta | 2940 |
| atgacgaaga aggcgacttt gctgagctct acatgttcaa gtggacgacg cttctcatcc | 3000 |
| ctccgacgac cattttgatc attaacatgg ttggtgtcgt tgctggcacc tcctacgcca | 3060 |
| tcaacagtgg ttaccaatca tgggggccgc tctttgggaa gctcttcttt gccttctggg | 3120 |

-continued

```
tgattgttca cttataccca ttcctcaagg gtcttatggg caggcaaaac cgcacaccga    3180
cgattgtcat cgtctgggct gtcctcctcg cttctatctt ctccttgctg tgggttcgtg    3240
ttgatccatt cactacccgt ctcgctggcc caaatatcca aacctgtggc atcaactgct    3300
aggaaagtgg gagtttgtag agacagaaaa tataacagtg atcgagcaac aacccgcgga    3360
gccagagaat atttatgttg gggttgtgaa ttactacgtt tgagaaagtt gtcaaaattg    3420
agaaaacaca tttgtaaata gatgtaatag accatctacc gttttcatga ggttaagctc    3480
ttcttttttt ggaacaaagg aatctcattg gtaaacctat aggaattttc ctatgaggca    3540
ctttggattg taggaatgga cctatgaaat gttgtattta ttatttatat aaattattcc    3600
tgtccttcac attttggagg agtttt                                        3626
```

<210> SEQ ID NO 30
<211> LENGTH: 1080
<212> TYPE: PRT
<213> ORGANISM: Triticum aestivum

<400> SEQUENCE: 30

```
Met Asp Gly Asp Ala Asp Ala Leu Lys Ser Gly Arg His Gly Ala Gly
  1               5                  10                  15

Asp Val Cys Gln Ile Cys Ala Asp Gly Leu Gly Thr Thr Leu Asp Gly
             20                  25                  30

Asp Val Phe Thr Ala Cys Asp Val Cys Arg Phe Pro Val Cys Arg Pro
         35                  40                  45

Cys Tyr Glu His Glu Arg Lys Glu Gly Thr Gln Ala Cys Leu Gln Cys
     50                  55                  60

Lys Thr Lys Tyr Lys Arg His Arg Gly Ser Pro Ala Ile Arg Gly Glu
 65                  70                  75                  80

Glu Gly Asp Asp Thr Asp Ala Asp Asp Gly Ser Asp Phe Asn Tyr Pro
                 85                  90                  95

Ala Ser Gly Thr Glu Asp Gln Lys Gln Lys Ile Ala Asp Arg Met Arg
            100                 105                 110

Ser Trp Arg Met Asn Thr Gly Gly Ser Gly Asn Val Gly His Pro Lys
        115                 120                 125

Tyr Asp Ser Gly Glu Ile Gly Leu Ser Lys Tyr Asp Ser Gly Glu Ile
    130                 135                 140

Pro Arg Gly Tyr Val Pro Ser Val Thr Asn Ser Gln Met Ser Gly Glu
145                 150                 155                 160

Ile Pro Gly Ala Ser Pro Asp His His Met Met Ser Pro Thr Gly Asn
                165                 170                 175

Ile Ser Arg Arg Ala Pro Phe Pro Tyr Val Asn His Ser Pro Asn Pro
            180                 185                 190

Ser Arg Glu Phe Ser Gly Ser Ile Gly Asn Val Ala Trp Lys Glu Arg
        195                 200                 205

Val Asp Gly Trp Lys Met Lys Gln Asp Lys Gly Ala Ile Pro Met Thr
    210                 215                 220

Asn Gly Thr Ser Ile Ala Pro Ser Glu Gly Arg Ala Ala Thr Asp Ile
225                 230                 235                 240

Asp Ala Ser Thr Glu Tyr Asn Met Glu Asp Ala Leu Leu Asn Asp Glu
                245                 250                 255

Thr Arg Gln Pro Leu Ser Arg Lys Val Pro Ile Ala Ser Ser Lys Ile
            260                 265                 270

Asn Pro Tyr Arg Met Val Ile Val Leu Arg Leu Val Val Leu Ser Ile
```

-continued

```
              275                 280                 285
Phe Leu His Tyr Arg Leu Thr Asn Pro Val Arg Asn Ala Tyr Pro Leu
290                 295                 300
Trp Leu Leu Ser Val Ile Cys Glu Ile Trp Phe Ala Leu Ser Trp Ile
305                 310                 315                 320
Leu Asp Gln Phe Pro Lys Trp Phe Pro Ile Asn Arg Glu Thr Tyr Leu
                325                 330                 335
Asp Arg Leu Ala Leu Arg Tyr Asp Arg Glu Gly Glu Pro Ser Gln Leu
                340                 345                 350
Ala Ala Val Asp Ile Phe Val Ser Thr Val Asp Pro Leu Lys Glu Pro
                355                 360                 365
Pro Ile Val Thr Ala Asn Thr Val Leu Ser Ile Leu Ala Val Asp Tyr
    370                 375                 380
Pro Val Asp Lys Val Ser Cys Tyr Val Ser Asp Asp Gly Ala Ser Met
385                 390                 395                 400
Leu Thr Phe Asp Ala Leu Ala Glu Thr Ser Glu Phe Ala Arg Lys Trp
                405                 410                 415
Val Pro Phe Val Lys Lys Tyr Asp Ile Glu Pro Arg Ala Pro Glu Phe
                420                 425                 430
Tyr Phe Cys Gln Lys Ile Asp Tyr Leu Lys Asp Lys Val Gln Pro Ser
                435                 440                 445
Phe Val Lys Asp Arg Arg Ala Met Lys Arg Glu Tyr Glu Glu Phe Lys
                450                 455                 460
Ile Arg Ile Asn Ala Leu Val Ser Lys Ala Leu Lys Val Pro Glu Glu
465                 470                 475                 480
Gly Trp Ile Met Gln Asp Gly Thr Pro Trp Pro Gly Asn Asn Thr Arg
                485                 490                 495
Asp His Pro Gly Met Ile Gln Val Phe Leu Gly His Ser Gly Gly Leu
                500                 505                 510
Asp Thr Glu Gly Asn Glu Leu Pro Arg Leu Val Tyr Val Ser Arg Glu
                515                 520                 525
Lys Arg Pro Gly Phe Gln His His Lys Lys Ala Gly Ala Met Asn Ala
530                 535                 540
Leu Val Arg Val Ser Ala Val Leu Thr Asn Gly Gln Tyr Met Leu Asn
545                 550                 555                 560
Leu Asp Cys Asp His Tyr Ile Asn Asn Ser Lys Ala Val Arg Glu Ala
                565                 570                 575
Met Cys Phe Leu Met Asp Pro Asn Leu Gly Pro Gln Val Cys Tyr Val
                580                 585                 590
Gln Phe Pro Gln Arg Phe Asp Gly Ile Asp Arg Asn Asp Arg Tyr Ala
                595                 600                 605
Asn Arg Asn Thr Val Phe Phe Asp Ile Asn Leu Arg Gly Leu Asp Gly
                610                 615                 620
Ile Gln Gly Pro Val Tyr Val Gly Thr Gly Cys Val Phe Asn Arg Thr
625                 630                 635                 640
Ala Ile Tyr Gly Tyr Glu Pro Pro Ile Lys Ala Lys Pro Lys Pro Gly Phe
                645                 650                 655
Leu Ala Ser Leu Cys Gly Gly Lys Lys Lys Ala Ser Lys Ser Lys Lys
                660                 665                 670
Arg Ser Ser Asp Lys Lys Lys Ser Asn Lys His Val Asp Ser Ser Val
                675                 680                 685
Pro Val Phe Asn Leu Glu Asp Ile Glu Glu Gly Val Glu Gly Ala Gly
                690                 695                 700
```

```
Phe Asp Asp Glu Lys Ser Val Leu Met Ser Gln Met Ser Leu Glu Lys
705                 710                 715                 720

Arg Phe Gly Gln Ser Ala Ala Phe Val Ala Ser Thr Leu Met Glu Tyr
            725                 730                 735

Gly Gly Val Pro Gln Ser Ser Thr Pro Glu Ser Leu Leu Lys Glu Ala
            740                 745                 750

Ile His Val Ile Ser Cys Gly Tyr Glu Asp Lys Ser Glu Trp Gly Thr
            755                 760                 765

Glu Ile Gly Trp Ile Tyr Gly Ser Val Thr Glu Asp Ile Leu Thr Gly
770                 775                 780

Phe Lys Met His Ala Arg Gly Trp Arg Ser Val Tyr Cys Met Pro Lys
785                 790                 795                 800

Arg Pro Ala Phe Lys Gly Ser Ala Pro Ile Asn Leu Ser Asp Arg Leu
            805                 810                 815

Asn Gln Val Leu Arg Trp Ala Leu Gly Ser Val Glu Ile Leu Phe Ser
            820                 825                 830

Arg His Cys Pro Leu Trp Tyr Gly Tyr Gly Gly Arg Leu Lys Phe Leu
835                 840                 845

Glu Arg Phe Ala Tyr Ile Asn Thr Thr Ile Tyr Pro Leu Thr Ser Leu
850                 855                 860

Pro Leu Leu Val Tyr Cys Ile Leu Pro Ala Ile Cys Leu Leu Thr Gly
865                 870                 875                 880

Lys Phe Ile Met Pro Glu Ile Ser Asn Leu Ala Ser Ile Trp Phe Ile
            885                 890                 895

Ala Leu Phe Leu Ser Ile Phe Ala Thr Gly Ile Leu Glu Met Arg Trp
            900                 905                 910

Ser Gly Val Gly Ile Asp Glu Trp Trp Arg Asn Glu Gln Phe Trp Val
            915                 920                 925

Ile Gly Gly Ile Ser Ala His Leu Phe Ala Val Phe Gln Gly Leu Leu
            930                 935                 940

Lys Val Leu Ala Gly Ile Asp Thr Asn Phe Thr Val Thr Ser Lys Ala
945                 950                 955                 960

Asn Asp Glu Glu Gly Asp Phe Ala Glu Leu Tyr Met Phe Lys Trp Thr
            965                 970                 975

Thr Leu Leu Ile Pro Pro Thr Thr Ile Leu Ile Ile Asn Met Val Gly
            980                 985                 990

Val Val Ala Gly Thr Ser Tyr Ala Ile Asn Ser Gly Tyr Gln Ser Trp
            995                 1000                1005

Gly Pro Leu Phe Gly Lys Leu Phe Phe Ala Phe Trp Val Ile Val His
    1010                1015                1020

Leu Tyr Pro Phe Leu Lys Gly Leu Met Gly Arg Gln Asn Arg Thr Pro
1025                1030                1035                1040

Thr Ile Val Ile Val Trp Ala Val Leu Leu Ala Ser Ile Phe Ser Leu
                1045                1050                1055

Leu Trp Val Arg Val Asp Pro Phe Thr Thr Arg Leu Ala Gly Pro Asn
        1060                1065                1070

Ile Gln Thr Cys Gly Ile Asn Cys
        1075                1080

<210> SEQ ID NO 31
<211> LENGTH: 685
<212> TYPE: PRT
<213> ORGANISM: Gossypium hirsutum
```

-continued

```
<400> SEQUENCE: 31

Arg Arg Trp Val Pro Phe Cys Lys Lys His Asn Val Glu Pro Arg Ala
  1               5                  10                  15

Pro Glu Phe Tyr Phe Asn Glu Lys Ile Asp Tyr Leu Lys Asp Lys Val
             20                  25                  30

His Pro Ser Phe Val Lys Glu Arg Arg Ala Met Lys Arg Glu Tyr Glu
         35                  40                  45

Glu Phe Lys Val Arg Ile Asn Ala Leu Val Ala Lys Ala Gln Lys Lys
     50                  55                  60

Pro Glu Glu Gly Trp Val Met Gln Asp Gly Thr Pro Trp Pro Gly Asn
 65                  70                  75                  80

Asn Thr Arg Asp His Pro Gly Met Ile Gln Val Tyr Leu Gly Ser Ala
                 85                  90                  95

Gly Ala Leu Asp Val Asp Gly Lys Glu Leu Pro Arg Leu Val Tyr Val
            100                 105                 110

Ser Arg Glu Lys Arg Pro Gly Tyr Gln His His Lys Lys Ala Gly Ala
        115                 120                 125

Glu Asn Ala Leu Val Arg Val Ser Ala Val Leu Thr Asn Ala Pro Phe
    130                 135                 140

Ile Leu Asn Leu Asp Cys Asp His Tyr Ile Asn Asn Ser Lys Ala Met
145                 150                 155                 160

Arg Glu Ala Met Cys Phe Leu Met Asp Pro Gln Phe Gly Lys Lys Leu
                165                 170                 175

Cys Tyr Val Gln Phe Pro Gln Arg Phe Asp Gly Ile Asp Arg His Asp
            180                 185                 190

Arg Tyr Ala Asn Arg Asn Val Val Phe Phe Asp Ile Asn Met Leu Gly
        195                 200                 205

Leu Asp Gly Leu Gln Gly Pro Val Tyr Val Gly Thr Gly Cys Val Phe
    210                 215                 220

Asn Arg Gln Ala Leu Tyr Gly Tyr Asp Pro Pro Val Ser Glu Lys Arg
225                 230                 235                 240

Pro Lys Met Thr Cys Asp Cys Trp Pro Ser Trp Cys Cys Cys Cys Cys
                245                 250                 255

Gly Gly Ser Arg Lys Ser Lys Lys Lys Gly Glu Lys Lys Gly Leu
            260                 265                 270

Leu Gly Gly Leu Leu Tyr Gly Lys Lys Lys Met Met Gly Lys Asn
        275                 280                 285

Tyr Val Lys Lys Gly Ser Ala Pro Val Phe Asp Leu Glu Glu Ile Glu
    290                 295                 300

Glu Gly Leu Glu Gly Tyr Glu Glu Leu Glu Lys Ser Thr Leu Met Ser
305                 310                 315                 320

Gln Lys Asn Phe Glu Lys Arg Phe Gly Gln Ser Pro Val Phe Ile Ala
                325                 330                 335

Ser Thr Leu Met Glu Asn Gly Gly Leu Pro Glu Gly Thr Asn Ser Thr
            340                 345                 350

Ser Leu Ile Lys Glu Ala Ile His Val Ile Ser Cys Gly Tyr Glu Glu
        355                 360                 365

Lys Thr Glu Trp Gly Lys Glu Ile Gly Trp Ile Tyr Gly Ser Val Thr
    370                 375                 380

Glu Asp Ile Leu Thr Gly Phe Lys Met His Cys Arg Gly Trp Lys Ser
385                 390                 395                 400

Val Tyr Cys Val Pro Lys Arg Pro Ala Phe Lys Gly Ser Ala Pro Ile
                405                 410                 415
```

```
Asn Leu Ser Asp Arg Leu His Gln Val Leu Arg Trp Ala Leu Gly Ser
            420                 425                 430

Val Glu Ile Phe Leu Ser Arg His Cys Pro Leu Trp Tyr Gly Tyr Gly
            435                 440                 445

Gly Lys Leu Lys Trp Leu Glu Arg Leu Ala Tyr Ile Asn Thr Ile Val
            450                 455                 460

Tyr Pro Phe Thr Ser Ile Pro Leu Leu Ala Tyr Cys Thr Ile Pro Ala
465                 470                 475                 480

Val Cys Leu Leu Thr Gly Lys Phe Ile Ile Pro Thr Leu Ser Asn Leu
            485                 490                 495

Thr Ser Val Trp Phe Leu Ala Leu Phe Leu Ser Ile Ile Ala Thr Gly
            500                 505                 510

Val Leu Glu Leu Arg Trp Ser Gly Val Ser Ile Gln Asp Trp Trp Arg
            515                 520                 525

Asn Glu Gln Phe Trp Val Ile Gly Gly Val Ser Ala His Leu Phe Ala
            530                 535                 540

Val Phe Gln Gly Leu Leu Lys Val Leu Ala Gly Val Asp Thr Asn Phe
545                 550                 555                 560

Thr Val Thr Ala Lys Ala Ala Asp Asp Thr Glu Phe Gly Glu Leu Tyr
            565                 570                 575

Leu Phe Lys Trp Thr Thr Leu Leu Ile Pro Pro Thr Thr Leu Ile Ile
            580                 585                 590

Leu Asn Met Val Gly Val Val Ala Gly Val Ser Asp Ala Ile Asn Asn
            595                 600                 605

Gly Tyr Gly Ser Trp Gly Pro Leu Phe Gly Lys Leu Phe Phe Ala Phe
            610                 615                 620

Trp Val Ile Leu His Leu Tyr Pro Phe Leu Lys Gly Leu Met Gly Arg
625                 630                 635                 640

Gln Asn Arg Thr Pro Thr Ile Val Val Leu Trp Ser Ile Leu Leu Ala
            645                 650                 655

Ser Ile Phe Ser Leu Val Trp Val Arg Ile Asp Pro Phe Leu Pro Lys
            660                 665                 670

Gln Thr Gly Pro Val Leu Lys Gln Cys Gly Val Glu Cys
            675                 680                 685

<210> SEQ ID NO 32
<211> LENGTH: 701
<212> TYPE: PRT
<213> ORGANISM: Gossypium hirsutum

<400> SEQUENCE: 32

Asp Tyr Pro Val Glu Lys Val Ser Cys Tyr Val Ser Asp Asp Gly Ala
1               5                   10                  15

Ala Met Leu Thr Phe Glu Ala Leu Ser Glu Thr Ser Glu Phe Ala Arg
            20                  25                  30

Lys Trp Val Pro Phe Cys Lys Lys Tyr Asn Ile Glu Pro Arg Ala Pro
            35                  40                  45

Glu Trp Tyr Phe Ala Gln Lys Ile Asp Tyr Leu Lys Asp Lys Val Gln
            50                  55                  60

Thr Ser Phe Val Lys Glu Arg Arg Ala Met Lys Arg Glu Tyr Glu Glu
65                  70                  75                  80

Phe Lys Val Arg Val Asn Gly Leu Val Ala Lys Ala Gln Lys Val Pro
            85                  90                  95

Glu Glu Gly Trp Ile Met Gln Asp Gly Thr Pro Trp Pro Gly Asn Asn
```

```
                      100                 105                 110
Thr Arg Asp His Pro Gly Met Ile Gln Val Phe Leu Gly Gln Ser Gly
            115                 120                 125

Gly Leu Asp Ala Glu Gly Asn Glu Leu Pro Arg Leu Tyr Val Ser
            130                 135                 140

Arg Glu Lys Arg Pro Gly Phe Gln His His Lys Lys Ala Gly Ala Met
145                 150                 155                 160

Asn Ala Leu Val Arg Val Ser Ala Val Leu Thr Asn Gly Ala Phe Leu
                165                 170                 175

Leu Asn Leu Asp Cys Asp His Tyr Ile Asn Asn Ser Lys Ala Leu Arg
                180                 185                 190

Glu Ala Met Cys Phe Leu Met Asp Pro Asn Leu Gly Lys Gln Val Cys
            195                 200                 205

Tyr Val Gln Phe Pro Gln Arg Phe Asp Gly Ile Asp Arg Asn Asp Arg
            210                 215                 220

Tyr Ala Asn Arg Asn Thr Val Phe Phe Asp Ile Asn Leu Arg Gly Leu
225                 230                 235                 240

Asp Gly Ile Gln Gly Pro Val Tyr Val Gly Thr Gly Cys Val Phe Asn
                245                 250                 255

Arg Thr Ala Leu Tyr Gly Tyr Glu Pro Pro Leu Lys Pro Lys His Arg
            260                 265                 270

Lys Thr Gly Ile Leu Ser Ser Leu Cys Gly Gly Ser Arg Lys Lys Ser
            275                 280                 285

Ser Lys Ser Ser Lys Lys Gly Ser Asp Lys Lys Ser Gly Lys His
            290                 295                 300

Val Asp Ser Thr Val Pro Val Phe Asn Leu Glu Asp Ile Glu Glu Gly
305                 310                 315                 320

Val Glu Gly Ala Gly Phe Asp Asp Glu Lys Ser Leu Leu Met Ser Gln
                325                 330                 335

Met Ser Leu Glu Lys Arg Phe Gly Gln Ser Ala Val Phe Val Ala Ser
            340                 345                 350

Thr Leu Met Glu Asn Gly Gly Val Pro Gln Ser Ala Thr Pro Glu Thr
            355                 360                 365

Leu Leu Lys Glu Ala Ile His Val Ile Ser Cys Gly Tyr Glu Asp Lys
370                 375                 380

Thr Asp Trp Gly Ser Glu Ile Gly Trp Ile Tyr Gly Ser Val Thr Glu
385                 390                 395                 400

Asp Ile Leu Thr Gly Phe Lys Met His Ala Arg Gly Trp Arg Ser Ile
                405                 410                 415

Tyr Cys Met Pro Lys Arg Pro Ala Phe Lys Gly Ser Ala Pro Ile Asn
            420                 425                 430

Leu Ser Asp Arg Leu Asn Gln Val Leu Arg Trp Ala Leu Gly Ser Val
            435                 440                 445

Glu Ile Leu Phe Ser Arg His Cys Pro Ile Trp Tyr Gly Tyr Ser Gly
            450                 455                 460

Arg Leu Lys Trp Leu Glu Arg Phe Ala Tyr Val Asn Thr Thr Ile Tyr
465                 470                 475                 480

Pro Val Thr Ala Ile Pro Leu Leu Met Tyr Cys Thr Leu Pro Ala Val
                485                 490                 495

Cys Leu Leu Thr Asn Lys Phe Ile Ile Pro Gln Ile Ser Asn Leu Ala
            500                 505                 510

Ser Ile Trp Phe Ile Ser Leu Phe Leu Ser Ile Phe Ala Thr Gly Ile
            515                 520                 525
```

```
Leu Lys Met Lys Trp Asn Gly Val Gly Ile Asp Gln Trp Trp Arg Asn
        530                 535                 540

Glu Gln Phe Trp Val Ile Gly Val Ser Ala His Leu Phe Ala Val
545                 550                 555                 560

Phe Gln Gly Leu Leu Lys Val Leu Ala Gly Ile Asp Thr Asn Phe Thr
                565                 570                 575

Val Thr Ser Lys Ala Ser Asp Glu Asp Gly Asp Phe Ala Glu Leu Tyr
            580                 585                 590

Met Phe Lys Trp Thr Thr Leu Leu Ile Pro Pro Thr Thr Leu Leu Ile
        595                 600                 605

Ile Asn Leu Val Gly Val Ala Gly Ile Ser Tyr Val Ile Asn Ser
    610                 615                 620

Gly Tyr Gln Ser Trp Gly Pro Leu Phe Gly Lys Leu Phe Phe Ala Phe
625                 630                 635                 640

Trp Val Ile Ile His Leu Tyr Pro Phe Leu Lys Gly Leu Met Gly Arg
                645                 650                 655

Gln Asn Arg Thr Pro Thr Ile Val Val Val Trp Ser Ile Leu Leu Ala
            660                 665                 670

Ser Ile Phe Ser Leu Leu Trp Val Arg Ile Asp Pro Phe Thr Thr Arg
        675                 680                 685

Val Thr Gly Pro Asp Val Glu Gln Cys Gly Ile Asn Cys
    690                 695                 700

<210> SEQ ID NO 33
<211> LENGTH: 1065
<212> TYPE: PRT
<213> ORGANISM: Arabidopsis thaliana

<400> SEQUENCE: 33

Met Glu Ser Glu Gly Glu Thr Ala Gly Lys Pro Met Lys Asn Ile Val
 1               5                  10                  15

Pro Gln Thr Cys Gln Ile Cys Ser Asp Asn Val Gly Lys Thr Val Asp
            20                  25                  30

Gly Asp Arg Phe Val Ala Cys Asp Ile Cys Ser Phe Pro Val Cys Arg
        35                  40                  45

Pro Cys Tyr Glu Tyr Glu Arg Lys Asp Gly Asn Gln Ser Cys Pro Gln
    50                  55                  60

Cys Lys Thr Arg Tyr Lys Arg Leu Lys Gly Ser Pro Ala Ile Pro Gly
65                  70                  75                  80

Asp Lys Asp Glu Asp Gly Leu Ala Asp Glu Gly Thr Val Glu Phe Asn
                85                  90                  95

Tyr Pro Gln Lys Glu Lys Ile Ser Glu Arg Met Leu Gly Trp His Leu
            100                 105                 110

Thr Arg Gly Lys Gly Glu Glu Met Gly Glu Pro Gln Tyr Asp Lys Glu
        115                 120                 125

Val Ser His Asn His Leu Pro Arg Leu Thr Ser Arg Gln Asp Thr Ser
    130                 135                 140

Gly Glu Phe Ser Ala Ala Ser Pro Glu Arg Leu Ser Val Ser Ser Thr
145                 150                 155                 160

Ile Ala Gly Gly Lys Arg Leu Pro Tyr Ser Ser Asp Val Asn Gln Ser
                165                 170                 175

Pro Asn Arg Arg Ile Val Asp Pro Val Gly Leu Gly Asn Val Ala Trp
            180                 185                 190

Lys Glu Arg Val Asp Gly Trp Lys Met Lys Gln Glu Lys Asn Thr Gly
```

```
            195                 200                 205
Pro Val Ser Thr Gln Ala Ala Ser Glu Arg Gly Gly Val Asp Ile Asp
210                 215                 220

Ala Ser Thr Asp Ile Leu Ala Asp Glu Ala Leu Leu Asn Asp Glu Ala
225                 230                 235                 240

Arg Gln Pro Leu Ser Arg Lys Val Ser Ile Pro Ser Ser Arg Ile Asn
                    245                 250                 255

Pro Tyr Arg Met Val Ile Met Leu Arg Leu Val Ile Leu Cys Leu Phe
                260                 265                 270

Leu His Tyr Arg Ile Thr Asn Pro Val Pro Asn Ala Phe Ala Leu Trp
            275                 280                 285

Leu Val Ser Val Ile Cys Glu Ile Trp Phe Ala Leu Ser Trp Ile Leu
        290                 295                 300

Asp Gln Phe Pro Lys Trp Phe Pro Val Asn Arg Glu Thr Tyr Leu Asp
305                 310                 315                 320

Arg Leu Ala Leu Arg Tyr Asp Arg Glu Gly Glu Pro Ser Gln Leu Ala
                    325                 330                 335

Ala Val Asp Ile Phe Val Ser Thr Val Asp Pro Leu Lys Glu Pro Pro
                340                 345                 350

Leu Val Thr Ala Asn Thr Val Leu Ser Ile Leu Ala Val Asp Tyr Pro
            355                 360                 365

Val Asp Lys Val Ser Cys Tyr Val Phe Asp Asp Gly Ala Ala Met Leu
        370                 375                 380

Ser Phe Glu Ser Leu Ala Glu Thr Ser Glu Phe Ala Arg Lys Trp Val
385                 390                 395                 400

Pro Phe Cys Lys Lys Tyr Ser Ile Glu Pro Arg Ala Pro Glu Trp Tyr
                    405                 410                 415

Phe Ala Ala Lys Ile Asp Tyr Leu Lys Asp Lys Val Gln Thr Ser Phe
                420                 425                 430

Val Lys Asp Arg Arg Ala Met Lys Arg Glu Tyr Glu Glu Phe Lys Ile
            435                 440                 445

Arg Ile Asn Ala Leu Val Ser Lys Ala Leu Lys Cys Pro Glu Glu Gly
450                 455                 460

Trp Val Met Gln Asp Gly Thr Pro Trp Pro Gly Asn Asn Thr Gly Asp
465                 470                 475                 480

His Pro Gly Met Ile Gln Val Phe Leu Gly Gln Asn Gly Gly Leu Asp
                    485                 490                 495

Ala Glu Gly Asn Glu Leu Pro Arg Leu Val Tyr Val Ser Arg Glu Lys
                500                 505                 510

Arg Pro Gly Phe Gln His His Lys Lys Ala Gly Ala Met Asn Ala Leu
            515                 520                 525

Val Arg Val Ser Ala Val Leu Thr Asn Gly Pro Phe Ile Leu Asn Leu
530                 535                 540

Asp Cys Asp His Tyr Ile Asn Asn Ser Lys Ala Leu Arg Glu Ala Met
545                 550                 555                 560

Cys Phe Leu Met Asp Pro Asn Leu Gly Lys Gln Val Cys Tyr Val Gln
                    565                 570                 575

Phe Pro Gln Arg Phe Asp Gly Ile Asp Lys Asn Asp Arg Tyr Ala Asn
                580                 585                 590

Arg Asn Thr Val Phe Phe Asp Ile Asn Leu Arg Gly Leu Asp Gly Ile
            595                 600                 605

Gln Gly Pro Val Tyr Val Gly Thr Gly Cys Val Phe Asn Arg Thr Ala
610                 615                 620
```

-continued

Leu Tyr Gly Tyr Glu Pro Pro Ile Lys Val Lys His Lys Lys Pro Ser
625                 630                 635                 640

Leu Leu Ser Lys Leu Cys Gly Gly Ser Arg Lys Lys Asn Ser Lys Ala
            645                 650                 655

Lys Lys Glu Ser Asp Lys Lys Ser Gly Arg His Thr Asp Ser Thr
        660                 665                 670

Val Pro Val Phe Asn Leu Asp Asp Ile Glu Glu Gly Val Glu Gly Ala
            675                 680                 685

Gly Phe Asp Asp Glu Lys Ala Leu Leu Met Ser Gln Met Ser Leu Glu
        690                 695                 700

Lys Arg Phe Gly Gln Ser Ala Val Phe Val Ala Ser Thr Leu Met Glu
705                 710                 715                 720

Asn Gly Gly Val Pro Pro Ser Ala Thr Pro Glu Asn Leu Leu Lys Glu
                725                 730                 735

Ala Ile His Val Ile Ser Cys Gly Tyr Glu Asp Lys Ser Asp Trp Gly
            740                 745                 750

Met Glu Ile Gly Trp Ile Tyr Gly Ser Val Thr Glu Asp Ile Leu Thr
        755                 760                 765

Gly Phe Lys Met His Ala Arg Gly Trp Arg Ser Ile Tyr Cys Met Pro
    770                 775                 780

Lys Leu Pro Ala Phe Lys Gly Ser Ala Pro Ile Asn Leu Ser Asp Arg
785                 790                 795                 800

Leu Asn Gln Val Leu Arg Trp Ala Leu Gly Ser Val Glu Ile Leu Phe
            805                 810                 815

Ser Arg His Cys Pro Ile Trp Tyr Gly Tyr Asn Gly Arg Leu Lys Phe
        820                 825                 830

Leu Glu Arg Phe Ala Tyr Val Asn Thr Thr Ile Tyr Pro Ile Thr Ser
        835                 840                 845

Ile Pro Leu Leu Met Tyr Cys Thr Leu Ala Val Cys Leu Phe Thr
850                 855                 860

Asn Gln Phe Ile Ile Pro Gln Ile Ser Asn Ile Ala Ser Ile Trp Phe
865                 870                 875                 880

Leu Ser Leu Phe Leu Ser Ile Phe Ala Thr Gly Ile Leu Glu Met Arg
            885                 890                 895

Trp Ser Gly Val Gly Ile Asp Glu Trp Trp Arg Asn Glu Gln Phe Trp
        900                 905                 910

Val Ile Gly Gly Val Ser Ala His Leu Phe Ala Val Phe Gln Gly Ile
            915                 920                 925

Leu Lys Val Leu Ala Gly Ile Asp Thr Asn Phe Thr Val Thr Ser Lys
930                 935                 940

Ala Ser Asp Glu Asp Gly Asp Phe Ala Glu Leu Tyr Leu Phe Lys Trp
945                 950                 955                 960

Thr Thr Leu Leu Ile Pro Pro Thr Thr Leu Leu Ile Val Asn Leu Val
            965                 970                 975

Gly Val Val Ala Gly Val Ser Tyr Ala Ile Asn Ser Gly Tyr Gln Ser
        980                 985                 990

Trp Gly Pro Leu Phe Gly Lys Leu Phe Phe Ala Phe Trp Val Ile Val
    995                 1000                1005

His Leu Tyr Pro Phe Leu Lys Gly Leu Met Gly Arg Gln Asn Arg Thr
    1010                1015                1020

Pro Thr Ile Val Val Trp Ser Val Leu Leu Ala Ser Ile Phe Ser
1025                1030                1035                1040

-continued

```
Leu Leu Trp Val Arg Ile Asp Pro Phe Thr Ser Arg Val Thr Gly Pro
            1045                1050                1055
Asp Ile Leu Glu Cys Gly Ile Asn Cys
        1060                1065
```